(12) United States Patent
Schalk

(10) Patent No.: US 9,267,155 B2
(45) Date of Patent: *Feb. 23, 2016

(54) METHOD FOR PRODUCING SCLAREOL

(71) Applicant: FIRMENICH SA, Geneva (CH)

(72) Inventor: Michel Schalk, Collonges-Sous-Saleve (FR)

(73) Assignee: FIRMENICH SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/136,938

(22) Filed: Dec. 20, 2013

(65) Prior Publication Data

US 2014/0162332 A1    Jun. 12, 2014

Related U.S. Application Data

(63) Continuation of application No. 12/865,298, filed as application No. PCT/EP2009/050816 on Jan. 26, 2009, now Pat. No. 8,617,860.

(30) Foreign Application Priority Data

Jan. 29, 2008  (EP) .................................... 08101075
Mar. 17, 2008  (EP) .................................... 08102661
Mar. 20, 2008  (EP) .................................... 08102811

(51) Int. Cl.
*C12P 7/02*     (2006.01)
*C12N 9/16*    (2006.01)
*C12P 7/18*    (2006.01)

(52) U.S. Cl.
CPC ... *C12P 7/02* (2013.01); *C12N 9/16* (2013.01); *C12P 7/18* (2013.01)

(58) Field of Classification Search
CPC .............. C12N 9/16; C12N 9/88; C12N 9/93; C12P 7/18
USPC ................... 435/156, 419; 536/23.2
See application file for complete search history.

(56) References Cited

U.S. PATENT DOCUMENTS 8,617,860 B2 * 12/2013 Schalk ........................ 435/156
2011/0041218 A1  2/2011 Schalk

OTHER PUBLICATIONS

Altschul, Stephen F., "Amino Acid Substitution Matrices from an Information Theoretic Perspective" J. Mol. Biol., 219, 555-565 (1991).
Altschul, Stephen F. et al., "Basic Local Alignment Search Tool" J. Mol. Biol., 215, 403-410 (1990).
Banthorpe, Derek V. et al., "Partial Purification of Farnesyl Pyrophosphate: Drimenol Cyclase and Geranylgeranyl Pyrophosphate: Sclareol Cyclase, Using Cell Culture as a Source of Material" Phytochemistry, 31(10), 3391-3395 (1992).
Dewick, Paul M., "The biosynthesis of C5-C25 terpenoid compounds" Nat. Prod. Rep., 19, 181-222 (2002).
Emanuelsson, Olof et al., "ChloroP, a neural network based method for predicting chloroplast transit peptides and their cleavage sites" Protein Science, 8, 978-984 (1999).
Horton, Robert M. et al., "Engineering hybrid genes without the use of restriction enzymes: gene splicing by overlap extension" Gene, 77, 61-68 (1989).
Huang, Xiaoqiu "A Contig Assembly Program Based on Sensitive Detection of Fragment Overlaps" Genomics, 14, 18-25 (1992).
Huang, Qiulong et al., "Engineering *Escherichia coli* for the synthesis of Tazadiene, a Key Intermediate in the Biosynthesis of Taxol" Bioorganic & Medicinal Chemistry, 9, 2237-2242 (2001).
Keller, R. Kennedy et al., "Rapid synthesis of isoprenoid diphosphates and their isolation in one step using either thin layer or flash chromatography" Journal of Chromatography, 645, 161-167 (1993).
Margis-Pinheiro, Marcia et al., "Isolation and characterization of Ds-tagged rice (*Oryza sativa* L.) GA-responsive dwarf mutant defective in an early step of the gibberellins biosynthesis pathway" Plant Cell Rep, 23, 819-833 (2005).
Schardl, Christopher L. et al., "Design and construction of a versatile system for the expression of foreign genes in plants" Gene., 61, 1-11 (1987).
Stemmer, Willem P.C., "DNA shuffling by random fragmentation and reassembly: In vitro recombination for molecular evolution" Proc. Natl. Acad. Sci. USA, 91, 10747-10751 (1994).
Tatusova ,Tatiana A. et al., "BLAST 2 Sequences, a new tool for comparing protein and nucleotide sequences" FEMS Microbiology Letters, 174, 247-250 (1999).
Wendt, K Ulrich et al., "Isoprenoid biosynthesis: manifold chemistry catalyzed by similar enzymes" Structure, 6(2), 127-133 (1998).
Xu, Meimei et al., "Functional characterization of the rice kaurene synthase-like gene family" Phytochemistry, 68, 312-326 (2007).
Lange, B. Markus et al., "Probing essential oil biosynthesis and secretion by functional evaluation of expressed sequence tags from mint glandular trichomes" PNAS, 97(6), 2934-2939 (2000).
Guo, Zhenhua et al., "Biosynthesis of labdencdiol and sclareol in cell-free extracts from trichomes of Nicotiana glutinosa" Planta, 197, 627-632 (1995).
Banthorpe, Derek V. et al., "Accumulation of the Anti-Fungal Diterpene Sclareol by Cell Cultures of Saliva Sclarea and Nicotiana Glutinosa" Phytochemistry, 29(7), 2145-2148 (1990).
Nichols, Harold J., "Biosynthesis of Sclareol, β-Sitosterol, and Oleanolic Acid from Mevalonic Acid-2-C14" The Journal of Biological Chemistry, 237(5), 1481-1484 (1962).
D'Auria, John C et al., "The secondary metabolism of Arabidopsis thaliana: growing like a weed" Current Opinion in Plant Biology, 8, 308-316 (2005).

* cited by examiner

*Primary Examiner* — Tekchand Saidha

(57) ABSTRACT

The present invention provides a method of producing sclareol, the method comprising contacting a particular polypeptide having a sclareol synthase activity with labdenediol diphosphate (LPP). In particular, the method may be carried out in vitro or in vivo to produce sclareol, a very useful compound in the fields of perfumery and flavoring. The present invention also provides the amino acid sequence of the polypeptide used in the method. A nucleic acid derived from *Salvia sclarea* and encoding the polypeptide of the invention, an expression vector containing the nucleic acid, as well as a non-human organism or a cell transformed to harbor the same nucleic acid, are also part of the present invention.

16 Claims, 12 Drawing Sheets labdenediol diphosphate sclareol
(-)-(13R)-14-labdene-8,13-diol (-)-Ambrox geranylgeranyl diphosphate (GGPP)

ent-kaurene ent-cassa-12,15-diene

Figure 4B

METHOD FOR PRODUCING SCLAREOL

RELATED APPLICATIONS

This application is a continuation of U.S. patent application Ser. No. 12/865,298, filed on Jul. 29, 2010, which is a '371 application of PCT Application No. PCT/EP2009/050816, filed Jan. 26, 2009, the contents of both of which are incorporated by reference.

INCORPORATION BY REFERENCE OF SEQUENCE LISTING

The Sequence Listing in the ASCII text file, named as 26333_SeqRevised2.txt of 157 KB, to created on Jun. 26, 2013, and submitted to the United States Patent and Trademark Office via EFS-Web, is incorporated herein by reference.

TECHNICAL FIELD

The present invention provides a method of producing sclareol, said method comprising contacting a particular polypeptide having a sclareol synthase activity with labdenediol diphosphate (LPP). In particular, said method may be carried out in vitro or in vivo to produce sclareol, a very useful compound in the fields of perfumery and flavoring. The present invention also provides the amino acid sequence of the polypeptide used in the method. A nucleic acid derived from *Salvia sclarea* and encoding the polypeptide of the invention, an expression vector containing said nucleic acid, as well as a non-human organism or a cell transformed to harbor the same nucleic acid, are also part of the present invention.

PRIOR ART

Sclareol is one member of the terpenoids or terpenes family, comprising a high number of natural products. Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Diterpenes, for example, are widely found in the plant kingdom and over 2500 diterpene structures have been described (Connolly and Hill, Dictionary of terpenoids, 1991, Chapman & Hall, London). Terpene molecules have been of interest for thousands of years because of their flavor and fragrance properties and their cosmetic, medicinal and antimicrobial effects. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. These enzymes convert a precursor in one or more terpene products. Most of the time, the precursor is an acyclic terpene precursor and, in particular, most diterpene synthases catalyze the cyclization of the acyclic precursor geranylgeranyl pyrophosphate. Nevertheless, in some special cases, terpene synthases catalyze the transformation of an to already cyclic molecule into one or more terpene products.

Two types of cyclization mechanisms occur in nature and are related to two types of diterpene synthases which can be classified into class I and class II diterpene synthases (Wendt and Schulz, 1998, Structure. 6(2):127-33). For some diterpenes, the cyclization mechanism is similar to those of monoterpenes and sesquiterpenes as it is initiated by the ionization of the diphosphate ester function of GGPP, followed by the reaction of the resulting carbocation with an internal double bond. The diterpene synthases catalysing this type of cyclization are class I diterpene synthases. The second mode of cyclization in the biosynthesis of diterpenes, catalyzed by class II diterpene synthases, is initiated by the protonation of the terminal double bond of GGPP and leads, after internal rearrangement and proton elimination, to a cyclic diterpene diphosphate intermediate.

Genes and cDNAs encoding diterpene synthases from each of the two classes have been cloned and the recombinant enzymes characterized. The availability of genes encoding different types of diterpene synthases provides information on the primary structures of the enzymes. Some amino acid motifs are conserved in diterpene synthases and are related to either the protonation or the ionization dependent cyclization. A DDxxD motif is found in several class I diterpene synthases. Said motif is probably involved in binding and ionization of the diphosphate moiety. In class II synthases, a conserved DxDD motif is found, in which the second aspartate residue is involved as proton donor.

Sclareol is a naturally occurring diterpene molecule extensively used as starting material for the synthesis of fragrance molecules with ambergris notes. These syntheses were developed to provide an alternative to ambergris, a waxy substance secreted by the intestines of sperm whale. Ambergris is highly appreciated for its pleasant odor and has been historically used as a perfume ingredient. Due to its high price and the increasing demand for ambergris, and particularly due to the protection of the whale species, chemical synthesis of ambergris constituents and molecules with ambergris character have been developed. Amongst these molecules, Ambrox® (registered trademark of Firmenich SA, Switzerland) is the most largely appreciated substitute for Ambergris. The most widely used starting material for the synthesis of Ambrox® is the diterpene-diol sclareol.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years. Therefore, it would be an advantage to provide a source of sclareol, which is less subjected to fluctuations in availability and quality. Chemical synthesis would seem to be an evident option for the preparation of sclareol. However, given its highly complex structure, an economic synthetic process for the preparation of sclareol is still difficult. A biochemical pathway leading to the synthesis of sclareol would therefore be of great interest.

The biosynthesis of terpenes in plants and other organisms has been extensively studied and is not further detailed in here, but reference is made to Dewick, *Nat. Prod. Rep.*, 2002, 19, 181-222, which reviews the state of the art of terpene biosynthetic pathways.

Several diterpene synthases have already been identified. In particular, U.S. Pat. No. 7,238,514 discloses a number of diterpene synthases, the nucleic acids encoding them, as well as unicellular organisms transformed to express each of these synthases together with a GGPP synthase, thus producing diterpenes in vivo. Nevertheless, no method for the biosynthetic production of sclareol using a polypeptide having a sclareol synthase activity as provided herein is specifically disclosed in that patent. The amino acid and nucleotide sequences disclosed in it are very different from the sequences of the present invention. Among the diterpene synthases described in that document, the closest to the polypeptides of the present invention are a *Cucumis sativus* mRNA for an ent-kaurene synthase designated by SEQ ID NO:389 in U.S. Pat. No. 7,238,514 and a *Cucurbita maxima* mRNA for an ent-kaurene synthase B designated by SEQ ID NO:395 in U.S. Pat. No. 7,238,514 and by the accession number AAB39482.1. These polypeptides and the one of the invention only share 32% identity. Moreover, there is no suggestion in this prior art document that the described diterpene synthases are useful for the production of sclareol.

Terpene synthases having a certain percentage of sequence identity with the sequences of the present invention have also been found in the sequences databases. Nevertheless, the percentage of identity between the known diterpene synthases and the polypeptides of the invention is very low. The closest synthases to the ones of the invention are a terpenoid cyclase of undefined function (Accession number NCBI AAS98912) having 36% identity with the polypeptide of the invention, an ent-kaurene synthase of *Cucumis sativus* (accession number BAB19275) having 32% identity with the polypeptide of the invention, an ent-cassadiene synthase from *Oryza sativa* (accession number ABH10734 and published in Xu, Wilderman, Morrone, Xu, Roy, Margis-Pinheiro, Upadhyaya, Coates and Peters, Functional characterization of the rice kaurene synthase-like gene family, Phytochemistry, 68(3), 2007, 312-326) having 32% identity with the polypeptide of the invention and an ent-kaurene synthase from *Oryza sativa* (accession number AAQ72559 and published in Margis-Pinheiro, Zhou, Zhu, Dennis and Upadhyaya, Isolation and characterization of a DS-tagged rice (*Oryza sativa* L.) GA-responsive dwarf mutant defective in an early step of the gibberellins biosynthesis pathway, Plant Cell Rep., 23(12), 2005, 819-833) having 32% identity with the polypeptide of the invention. The potential ability of any of these sequences to catalyze the production of sclareol is never mentioned in the prior art.

In addition to the difference between the sequences themselves, it also has to be pointed out that the structure and the properties of ent-kaurene and ent-cassadiene are very different from those of sclareol. In particular, ent-kaurene is a tricyclic diterpene which does not contain any alcohol functional groups, unlike sclareol, which is a bicyclic diol. Moreover, ent-kaurene, which is a precursor of a plant hormone regulating growth, is of no use in the field of perfumery and flavoring, whereas sclareol is of high interest in these technical fields, as explained above.

One document of the prior art relates specifically to a sclareol synthase (Banthorpe, Brown and Morris, Partial purification of farnesyl pyrophosphate: Drimenol cyclase and geranylgeranyl pyrophosphate: Sclareol cyclase, using cell culture as a source of material, Phytochemistry 31, 1992, 3391-3395). In this reference, a partially purified protein from *Nicotiana glutinosa* is identified as a sclareol synthase, but no indication is given regarding the amino acid sequence of that protein, the nucleotide sequence of the nucleic acid encoding it or the use of that protein in a method for the biosynthesis of sclareol in vitro or in vivo.

Despite extensive studies of terpene cyclization, the isolation and characterization of the enzymes is still difficult, particularly in plants, due to their low abundance, their often transient expression patterns, and the complexity of purifying them from the mixtures of resins and phenolic compounds in tissues where they are expressed.

It is an objective of the present invention to provide methods for making sclareol in an economic way, as indicated above. Accordingly, the present invention has the objective to produce diterpenes while having little waste, a more energy and resource efficient process and while reducing dependency on fossil fuels. It is a further objective to provide enzymes capable of sythesizing sclareol, which is useful as perfumery and/or aroma ingredients.

Abbreviations Used
bp base pair
kb kilo base
BSA bovine serum albumine
DNA deoxyribonucleic acid
cDNA complementary DNA
dT deoxy thymine
dNTP deoxy nucleotide triphosphate
DTT dithiothreitol
GC gaseous chromatograph
GGPP Geranylgeranyl pyrophosphate
IPTG isopropyl-D-thiogalacto-pyranoside
LB lysogeny broth
LPP labdenediol diphosphate
MOPSO 3-(N-morpholino)-2-hydroxypropanesulfonic acid
MS mass spectrometer
ORF open reading frame
PCR polymerase chain reaction
RMCE recombinase-mediated cassette exchange
RT-PCR reverse transcription-polymerase chain reaction
3'-/5'-RACE 3' and 5' rapid amplification of cDNA ends
RNA ribonucleic acid
mRNA messenger ribonucleic acid
nt nucleotide
RNase ribonuclease
RuBisCO ribulose-1,5-bisphosphate carboxylase
SDS-PAGE SDS-polyacrylamid gel electrophoresis
SsLPPs *Salvia sclarea* labdenediol diphosphate synthase
UTR Untranslated Region

DESCRIPTION OF THE INVENTION

The present invention provides a method to biosynthetically produce sclareol in an economic, reliable and reproducible way.

One object of the present invention is therefore a method for producing sclareol comprising
a) contacting labdenediol diphosphate (LPP) with at least one polypeptide having a sclareol synthase activity and comprising an amino acid sequence at least 50% identical to SEQ ID NO:1; and
b) optionally, isolating the sclareol produced in step a).

The method can be carried out in vitro as well as in vivo, as will be explained in details further on.

Sclareol and LPP are defined by the way of their formulae as represented in FIG. 1.

As a "sclareol synthase" or as a "polypeptide having a sclareol synthase activity", we mean here a polypeptide capable of catalyzing the synthesis of sclareol starting from (LPP). The ability of a polypeptide to catalyze the synthesis of sclareol can be confirmed by performing the enzyme assay as detailed in the Examples.

According to the present invention, polypeptides are also meant to include truncated polypeptides provided that they keep their sclareol synthase activity as defined above and that they share at least the defined percentage of identity with the corresponding fragment of SEQ ID NO:1.

According to a preferred embodiment, the method for producing sclareol comprises contacting LPP with a polypeptide having a sclareol synthase activity and comprising an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, said polypeptide comprises the amino acid sequence SEQ ID NO:1. In an even more preferred embodiment, said polypeptide consists of SEQ ID NO:1.

According to a preferred embodiment, the sclareol synthase is a truncated polypeptide comprising an amino acid sequence at least 50% identical to SEQ ID NO:102. Preferably the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:96. According to another preferred embodiment, the polypeptide comprises the amino acid sequence SEQ ID NO:96. According to a more preferred embodiment, the polypeptide consists of SEQ ID NO:96.

The percentage of identity between two peptidic or nucleotidic sequences is a function of the number of amino acids or nucleic acids residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for purposes of determining the percentage of amino acid or nucleic acid sequence identity can be achieved in various ways using computer programs and for instance publicly available computer programs available on the world wide web. Preferably, the BLAST program (Tatiana et al, FEMS Microbiol Lett., 1999, 174:247-250, 1999) set to the default parameters, available from the National Center for Biotechnology Information (NCBI), can be used to obtain an optimal alignment of peptidic or nucleotidic sequences and to calculate the percentage of sequence identity.

The polypeptide to be contacted with LPP in vitro can be obtained by extraction from any organism expressing it, using standard protein or enzyme extraction technologies. If the host organism is a unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptides, either in an isolated form or together with other proteins, for example in a crude protein extract obtained from cultured cells or microorganisms, may then be suspended in a buffer solution at optimal pH. If adequate, salts, DTT, BSA and other kinds of enzymatic co-factors, may be added in order to optimize enzyme activity. Appropriate conditions are described in more details in the Examples further on.

LPP may then be added to the suspension or solution, which is then incubated at optimal temperature, for example between 15 and 40° C., preferably between 25 and 35° C., more preferably at 30° C. After incubation, the sclareol produced may be isolated from the incubated solution by standard isolation procedures, such as solvent extraction and distillation, optionally after removal of polypeptides from the solution.

LPP can be obtained by contacting GGPP with an isolated LPP synthase. Examples 1 to 3 below show a method to isolate a LPP synthase encoding cDNA from *Salvia sclarea*, a method for the heterologous expression of said cDNA in *E. coli*, a method for the purification of the LPP synthase so produced and a method for the in vitro production of LPP using the isolated LPP synthase.

According to another preferred embodiment, the method for producing sclareol is carried out in vivo. In this case, step a) of the above-described method comprises cultivating a non-human organism or cell capable of producing LPP and transformed to express a polypeptide having a sclareol synthase activity and comprising an amino acid sequence at least 70% identical to SEQ ID NO:1 under conditions conducive to the production of sclareol.

According to a more preferred embodiment, the method further comprises, prior to step a), transforming a non human organism or cell capable of producing LPP with at least one nucleic acid encoding a polypeptide having a sclareol synthase activity and comprising an amino acid sequence at least 70% identical to SEQ ID NO:1, so that said organism expresses said polypeptide.

According to a preferred embodiment, the nucleic acid used to transform the host organism or cell comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to another preferred embodiment, the nucleic acid comprises the nucleotide sequence SEQ ID NO:2 or the complement thereof. According to a more preferred embodiment, the nucleic acid consists of SEQ ID NO:2 or the complement thereof.

According to a further preferred embodiment, the nucleic acid used to transform the host organism or cell is a truncated nucleic acid comprising a nucleotide sequence at least 50%, preferably at least 55%, preferably at least 60%, preferably at least 70%, preferably at least 75%, preferably at least 80%, preferably at least 85%, preferably at least 90%, more preferably at least 95% and even more preferably at least 98% identical to SEQ ID NO:93 or the complement thereof. According to another preferred embodiment, the nucleic acid comprises the nucleotide sequence SEQ ID NO:93 or the complement thereof. According to a more preferred embodiment, the nucleic acid consists of SEQ ID NO:93 or the complement thereof.

These embodiments of the invention are particularly advantageous since it is possible to carry out the method in vivo without previously isolating the polypeptide. The reaction occurs directly within the organism or cell transformed to express said polypeptide.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human organism or cell will be described later on in the part of the specification that is dedicated to such transformed non-human organisms or cells as specific objects of the present invention and in the Examples.

A particular organism or cell is meant to be "capable of producing LPP" when it produces LPP naturally or when it does not produce LPP naturally but produces GGPP (or is so transformed) and is transformed to express a LPP synthase, either prior to the transformation with a nucleic acid encoding a sclareol synthase or together with said nucleic acid. Organisms or cells transformed to produce a higher amount of LPP than the naturally occurring organism or cell are also encompassed by the "organisms or cells capable of producing LPP". According to a preferred embodiment, the organism accumulates LPP naturally or is transformed to accumulate LPP.

Methods for transforming organisms so that they express a LPP synthase, can be any method known in the art to transform a host organism. Such methods are exposed in more details later on and a specific example of the expression of a LPP synthase in *E. coli* is given in Example 2. Methods for transforming an organism to produce GGPP are also known in the art. Such methods can for example be found in Huang, Roessner, Croteau and Scott, Engineering *Escherichia coli* for the synthesis of taxadiene, a key intermediate in the biosynthesis of taxol, Bioorg Med. Chem., 9(9), 2001, 2237-2242.

To carry out the invention in vivo, the host organism or cell is cultivated under conditions conducive to the production of sclareol. Accordingly, if the host is a transgenic plant, optimal growth conditions are provided, such as optimal light, water and nutrient conditions, for example. If the host is a unicellular organism, conditions conducive to the production of sclareol may comprise addition of suitable cofactors to the culture medium of the host. In addition, a culture medium may be selected, so as to maximize sclareol synthesis. Optimal culture conditions are described in a more detailed manner in the following Examples.

Non-human organisms suitable to carry out the method of the invention in vivo may be any non-human multicellular or unicellular organisms. In a preferred embodiment, the non-human organism used to carry out the invention in vivo is a plant, a prokaryote or a fungus.

Any plant, prokaryote or fungus may be used to carry out the method of the invention in vivo. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*. In a more preferred embodiment the non-human organism is a microorganism.

According to an even more preferred embodiment said microorganism is a bacteria or a fungus, preferably said fungus is yeast. Most preferably, said bacteria is *E. coli* and said yeast is *Saccharomyces cerevisiae*.

Most of these organisms do not produce LPP naturally. To be suitable to carry out the method of the invention, these organisms have to be transformed to produce said precursor. They can be so transformed either before the modification with the nucleic acid encoding the polypeptide having a sclareol synthase activity or simultaneously, as explained above.

Isolated higher eukaryotic cells can also be used, instead of complete organisms, as hosts to carry out the method of the invention in vivo. Suitable eukaryotic cells may be any non-human cell, but are preferably plant cells.

According to another preferred embodiment, the polypeptide or the nucleic acid used in the method of any of the embodiments above is derived from *Salvia sclarea*.

An important tool to carry out the method of the invention is the polypeptide itself. A polypeptide having a sclareol synthase activity and comprising an amino acid sequence at least 50% identical to SEQ ID NO:1 is therefore another object of the present invention.

According to a preferred embodiment, the sclareol synthase comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to another preferred embodiment, the polypeptide comprises the amino acid sequence SEQ ID NO:1. According to a more preferred embodiment, the polypeptide consists of SEQ ID NO:1.

According to another preferred embodiment of the invention, the polypeptide is derived from *Salvia sclarea*.

As used herein, the terms "sclareol synthase" or "polypeptide having a sclareol synthase activity" refers to a genus of polypeptides or peptide fragments that encompasses the amino acid sequences identified herein, as well as truncated or variant polypeptides, provided that they keep their sclareol synthase activity as defined above and that they share at least the defined percentage of identity with the corresponding fragment of SEQ ID NO:1.

According to a preferred embodiment, the sclareol synthase comprises an amino acid sequence at least 50% identical to SEQ ID NO:96. Preferably the sclareol synthase comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:96. According to another preferred embodiment, the polypeptide comprises the amino acid sequence SEQ ID NO:96. According to a more preferred embodiment, the polypeptide consists of SEQ ID NO:96.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by mutation of a nucleic acid of the invention, as described thereafter, are also encompassed by the invention.

The nucleic acid encoding the polypeptide having a sclareol synthase activity, as defined above, is a necessary tool to modify non-human organisms or cells intended to be used when the method is carried out in vivo. A nucleic acid encoding a polypeptide as defined in any of the above embodiments is therefore another object of the invention.

According to a preferred embodiment, the nucleic acid comprises a nucleotide sequence at least 50% identical to SEQ ID NO:2 or the complement thereof. According to a more preferred embodiment, said nucleic acid comprises a nucleotide sequence at least 55%, preferably at least 60%, preferably at least 65%, preferably at least 70%, preferably at least 75%, preferably at least 80%, more preferably at least 85%, more preferably at least 90%, more preferably at least 95% and even more preferably at least 98% identical to SEQ ID NO:2 or the complement thereof. According to a more preferred embodiment, the nucleic acid comprises a nucleotide sequence identical to SEQ ID NO:2 or the complement thereof. According to an even more preferred embodiment, the nucleic acid consists of SEQ ID NO:2 or the complement thereof.

According to another preferred embodiment of the invention, the nucleic acid is derived from *Salvia sclarea*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above. Particularly useful truncated nucleic acids are the nucleic acids at least 70% identical to SEQ ID NO:93 or the complement thereof.

The nucleic acids obtained by mutations of SEQ ID NO:2 or of the complement thereof are also encompassed by the invention, provided that they share at least the defined percentage of identity with the corresponding fragment of SEQ ID NO:2 and that they encode polypeptides having a sclareol synthase activity, as defined above. Mutations may be any kind of mutations of these nucleic acids, such as point mutations, deletion mutations, insertion mutations and/or frame shift mutations. Variant nucleic acids may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

According to a further preferred embodiment, the nucleic acid is a truncated nucleic acid comprising a nucleotide sequence at least 50%, preferably at least 55%, preferably at least 60%, preferably at least 70%, preferably at least 75%, preferably at least 80%, preferably at least 85%, preferably at least 90%, more preferably at least 95% and even more preferably at least 98% identical to SEQ ID NO:93 or the complement thereof. According to another preferred embodiment, the nucleic acid comprises the nucleotide sequence SEQ ID NO:93 or the complement thereof. According to a more preferred embodiment, the nucleic acid consists of SEQ ID NO:93 or the complement thereof.

Generally speaking, the nucleic acid of the invention can be isolated using a massively parallel sequencing approach, which is extensively developed in Examples 5 and 6. The first step of this method is the global sequencing of the cDNA library. The cDNA library is first fragmented by nebulization. The fragments are then amplified by PCR and the sequencing reaction is carried out. Short sequences of 35 bases named "reads" are obtained. "Reads" are reassembled in contiguous sequences ("contigs") using a software with defined minimum length of overlap and percentage of homology settings. "Reads" and "contigs" are then searched for sequence identity with known enzymes of the same type. On the basis of these homologies, "reads" and "contigs" are selected and used to synthesize primers in order to carry out the PCR amplification of the full length sclareol synthase.

Another important tool for transforming host organisms or cells suitable to carry out the method of the invention in vivo is an expression vector comprising at least one nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vectors include the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having a sclareol synthase activity, as disclosed further below.

Recombinant non-human organisms and cells transformed to harbor at least one nucleic acid of the invention, so that it heterologously expresses or over-expresses at least one polypeptide of the invention are also very useful tools to carry out the method of the invention. Such non-human organisms and cells are therefore another object of the present invention.

Non-human organisms of the invention may be any non-human multicellular or unicellular organisms. In a preferred embodiment, the non-human organism of the invention is a plant, a prokaryote or a fungus. Said organism may be any plant, prokaryote or fungus. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*. In a more preferred embodiment the non-human organism is a microorganism.

According to an even more preferred embodiment said microorganism is a bacteria or yeast and most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of any of the nucleic acids of the invention. Preferably the term "transformed" relates to hosts heterologously expressing the polypeptides of the invention, as well as over-expressing them. Accordingly, in an embodiment, the present invention provides a transformed organism, in which the polypeptide of the invention is expressed in higher quantity than in the same organism not so transformed.

There are several methods known in the art for the creation of transgenic host organisms or cells such as plants, fungi, prokaryotes, or cell cultures of higher eukaryotic organisms. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. Gene 61: 1-11, 1987.

Methods for transforming host organisms or cells to harbor transgenic nucleic acids, such as those of the present invention, are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant systems results. Any chromosomal integration method known in the art may be used in the practice of the invention, including but not limited to, recombinase-mediated cassette exchange (RMCE), viral site-specific chromosomal insertion, adenovirus, and pronuclear injection.

In order to carry out the method for producing sclareol in vitro, as exposed herein above, it is very advantageous to provide a method of making at least one polypeptide having a sclareol synthase activity. Therefore, the invention provides a method for producing at least one polypeptide having a sclareol synthase activity comprising
a) culturing a non-human organism or cell transformed with the expression vector of the invention, so that it harbors a nucleic acid according to the invention and expresses or over-expresses a polypeptide encoded by said nucleic acid and having a sclareol synthase activity;
b) isolating the polypeptide having a sclareol synthase activity from the non-human organism or cell cultured in step a).

According to a preferred embodiment, said method further comprises, prior to step a), transforming a non-human host organism or cell with at least one expression vector of the invention, so that it harbors at least one nucleic acid according to the invention and expresses or over-expresses at least one polypeptide encoded by said nucleic acid.

Transforming and culturing of the non-human organism or cell can be carried out as described above for the method of producing sclareol in vivo. Step b) may be performed using any technique well known in the art to isolate a particular polypeptide from an organism or cell.

A "polypeptide variant" as referred to herein means a polypeptide having a sclareol synthase activity and being substantially homologous to a native polypeptide, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc), or an improved expression level in a desired expression system. A variant or site directed mutant may be made by any method known in the art. As stated above, the invention provides recombinant and non-recombinant, isolated and purified polypeptides, such as from *Salvia sclarea*. Variants and derivatives of native polypeptides can be obtained by isolating naturally-occurring variants, or the nucleotide sequence of variants, of other or same plant lines or species, or by artificially programming mutations of nucleotide sequences coding for native sclareol synthases. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides.

Therefore, in an embodiment, the present invention provides a method for preparing a variant polypeptide having a sclareol synthase activity and comprising the steps of:
(a) selecting a nucleic acid according to any of the embodiments exposed above;
(b) modifying the selected nucleic acid to obtain at least one mutant nucleic acid;
(c) transforming host cells or unicellular organisms with the mutant nucleic acid sequence to express a polypeptide encoded by the mutant nucleic acid sequence;
(d) screening the polypeptide for at least one modified property; and,
(e) optionally, if the polypeptide has no desired variant sclareol synthase activity, repeat the process steps (a) to (d) until a polypeptide with a desired variant sclareol synthase activity is obtained;
(f) optionally, if a polypeptide having a desired variant sclareol synthase activity was identified in step d), isolating the corresponding mutant nucleic acid obtained in step (c).

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein to predetermined codons can be altered by substitution, deletion or insertion.

Accordingly, SEQ ID NO:2 or 93 may be recombined with any other diterpene synthase encoding nucleic acids, for example isolated from an organism other than *Salvia sclarea*. Thus, mutant nucleic acids may be obtained and separated, which may be used for transforming a host cells according to standard procedures, for example such as disclosed in the present Examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present Examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

In an embodiment, the present invention provides a method for preparing a nucleic acid encoding a variant polypeptide having a sclareol synthase activity, the method comprising the steps (a)-(e) disclosed above and further comprising the step of:

All the publications mentioned in this application are incorporated by reference to disclose and describe the methods and/or materials in connection with which the publications are cited.

DESCRIPTION OF THE DRAWINGS

Figure 4B:
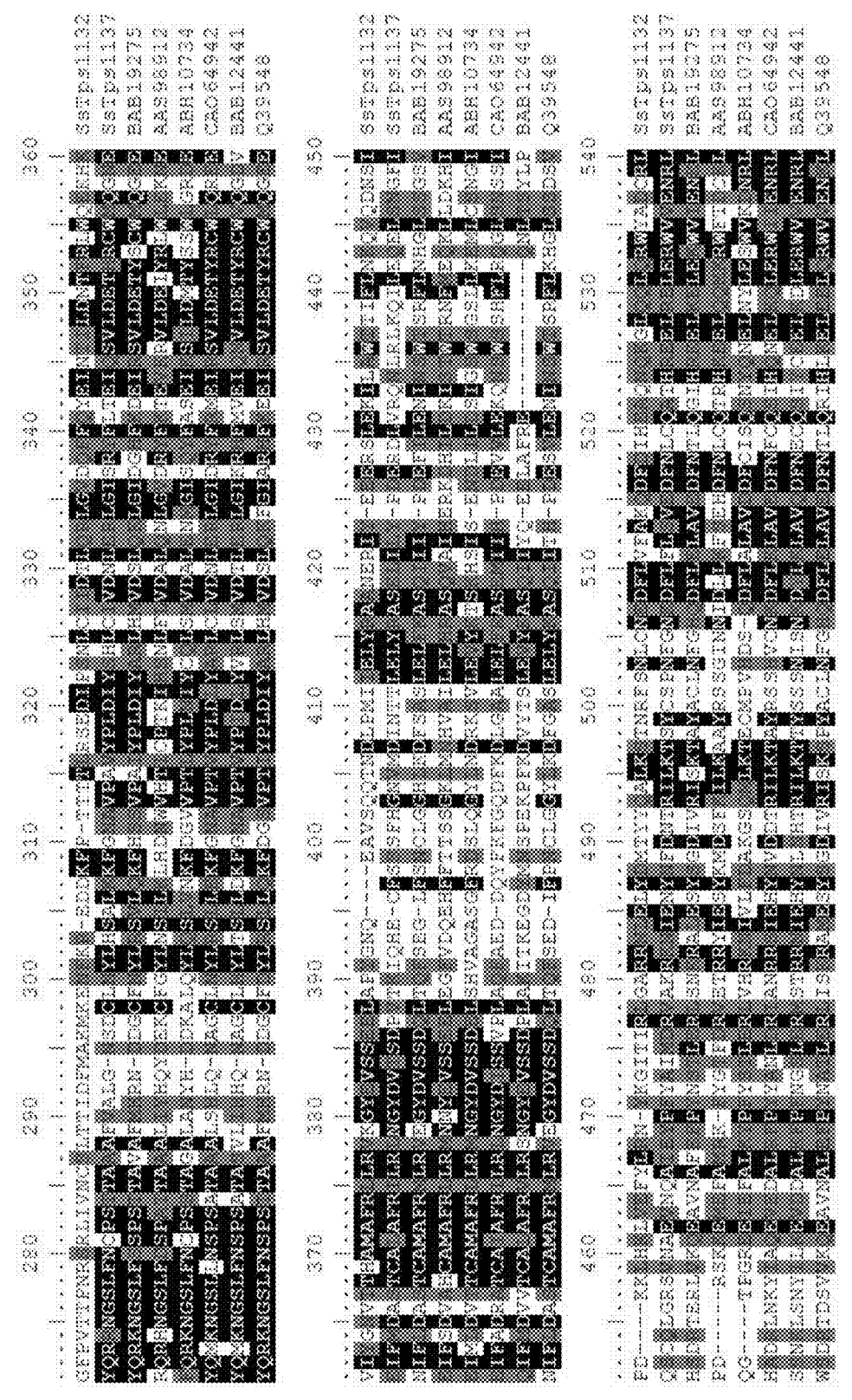

FIGS. 4A-4D: Alignment of the amino acid sequence deduced from SsTps1132 (SEQ ID NO:1) and SsTps1137 (SEQ ID NO:86) with diterpene synthases amino acid sequences BAB19275 (SEQ ID NO:106), AAS98912 (SEQ ID NO:107), ABH10734 (SEQ ID NO:108), CAO64942 (SEQ ID NO:109), BAB12441 (SEQ ID NO:110), and Q39548 (SEQ ID NO:111) selected from the database.

SPECIFIC EMBODIMENTS OF THE INVENTION OR EXAMPLES

Figure 1:
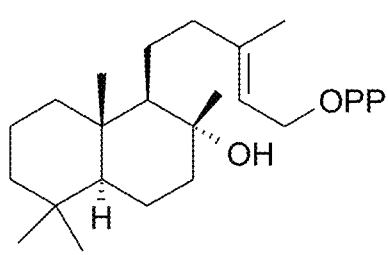
FIG. 1: Structures of the diverse compounds cited in the description.
Figure 1:
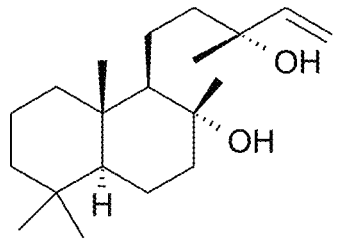
Figure 1:
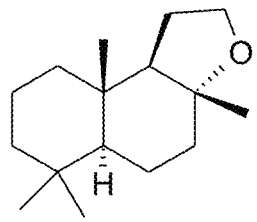
Figure 1:
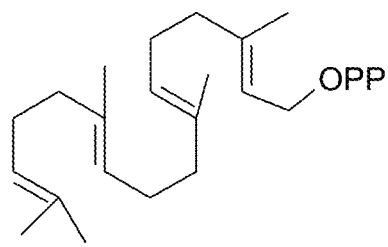
Figure 1:
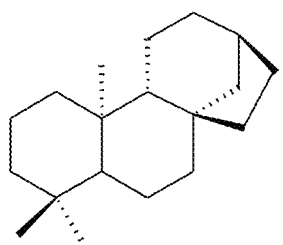
Figure 1:
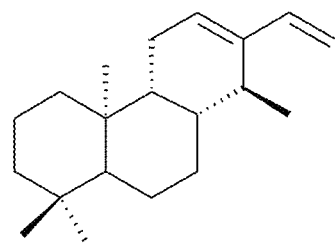
Figure 2:
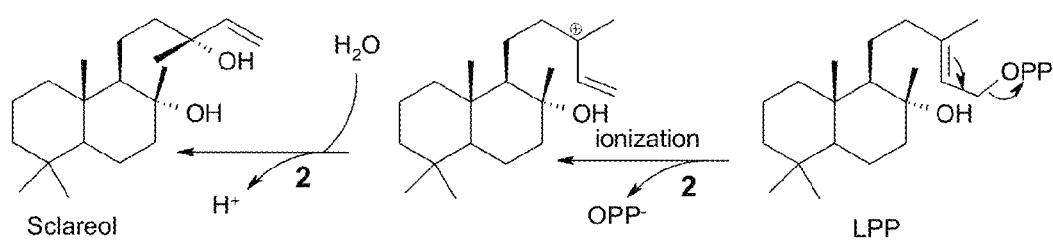
FIG. 2: Putative biosynthesis of sclareol from LPP, which is catalyzed by the SsTps1132 (SEQ ID NO:1).

The invention will now be described in further detail by way of the following Examples.

Example 1

Isolation of LPP Synthase Encoding cDNAs from *Salvia sclarea* by a PCR Approach A. Plant Material and RNA Extraction.

*Salvia sclarea* developing flower buds (1.5 to 2 cm length, 1-2 days old) were collected in fields of Bassins (Switzerland) and directly frozen in liquid nitrogen.

Total RNA was extracted using the Concert™ Plant RNA Reagent from Invitrogen (Carlsbad, Calif.) and the mRNA was purified by oligodT-cellulose affinity chromatography using the FastTrack® 2.0 mRNA isolation Kit (Invitrogen, Carlsbad, Calif.) according to the manufacturer's instructions. A cDNA library was constructed using the Marathon™ cDNA Amplification Kit (Clontech, Mountain View, Calif.).

B. Polymerase Chain Reactions for Amplification of Diterpene Synthases cDNAs

PCR were performed using the forward primer DT3F (5'-GAYRTNGAYGAYACNGCNATGG-3' (SEQ ID NO:3)) and the reverse primer DT4R (5'-GTYTTNCCNAKC-CANACRTCRYYT-3' (SEQ ID NO:4)). The PCR mixture contained 0.4 µM of each primer, 300 µM each dNTPs, 5 µL of 10× HotStartTaq® DNA polymerase buffer (Qiagen), 2 µL of 100 fold diluted cDNA, 0.5 µL of HotStartTaq® DNA polymerase in a final volume of 50 µL. The cycling conditions were: 35 cycles of 45 sec at 94° C., 45 sec at 50° C. and 2 min at 72° C.; and 10 min at 72° C. The sizes of the PCR products were evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen, Carlsbad, Calif.). Inserted cDNAs fragments were then subject to DNA sequencing and the sequence was compared against the GenBank non-redundant protein database (NCBI) using the BLASTX algorithm (Altschul et al, *J. Mol. Biol.* 215, 403-410, 1990). A 354 bp sequence named FN23 (SEQ ID NO:5) was obtained. This DNA fragment possessed the expected size and showed sequence homology to diterpene synthases.

C. Full Length cDNA Isolation by Rapid Amplification of cDNA Ends (RACE).

Oligonucleotides specific for the FN23 sequence (SEQ ID NO:5) were designed: FN23-F1 (3'-GCACGGATAC-GACGTCGATCCAAATGTAC-5' (SEQ ID NO:6)), FN23-F2 (3'-GGGCTGCTCAACTAAGATTTCCAGGAG-5' (SEQ ID NO:7)) and FN23-F3 (5'-GGGTGATATCCGAC-CACTTATTTGATGAG-5' (SEQ ID NO:8)). These primers were used in RT-PCR in combination with oligodT primers extended with an adaptor sequence (5'-AATTCGGTAC-CCGGGATCC(T)$_{17}$-3') (SEQ ID NO:9). The composition of the RT-PCR reaction mixture was the following: 10 µl 5× Qiagen OneStep RT-PCR buffer, 400 µM each dNTP, 400 nM each primer, 2 µl Qiagen OneStep RT-PCR Enzyme Mix, 1 µl RNasin® Ribonuclease Inhibitor (Promega Co., Madison, Wis.) and 1250 ng total RNA in a final volume of 50 ml. The thermal cycler conditions were: 30 min at 50° C. (reverse transcription); 15 min at 95° C. (DNA polymerase activation); 35 cycles of 45 sec at 94° C., 45 sec at 50° C. and 90 sec at 72° C.; and 10 min at 72° C. A second round of PCR was performed using the RT-PCR products as template with the adapterP primer (5'-AATTCGGTACCCGGGATCC-3' (SEQ ID NO:10)) in combination with the same or nested FN23-specific primers. This PCR approach provided a 1271 bp cDNA fragment (FN30 (SEQ ID NO:11)) having a 192 bp perfect overlap with the FN23 fragment (SEQ ID NO:5) and containing the 3' end including the stop codon and the 3' non-coding sequence of the corresponding cDNA.

For amplification of the 5' end of the cDNA, anti-sense oligonucleotides specific for FN23 were designed: FN23-R1 (5'-CATGGCATCTTCAACCCCAGCTTTATCTCATC-3' (SEQ ID NO:12)), FN23-R2 (5'-GTGGTCGGATATCAC-CCATCTTTCTTGAAGTCG-3' (SEQ ID NO:13)), FN23-R3 (5'-CATTGGAGATGCAGACTCGACCGATTGACC-3' (SEQ ID NO:14)). These primers were used for 5'RACE using the *S. sclarea* cDNA library following the Marathon™ cDNA Amplification Kit protocol (Clontech, Mountain View, Calif.). The thermal Cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C. This 5'RACE provided a 1449 bp cDNA fragment (FN40 (SEQ ID NO:15)) having a 227 bp perfect overlap with FN23 (SEQ ID NO:5). Comparison with known diterpene synthases sequences revealed that the FN40 fragment (SEQ ID NO:15) contained the translation initiation codon and a 87 bp non-coding region. The assembling of the three cDNA fragments (FN23, FN30 and FN40 (SEQ ID NO:5, 11 and 15) provided a full length cDNA sequence (SaTps1) of 2655 bp (SEQ ID NO:16) with an open reading frame of 2355 bp coding for a 785 residues protein (SEQ ID NO:17).

Example 2

Heterologous Expression of the *S. sclarea* LPP Synthase in *E. coli*

The pETDuet-1 (Novagen, Madison, Wis.), designed for expression under the control of a T7 promoter, was used for expression in *E. coli* cells. To construct the expression plasmid, the open reading frame of SaTps1 (SEQ ID NO:16) was amplified by PCR from the cDNA library with the forward and reverse primers SaTps-Nde (3'-TACTGACATATGACT-TCTGTAAATTTGAGCAGAGCACC-5' (SEQ ID NO:18)) and SaTps-Kpn (3'-TTGGTACCTCATACAACCGGTC-GAAAGAGTACTTTG-5' (SEQ ID NO:19)) designed to introduce an NdeI site immediately before the start codon and a KpnI site after the stop codon. Since the open reading frame contains an NdeI site at position of 1614 of the open reading frame, this amplification was performed in two steps by overlap extension PCR (Horton et al, Gene 77, 61-68, 1989), using the primers SaTps-Nde (SEQ ID NO:18) and SaTps-Kpn (SEQ ID NO:19) in combination with the primers Satps-mut1f (5'-GTTGGAGTGGATCCACATGCAGGAATGG-TAC-3' (SEQ ID NO:20)) and Satps-mut1r (3'-GTACCAT-TCCTGCATCTGGATCCACTCCAAC-5' (SEQ ID NO:21)), designed to remove the NdeI site without altering the amino acid sequence. The resulting cDNA were first ligated in the PCR2.1-Topo plasmid using the TOPO TA Cloning Kit (Invitrogen, Carlsbad, Calif.) and the sequences of the inserts were verified prior to sub-cloning as NdeI-KpnI fragment into the pETDuet-1 vector. Analysis of the sequence of several clones obtained by amplification from the cDNA library with the SaTps1 specific primers showed some variability in several positions of the cDNA sequence. Seven positions were identified, in which two different amino acids can be found. One position was found were insertion of a serine residue occurred in some of the clones. These positions are listed in the table below.

| Positions (relative to the aminoacid sequence) | Amino acid |
| --- | --- |
| 34 | Ile or Thr |
| 40 | Phe or Leu |
| 174 | Gln or His |
| 222 | Gly or Asp |
| 538 | Gln or His |
| 560 | Arg or Leu |
| 596 | Asn or Lys |
| 612 | Insertion of a Ser |

These variations seemed to occur in a random manner in eleven different clones sequenced, suggesting that at least two very closely related isoforms of a diterpene synthase are present in the *S. sclarea* genome and that the PCR amplification approach leaded to shuffling of the sequences. Two clones, SsLPPs3 (SEQ ID NO:22) and SsLPPs9 (SEQ ID NO:23) representative of the sequences variability, were selected for the heterologous expression and enzyme characterization experiments.

The plasmids pETDuet-SsLPPs3 and pETDuet-SsLPPs9 were transferred into B121(DE3) *E. Coli* cells (Novagen, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments.

The crude protein extracts from pETDuet-SsLPPs3 and pETDuet-SsLPPs9 transformed cells were analyzed by SDS- PAGE and compared to protein extracts obtained from cells transformed with the empty pETDuet plasmid. The recombinant SsLPPs3 and SsLPPs9 proteins (SEQ ID NO:24 and 25) were clearly detected and the apparent molecular weight estimated at 90 KDa, a value in concordance with the calculated molecular weight of 83 KDa.

Example 3

Purification of the LPP Synthase from *Salvia sclarea* and Enzymatic Activities

The PCR2.1-Topo plasmids containing the SsLPPs3 and SsLPPs9 cDNA (SEQ ID NO:22 and 23) (Example 2) were digested with NdeI and SacI and the inserts were ligated into the pET28a(+) plasmid (Novagen). The resulting expression plasmids (pET28-SsLPPs3 and pET28-SsLPPs9) contain the cDNAs with a 5'-end modification designed to express the proteins with an N-terminal hexa-histidine tag (His-tag). Purification was performed under native conditions using the ProBond™ Purification System (Invitrogen) following the manufacturer protocol excepted that, for the elution, imidazole was replaced by L-histidine to minimize inhibition of the enzyme. Using this approach, the SsLPPs3 and SsLPPs9 "His-tag" recombinant enzymes (SEQ ID NO:97 and 98) could be purified to apparent homogeneity.

The affinity purified enzymes were incubated 12 hours at 30° C. with 200 μM GGPP and 1 mM DTT in MOPSO pH 7, 10% glycerol, 1 mM DTT. No diterpene product was observed by extracting the incubation medium with pentane and analysis of the extract by GC or GC-MS. Treatment of the same extract by alkaline phosphatase (Sigma, 6 units/ml), followed by extraction with pentane and GC analysis, showed the formation of labdenediol and demonstrated the enzymatic formation of labdenediol-diphosphate (LPP) as unique product from GGPP by the recombinant diterpene synthase. The GC analysis was performed on an Agilent 6890 Series GC system equipped with a flame ionization detector using a 0.25 mm inner diameter by 30 m SPB-1 capillary column (Supelco, Bellefonte, Pa.). The carrier gas was He at a constant flow of 1.5 mL/min. The initial oven temperature was 100° C. (1 min hold) followed by a gradient of 10° C./min to 300° C. The GC-MS analysis was performed in the same conditions and the spectra were recorded on an Agilent 5975 mass detector.

Example 4

PCR Approach for the Homology Cloning of Class I Diterpene Synthases (Sclareol Synthase) from *S. sclarea*

The cloning and characterization of SsLPPs3 (SEQ ID NO:24) and SsLPPs9 (SEQ ID NO:25), in Examples 1 to 3, suggest that the biosynthesis of sclareol in *S. sclarea* involves two proteins, the SsLPPs and a class I diterpene synthase, the sclareol synthase, catalyzing the conversion of LPP to sclareol.

A PCR approach was used in a first attempt for the isolation of class I diterpene synthases cDNA sequences. Oligonucleotides were designed based on conserved sequences in plant diterpene synthases and especially in diterpene synthases catalyzing the cyclization of $C_{20}$-diphosphate esters via an ionization mechanism. The sequences with accession numbers BAB19275, AAB39482, AAD30231, AAD34295, CAE05201, BAB12441, AAT49066, CAE05199, AAU05906, BAD17672, AAQ72565, AAL09965, AAK83563, AAS47691, AAS47690 and AAR13860, were selected from the National Center for Biotechnology Information online public sequence databases. All these protein sequences correspond to class I diterpene synthases and contain the DDxxD motif (wherein x represents any amino acid) characteristic of ionization-dependent cyclization mechanism in terpene synthases. From the alignment of these sequences, two conserved motifs were first selected in the N-terminal region and used for the design of sense oligonucleotides: YDT(A/S)WVA and (D/N)GSWG. In the amino acid sequence of the SsLPPs (SEQ ID NO:24 and 25, Examples 1 to 3) these two motifs were also conserved, though with some differences for the first motif (YDTAVIA). Thus the sequence of SsLPPs was also taken into account for the design of the sense oligonucleotides. From the first motif, three oligonucleotides were design to cover all the sequences variations: DiTpsTB_F1, 5'-TATGATACNGCNGT-NATDGC-3' (SEQ ID NO:26); DiTpsTB_F2, 5'-TATGA-CACGGCAGTGATCGC-3' (SEQ ID NO:27); DiTpsTB_F3, 3'-TATGACACGGCAKKGRTNGC-5' (SEQ ID NO:28). From the second motif, two oligonucleotides were designed: DiTpsTB_F4, 5'-CAACTGGCTGATGGNTCNTGGGG-3' (SEQ ID NO:29); DiTpsTB_F5, 5'-CAACTGGCTGATG-GCTCATGGGG-3' (SEQ ID NO:30). The DDxxD motif, located in the C-terminal region of the proteins and involved in the binding of the diphosphate moiety in the active site, was used to design two anti-sense oligonucleotides: DiTpsTB_R1, 5'-GATCCTCCAACRTCRWARARRTCRTC-3' (SEQ ID NO:31), DiTpsTB_R2, 5'-GATCCTCCACGTCG-WAGAAGTCGTC-3' (SEQ ID NO:32).

These primers were used for PCR amplification from a *Salvia sclarea* cDNA library (prepared as described in Example 1). The PCRs were performed using the Advantage® 2 Polymerase Mix (Clontech). Each PCR mixture contained, in total volume of 50 μL, 5 μL of Advantage® 2 PCR Buffer, 200 μM dNTPs, 200 nM each oligonucleotide primer, 5 of 200 fold diluted cDNA, 1 μL of Advantage® 2 Polymerase Mix. The following conditions were used for the amplifications: 3 minutes of denaturation at 94° C.; 15 cycles of 1 minutes denaturation at 94° C., 1 min of annealing at 65° C. for the first cycle and minus one degree for each following cycle, and 2 minutes extension at 72° C.; 20 cycles of 1 minutes denaturation at 94° C., 1 min of annealing at 58° C. and 2 minutes extension at 72° C.; and finally 10 minutes extension at 72° C. Different PCR were performed with the possible combinations of sense and anti-sense oligonucleotides. The amplicons were screened for the expected sizes and for sequence homology to diterpene synthases. Unfortunately, using this PCR approach, no diterpene-related sequence could be obtained.

Example 5

Massively Parallel Sequencing of a *S. sclarea* Flower cDNA Library

Since the classical homology-based cloning approach did not succeed in the cloning of class I diterpene synthase from *S. sclarea*, we undertook to use an approach based on the global sequencing of the cDNA library. We used the technology of massive parallel sequencing of small DNA fragments developed by Illumina (San Diego, Calif.) to obtain sequence information of all the transcripts (transcriptome) present in the *Salvia sclarea* flowers. This sequencing technique uses a reversible terminator-based sequencing chemistry and the Cluster Station and Genome Sequencer apparatuses developed by Solexa and Illumina.

The technology and equipment was set up at Fasteris SA (Geneva, Switzerland) and the preparation of the DNA samples and the sequencing were performed by Fasteris SA. An aliquot (1 µg) of the cDNA library generated from *S. sclarea* developing flowers and using the Marathon™ cDNA Amplification Kit (Clontech, Mountain View, Calif.) (Example 1), was treated using the Genomic Sample Prep Kit (Illumina). Briefly, the DNA is fragmented by nebulization, the ends are repaired to generate blunt ends, adapters are ligated to the ends of the DNA fragments and the adapter-modified DNA fragments are amplified by PCR. After controlling the quality of the library by gel electrophoresis, the generation of the DNA clusters on the flow cell and the sequencing reaction is performed on the Cluster Station and Genome Sequencer equipments. Using this technology, 1.9 millions of short sequences (reads) of 35 bases were obtained.

The Edena software (Dr David Hernandez, Genomic Research Laboratory, University of Geneva Hospitals, Geneva, Switzerland) was used to reassemble contiguous sequences. The five last bases were first removed from each read because of possible miss-incorporations due to the lower fidelity in the last cycles of the sequencing procedure. The parameters of the software were set such as to allow 15 bases minimum length for the overlaps with strict (100%) identity. The contigs (contiguous sequences) with a length of at least 50 bases were retained. In these conditions, 2054 contigs of 50 to 1330 bases in length could be reconstituted.

To evaluate the quality of the assembling, the contigs were searched for sequence identity with the DNA sequence of SsLPPs, the class II diterpene synthases first isolated from the *S. sclarea* cDNA library (SsLPPs3 (SEQ ID NO:22), Example 2). This search was performed using the BLASTn method (Altschul et al, *J. Mol. Biol.* 215, 403-410, 1990). Surprisingly, only 3 contigs of lengths of 81, 73 and 52 bases were found and only forty reads had been used by the Eland software to generate these contigs. Alignment with the SsLPPs3 reference sequence showed that the 3 contigs (SEQ ID NO:33 to 35 covered only 8.7% of the full-length sequence although with an identity of 99%).

Very limited sequence information has been reported in the public databases for *Salvia sclarea*. The only gene sequence available from the NCBI database was the sequence of the large subunit of the ribulose-1,5-bisphosphate carboxylase (RuBisCO) from *salvia sclarea* (NCBI access No. Z37450). Search of the contigs for DNA identity with this *S. sclarea* RuBisCO DNA sequence (BLASTn Search) provided two contigs of 870 and 547 bases respectively (SEQ ID NO:36 and 37). Alignment of the two contigs with the RuBisCO sequence showed coverage of 98%: only 27 bases (between position 858 and 884) out of 1420 bases were not present in the contigs. In addition to this almost complete coverage, the identity between the reference sequence and the contigs was 99.5%, representing a difference of only 7 nucleotides.

All reads (non-assembled data) were then searched for sequence identity with the SsLPPs3 sequence (SEQ ID NO:22). The Eland software (Illumina) was used to perform this search allowing a maximum of 2 mismatches with the reference sequence. A total of 616 reads where recovered. Alignment of the selected fragments with the reference sequence revealed that the SsLPPs3 sequence (SEQ ID NO:22) was covered on the whole length with a slightly higher coverage (more reads) towards the 3' end. The same manipulation with the RuBisCO sequence showed that 1650 reads were obtained for this sequence. The coverage of the reference sequence with the reads was much higher for the RuBisCo than for SsLPPs3 (SEQ ID NO:22). For SsLPPs3 (SEQ ID NO:22), several small regions with no coverage and regions with sequence ambiguity between reads were found. This incomplete coverage prevents the complete re-assembling and is certainly the reason for the generation of only a few very small contigs.

The number of reads obtained for a given cDNA is proportional to the abundance of this cDNA. Thus, relative abundances can be estimated by dividing the number of reads obtained for given cDNAs by their total lengths. Performing this calculation for the RuBisCO and SsLPPs3 (SEQ ID NO:22) gave values of 1160 and 260 reads/Kb respectively, reflecting a 4.5 higher abundance of the RuBisCO cDNA relative to the SsLPPs cDNAs. The RubisCo is an enzyme involved in the primary metabolism of plants and catalyzing the fixation of carbon in the Calvin cycle. The higher relative abundances of the RuBisCO reflects a high representation of genes involved in primary metabolisms compared to gene involved in secondary metabolism such as diterpene synthesis. BLAST search analysis with the contigs showed that other enzymes from the Calvin cycles (e.g. phosphoglycerate kinase, glyceraldehyde 3-phosphate dehydrogenase, triose-phosphate isomerase) and primary metabolism were also abundantly represented in the cDNA library used herein. Thus, the cDNA coding for the enzymes involved in secondary metabolism and particularly in diterpene biosynthesis were in too low abundance to obtain a sufficient coverage and complete reassembling.

Example 6

Extraction of Class I Diterpene Synthases-like Sequences from the Sequencing Data The Blast algorithm (Altschul et al, *J. Mol. Biol.* 215, 403-410, 1990) was used to search for homology of the deduced amino acid sequences with class I diterpene synthases sequences.

A Blastx search against a protein database was first performed with the 2054 contigs. This search provided only one contig (contig1610, SEQ ID NO:38) presenting sequence to homology with class I diterpene synthases. The amino acid sequence deduced from this contig contained the DDxxD motif characteristic of ionization-initiated cyclization of prenyl-diphosphates.

A fraction of the row data, representing approximately $3 \times 10^5$ reads was then search for homology with class I diterpene synthases. The reads were search using the tBlastn algorithm with five selected class I diterpene synthase amino acid sequences (NCBI accession numbers AAC39443, BAB19275, BAB12441, AAD34295, AAS98912). This search selected 462 reads, which were then processes using the CAP program (Huang, Genomics 14(1), 18-25, 1992) to identify overlapping sequences. A small portion of the reads could be assembled in short contigs of maximum length of 111 bases. These contigs as well as the remaining isolated reads were used for Blastx search against a protein database to confirm their identity with class I diterpene synthases. Finally, 5 DNA fragments were retained (SEQ ID NO:39 to 43).

Figure 3A:
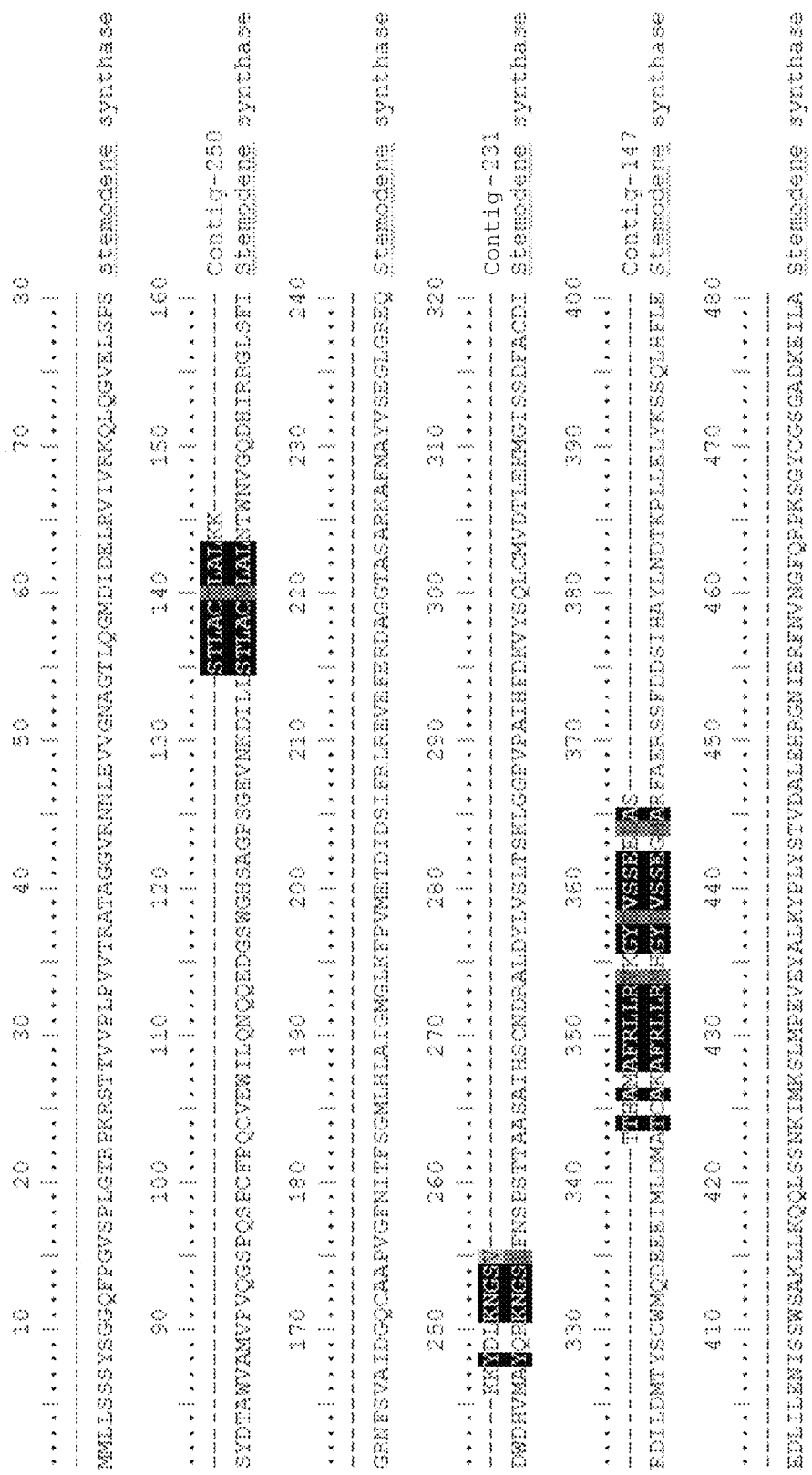
FIGS. 3A-3B: Alignment of amino acid sequences from the class I diterpene to synthase-like fragments Contig-250 (SEQ ID NO:44), Contig-231 (SEQ ID NO:45), Contig-147 (SEQ ID NO:46), Contig-33 (SEQ ID NO:47), Contig-1610-fox2 (SEQ ID NO:104), and Contig-224 (SEQ ID NO:48), with the sequence of the stemodene synthase from *Oriza sativa* (SEQ ID NO:99, Access. No. AAZ76733).
Figure 3B:
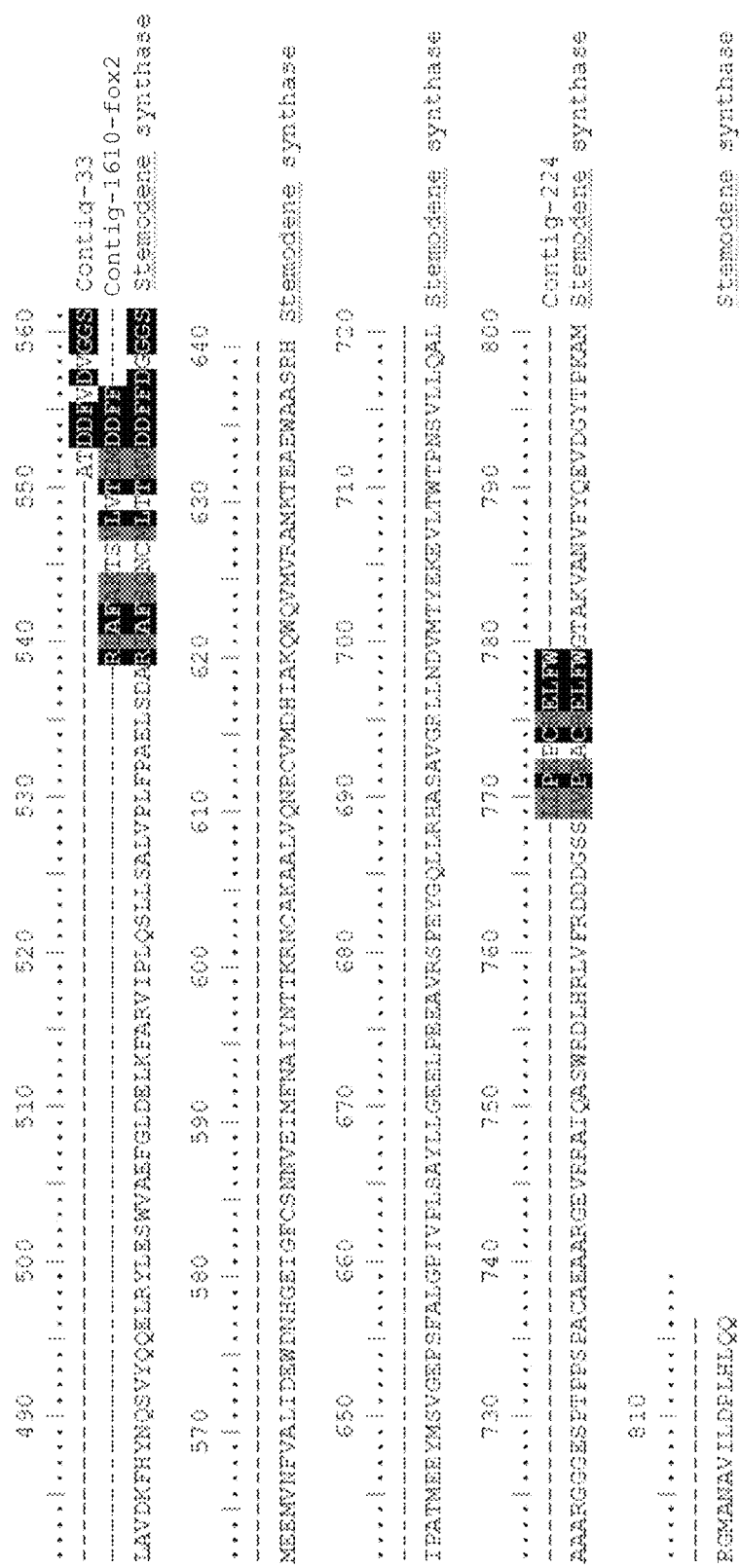
Figure 4A:
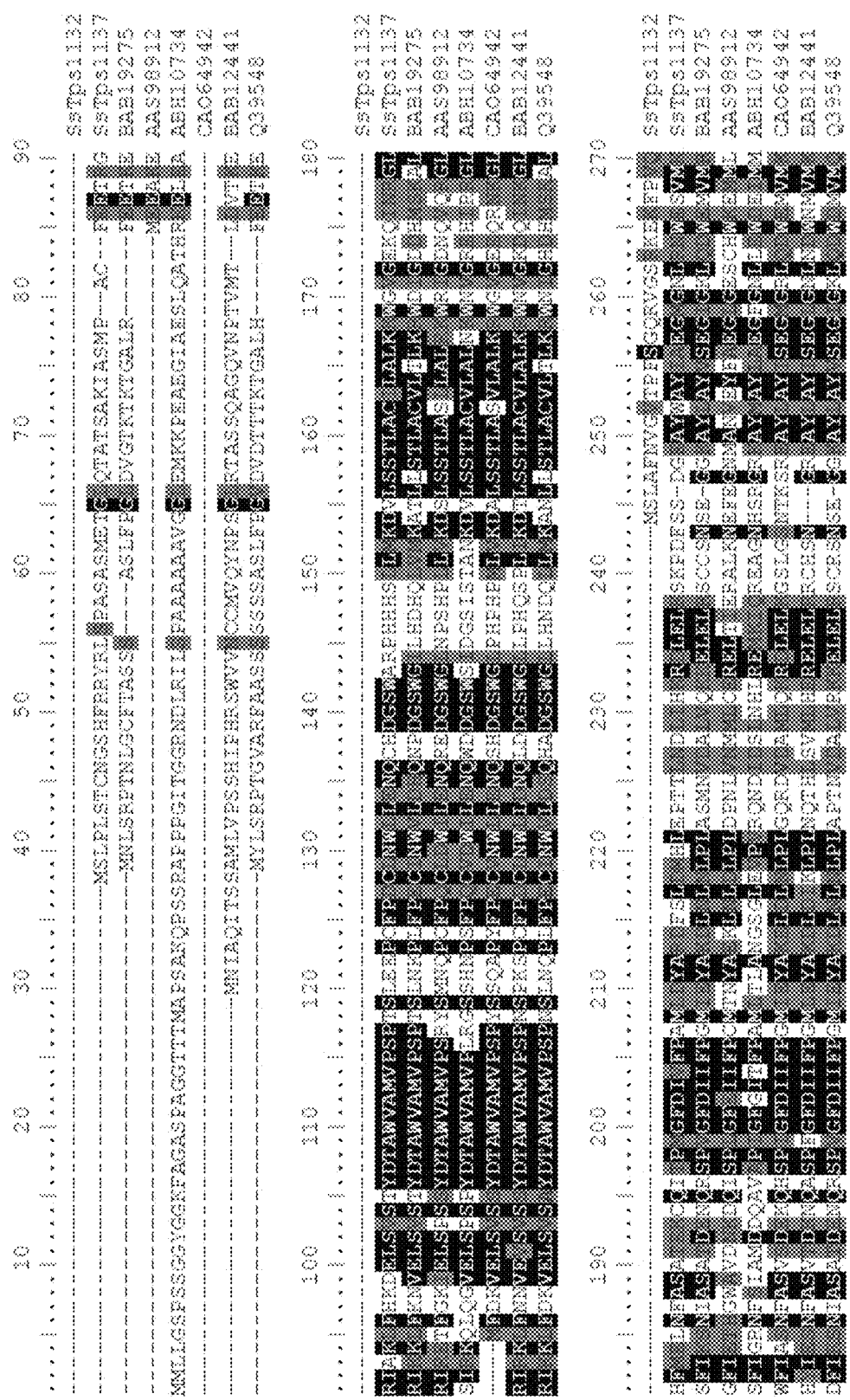
Figure 4C:
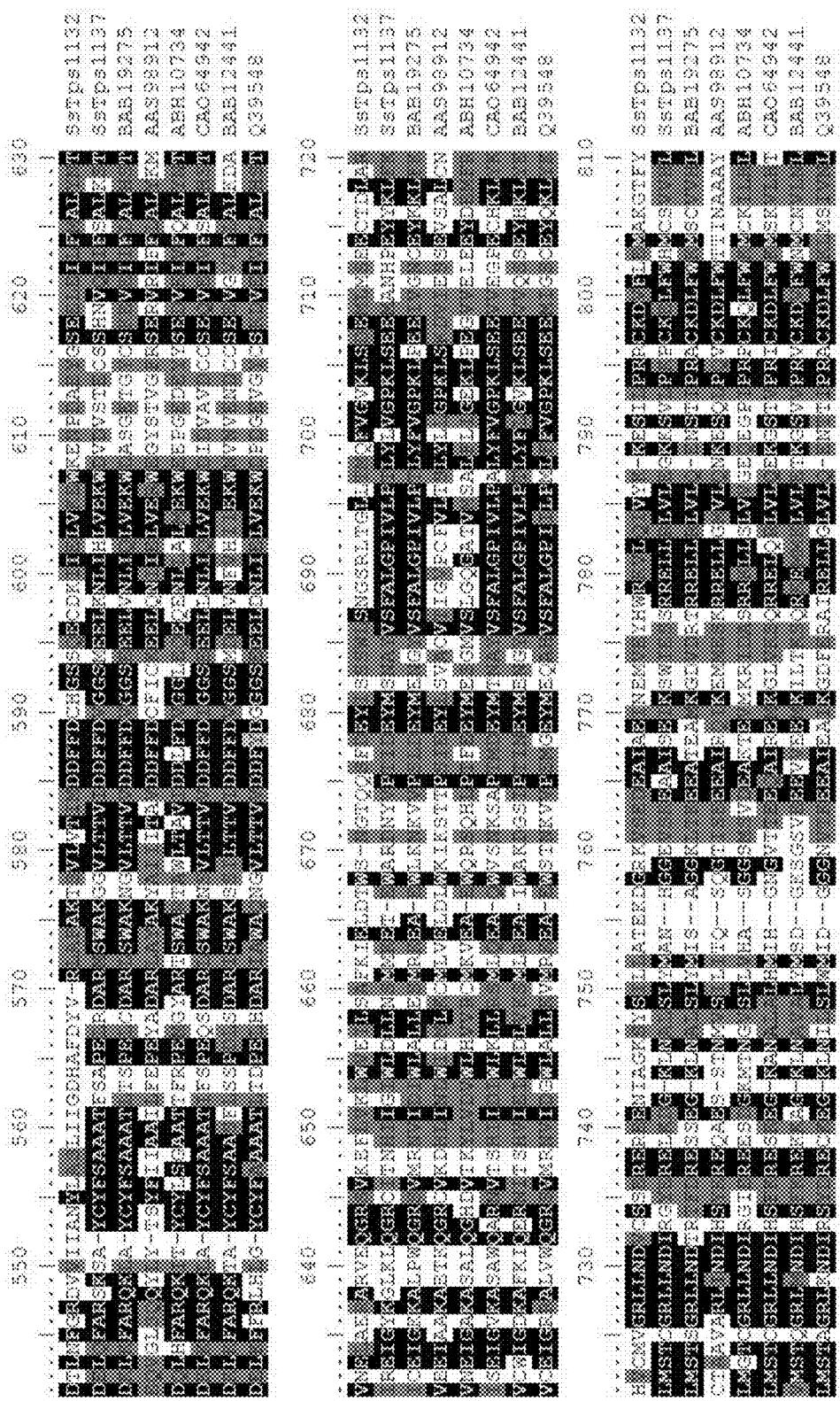
Figure 4D:
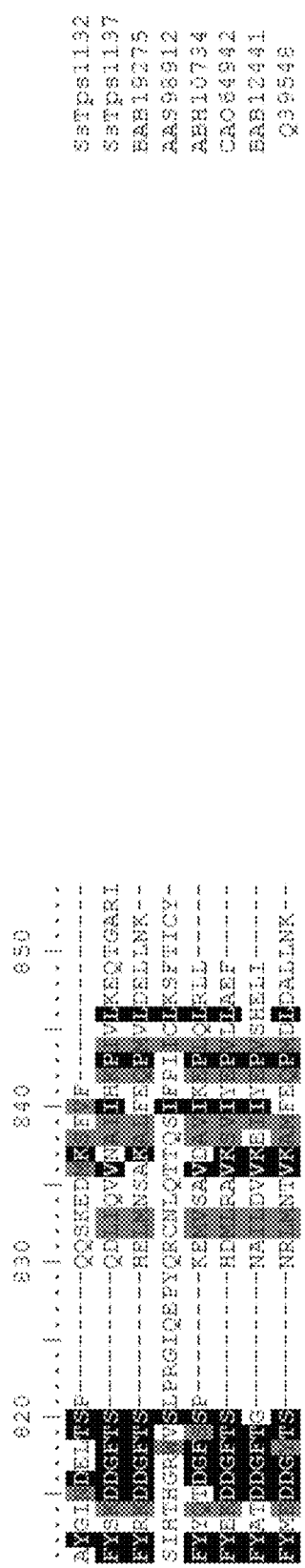

The amino acid sequences were deduced from the selected fragments (SEQ ID NO:44 to 48, and SEQ ID NO:104) and were aligned with references diterpene synthases sequences, allowing their relative positioning. FIGS. 3A-3B show an alignment of these sequences with a full-length diterpene synthase sequence, the stemodene synthase from *Oriza sativa* (Morrone et al, 2006; NCBI access No. AAZ76733) taken as reference.

Example 7

PCR Amplification of Full-length Class I Diterpene Synthases cDNAs

A set of forward and reverse oligonucleotides was deduced from the diterpene synthases-related DNA sequences selected from the sequencing of the *S. sclarea* cDNA library (Example 6). These primers were used in combination with cDNA adaptor primers in 3'/5'RACE type PCR amplifications. The amplifications were performed using the *S. sclarea* cDNA library, prepared as described above in Example 1, following the Marathon™ cDNA Amplification Kit protocol (Clontech, Mountain View, Calif.). The thermal Cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C.

Using the Cont250-Fwd primer (SEQ ID NO:49) a 547 bp DNA sequence (1130Cont250, SEQ ID NO:81) was obtained. Analysis of the sequence revealed that it corresponded to the 5' end of a diterpene synthase cDNA and contained 348 bp of the coding region. With the primer Cont147_fw1 (SEQ ID NO:51) and Cont147_fw2 (SEQ ID NO:52) we obtained a 1473 bp sequence (1132Cont147, SEQ ID NO:82) containing the 3' end and 1293 bp of the coding region of a diterpene synthase cDNA. The Cont224_fw primer (SEQ ID NO:57) provided a 207 bp DNA fragment (1137Cont224, SEQ ID NO:83) encoding for the 43 C-terminal amino acids of a diterpene synthases with a sequence distinct from 1132Cont147 (SEQ ID NO:82). The Cont147_rev1 (SEQ ID NO:53) and Cont147_rev2 (SEQ ID NO:54) primers allowed the amplification of a 464 bp DNA fragment (1134Cont147, SEQ ID NO:84). The deduced amino acid showed homology with diterpene synthases but alignment with other diterpene synthases sequences suggested that 200 to 300 codons where still missing to reach the 5' end. All the sequences obtained by this series of amplification differed significantly from the sequences of SsLPPs previously isolated (SEQ ID NO:22 and 23). PCR with the other primers deduced from the diterpene synthases-related DNA sequences (primers cont224-rev (SEQ ID NO:58), cont250-rev (SEQ ID NO:50), cont33-fw1 (SEQ ID NO:55) and cont33-rev (SEQ ID NO:56)) did not provide diterpene synthase related sequences.

From the only sequence containing an obvious translation initiation region of a diterpene synthase (1130Cont250, SEQ ID NO:81), sense oligonucleotides were deduced from the 5' untranslated region (UTR) (1130-fw1 (SEQ ID NO:59) and 1130-fw2 (SEQ ID NO:60) and from the 5' end of the open reading frame (ORF) (1130-fw3, SEQ ID NO:61). From the two sequences containing the stop codon region of two distinct diterpene synthases (1132Cont147 (SEQ ID NO:82) and 1137Cont224 (SEQ ID NO:83)), reverse-sense primers were deduced either from the 3' UTR (1132-rev1 (SEQ ID NO:65) and 1137-rev1 (SEQ ID NO:62)) or from the 3' end of the open reading frame (1132-rev2 (SEQ ID NO:64) and 1137-rev2 (SEQ ID NO:63)). PCR were performed with different to combinations of these forward and reverse primers. The combination of primers deduced from the 1130Cont250 (SEQ ID NO:81) sequence with the primers deduced from the 1137Cont224 (SEQ ID NO:83) sequence produced a fragment of 2388 bp (SEQ ID NO:85) coding for a protein of 795 amino acids (SsTps1137, SEQ ID NO:86)). Comparison with published sequences showed homologies with class I diterpene synthases and particularly ent-kaurene synthases B. Highest homology was with an uncharacterized protein from *Vitis vinifera* (NCBI access No. CAO64942, 59% identity), an ent-kauren synthase from *Cucumis sativus* (NCBI access No. BAB19275, 54% identity) and an ent-kauren synthase from *Lactuca sativa* (NCBI access No. BAB12441, 54% identity). The SsTps1137 (SEQ ID NO:86) amino acid sequence contained a DDFFD motif typical of ionization-dependent (class I) terpene synthases and did not contain the characteristic class II motif.

The combination of the same forward primers with the reverse primers deduced from the 1132Cont147 (SEQ ID NO:82) did not allow the amplification of any fragment, confirming that these two sequences did not arise from the same cDNA. A 5'RACE approach was then used to identify the 5' end of the ORF corresponding to the 1132Cont147 sequence (SEQ ID NO:82). Using the primers 1132_race1 (SEQ ID NO:67) and 1132_race2 (SEQ ID NO:68), a 536 bp sequence (1132RACE, SEQ ID NO:87) was obtained which had 41 bases overlap with the 1132Cont147 fragment (SEQ ID NO:82). This RACE product was identical to the previously obtained 1134Cont147 sequence (SEQ ID NO:84) and no extension at the 5' end was observed. As observed previously, this sequence had homology with diterpene synthases but seemed shorter by at least 200 codons than all other published diterpene synthases sequences. 5'RACE experiments were performed, in order to try to extend the sequence toward the 5' end of the 1132Cont147 sequence (SEQ ID NO:82) and to identify the true translation initiation codon. Several sets of oligonucleotides (1132_race3 to 1132_race9, SEQ ID NO:69 to 75) were designed but no additional sequence information was obtained. This led us to suppose that one of the ATG codon in the 1134Cont147 sequence (SEQ ID NO:84) was actually the initiation codon of the corresponding diterpene synthase gene. The nucleotidic sequence of this putative diterpene synthase (named SsTps1132, SEQ ID NO:2) was reconstituted from the 1132Cont147 (SEQ ID NO:82) and 1132RACE (SEQ ID NO:87) sequences. Taking the first ATG, the 1728 bp ORF of SsTps1132 (SEQ ID NO:2) encoded for a 575 amino acid protein (SEQ ID NO:1). This protein contained the ionization-dependent modif (DDFFD) and shared homology, but relatively low, with published diterpene synthases; the closest sequence being a terpene synthase from *Nicotiana tabacum* (NCBI access No. AAS98912), with 37% identity.

Surprisingly, the identity between the SsTps1137 (SEQ ID NO:86) and SsTps1132 (SEQ ID NO:1) proteins was only 30% and these sequences shared only 21 to 23% identity with the class II SsLPPs first isolated from *S. sclarea* (SEQ ID NO:24 and 25, Examples 1-3). An alignment of these two proteins with selected diterpene synthases sequences BAB19275 (SEQ ID NO:106), AAS98912 (SEQ ID NO:107), ABH10734 (SEQ ID NO:108), CAO64942 (SEQ ID NO:109), BAB12441 (SEQ ID NO:110), and Q39548 (SEQ ID NO:111) is presented in FIGS. 4A-4D. The alignment shows that SsTps1132 (SEQ ID NO:1) is truncated at the N-terminal end by 150 to 240 amino acids compared to the other diterpene synthases. The ChloroP method (Emanuelsson et al, *Protein Science* 8, 978-984, 1999 was used to predict the presence of a chloroplast transit peptide in each protein sequence. For SsTps1137 (SEQ ID NO:86) and SsTps1132 (SEQ ID NO:1) chloroplast transit peptides of 22 and 51 amino acids respectively were predicted, arguing for a chloroplast localization of both proteins.

Search of all reads for sequences identical to the SsTps1137 (SEQ ID NO:85) and SsTps1132 (SEQ ID NO:2) DNA sequences, provided only 24 reads for SsTps1137 and 425 reads for SsTps1132. This difference in the number of reads generated from each transcript reflects a significant difference in the expression levels. Based on the relative number of reads obtained for each transcript, it can be estimated that the expression level of SsTps1132 (220 reads/Kb) was similar to the expression level of SsLPPs (260 reads/Kb) and that SsTps1137 was expressed at a much lower level (10 reads/Kb). With the assumption that enzymes catalyzing steps in the same metabolic pathway are generally expressed at a similar level, it can be speculated that SsTps1132 (SEQ ID NO:1) rather than SsTps1137 (SEQ ID NO:86) is involved in the same metabolic pathway as SsLPPs.

The contigs generated with the Edena software (Example 5) were searched for DNA sequences identical to the sequences of these two new putative class I diterpene synthases. For SsTps1137 (SEQ ID NO:85) no contig was found in accordance with the presumed low expression level of this enzyme. For SsTps1132 (SEQ ID NO:2), 4 contigs where found. The previously identified contig1610 (SEQ ID NO:38) and three additional contigs (of length of 53 to 96 bp) (SEQ ID NO:88 to 90) not previously identified as fragment of a diterpene synthase. Blastx search with these three sequences did not show homology with known protein sequences. The failure in finding homology for these contigs is due to the short lengths of these fragments and to the low homology of SsTps1132 (SEQ ID NO:1) with the diterpene synthases present in the databases. The observation of an N-terminal deletion of SsTps1132 (SEQ ID NO:1) compared to the other diterpene synthases also explains afterwards why the PCR approach first employed did not succeed. Indeed, the forward primers were designed from conserved regions present in the first 150 amino acids of diterpene synthases, a region absent in SsTps1132 (SEQ ID NO:1). The SsTps1137 sequence (SEQ ID NO:86) contains the conserved motifs used to design the primers and the corresponding DNA sequences are complementary to the primer sequences. Presumably, the amplification of SsTps1137 (SEQ ID NO:85) did not succeed in the PCR approach because of the low abundance of this transcript.

Example 8

Heterologous Expression of the *S. sclarea* Class I Diterpene Synthases in *E coli*

To assign an enzymatic activity to SsTps1137 (SEQ ID NO:86) and SsTps1132 (SEQ ID NO:1), the recombinant proteins were expressed in *E coli*. The full-length cDNAs were inserted into the pet101/D-TOPO vector using the Champion pET101 Directional TOPO Expression Kit.

For each enzyme, two constructs were prepared: one to express the full-length protein and one to express a truncated protein based on the chloroplast transit peptide prediction. The full-length SsTps1137 (SEQ ID NO:85) and SsTps1132 (SEQ ID NO:2) open reading frames were amplified from the cDNA library using the primer pairs 1137-start (SEQ ID NO:78) with 1137-stop (SEQ ID NO:80) and 1132-start1 (Seq ID No 76) with 1132-stop (SEQ ID NO:66) respectively. The primers 1137_start2 (SEQ ID NO:79) and 1137_stop (SEQ ID NO:80) were used to amplify a 72 bp truncated version of SsTps1137 designed to express the protein with 24 amino acids deleted at the N-terminal end. In the same manner, the primers 1132_start2 (SEQ ID NO:77) and 1132-stop (SEQ ID NO:66) were used to prepare a truncated version of SsTps1132 designed to express the protein with a 50 amino acid N-terminal deletion. All amplifications of cDNA for expression of the expression constructs were performed using the Pfu DNA polymerase (Promega), in a final volume of 50 µl containing 5 µl of Pfu DNA polymerase 10× buffer, 200 µM each dNTP, 0.4 µM each forward and reverse primer, 2.9 units Pfu DNA polymerase and 5 µl of 100-fold diluted cDNA (prepared as described herein in Example 1 using the Marathon™ cDNA Amplification Kit (Clontech)). The thermal cycling conditions were as follows: 1.5 min at 95° C.; 30 cycles of 45 sec at 95° C., 30 sec at 58° C. and 5 min at 72° C.; and 10 min at 72° C.

Figure 5:
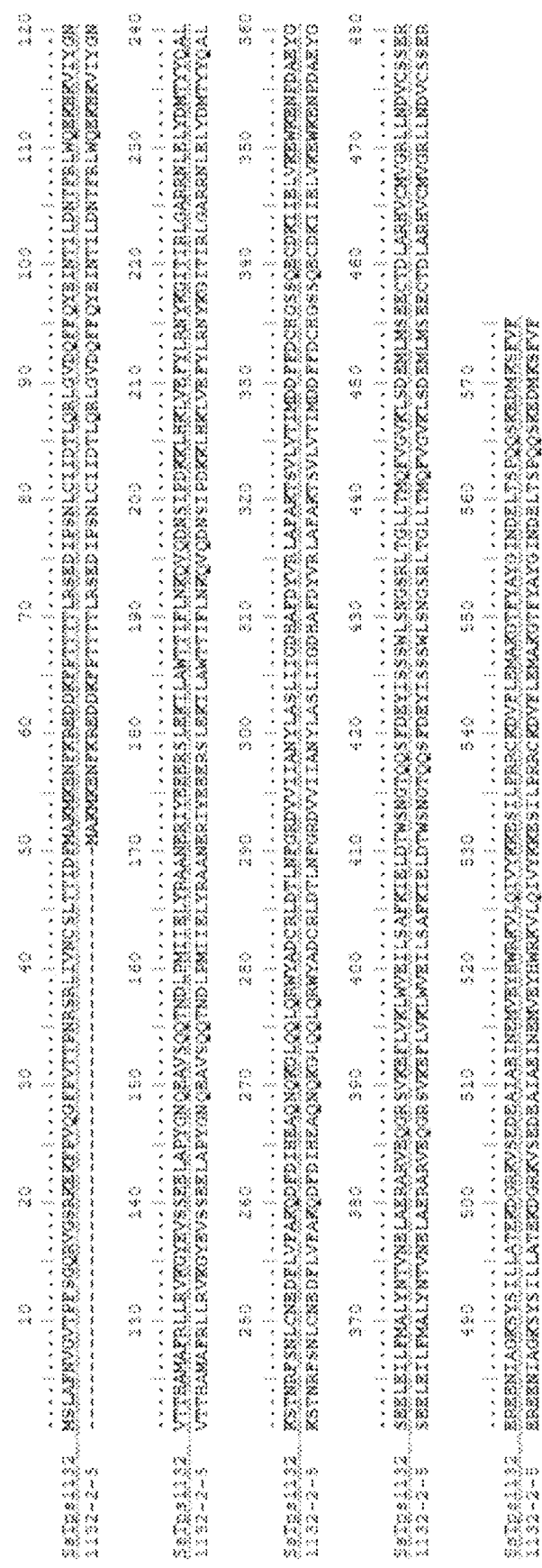
FIG. 5: Alignment of the amino acid sequences of SsTps1132 (SEQ ID NO:1) and 1132-2-5 (SEQ ID NO:96) which were heterologously expressed in *E coli*.

After the ligation in the pET101 vector, several clones were selected for each construct and were sequenced to ensure that no mutation had been introduced during the PCR amplification. For SsTps1137 the two constructs 1137-B12 (SEQ ID NO:91) and 1137-2-B12 (SEQ ID NO:92) were selected containing the SsTps1137 cDNA respectively with and without the peptide signal (corresponding polypeptide sequences are SEQ ID NO:94 and 95). For SsTps1132, two constructs were selected: one with the complete sequence of SsTps1132 (SEQ ID n0:2) and a construct without peptide signal (1132-2-5, SEQ ID NO:93). The alignment of the two amino acid sequences (SEQ ID NO:1 and 96) deduced from these constructs is shown in FIG. 5.

The plasmids pET101-1137-B12, pET101-1137-2-B12, pET101-SsTps1132, and pET101-1132-2-5 were transferred into B121(DE3) *E. Coli* cells (Novagene, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments. The crude protein extracts were analysed by SDS-PAGE and compared to protein extracts obtained from cells transformed with the empty pET101 plasmid.

Example 9

Enzymatic Activity of the Recombinant *S. Sclarea* Class I Diterpene Synthases in *E coli*

The crude *E coli* protein extracts containing the recombinant proteins and prepared as described in Example 8 were used for the characterization of the enzymatic activities. The enzymatic assays were performed as described in Example 3. All assays were performed in 50 mM MOPSO pH 7, 10% glycerol, 1 mM DTT.

Figure 6:
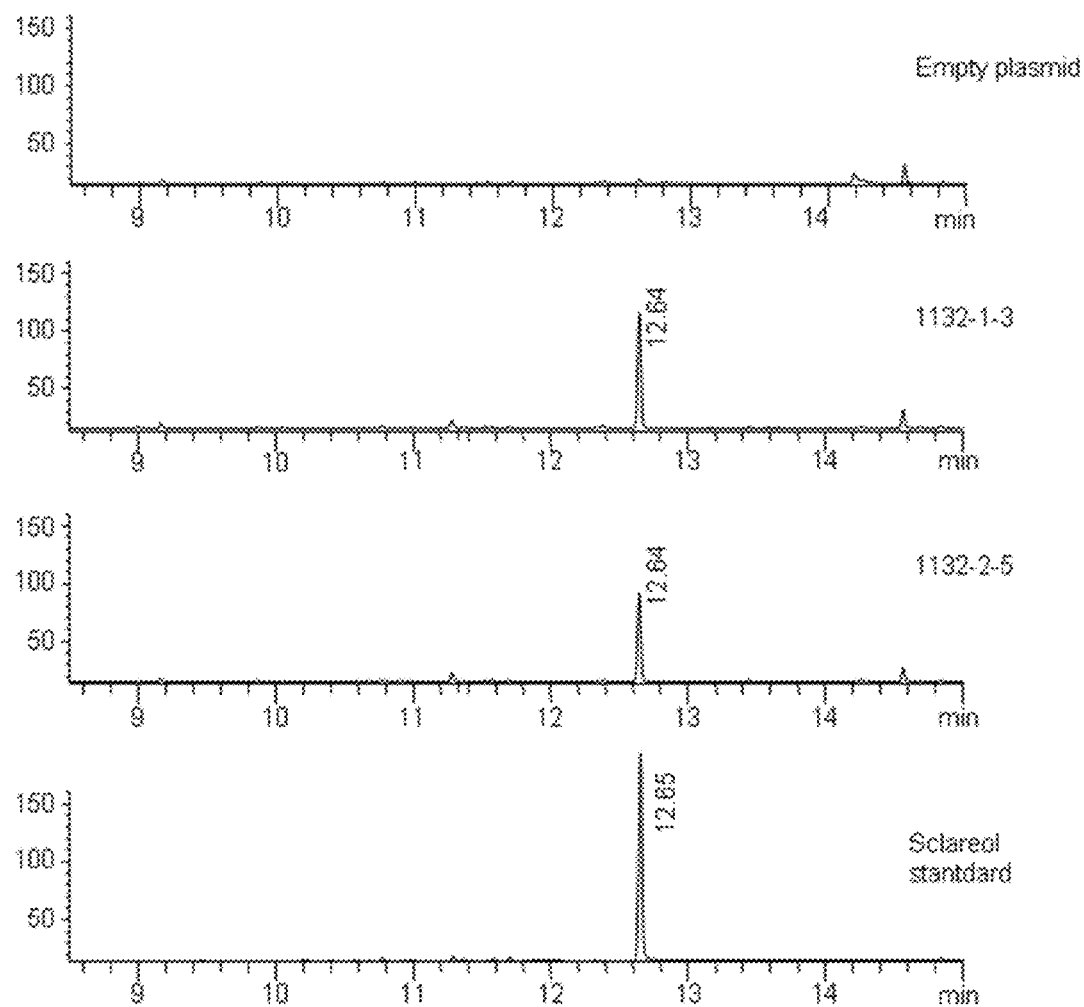
FIG. 6: GC analysis of the products obtained after incubation of the different 1132 recombinant proteins with LPP. Crude protein extracts from *E. coli* expressing the recombinant SsTps1132 and 1132-2-5 proteins (SEQ ID NO:1 and 96) were incubated with LPP in a in a final volume of 1 mL 50 mM MOPSO pH 7 supplemented with 15 mM $MgCl_2$ and 1 mM DTT.
Figure 7:
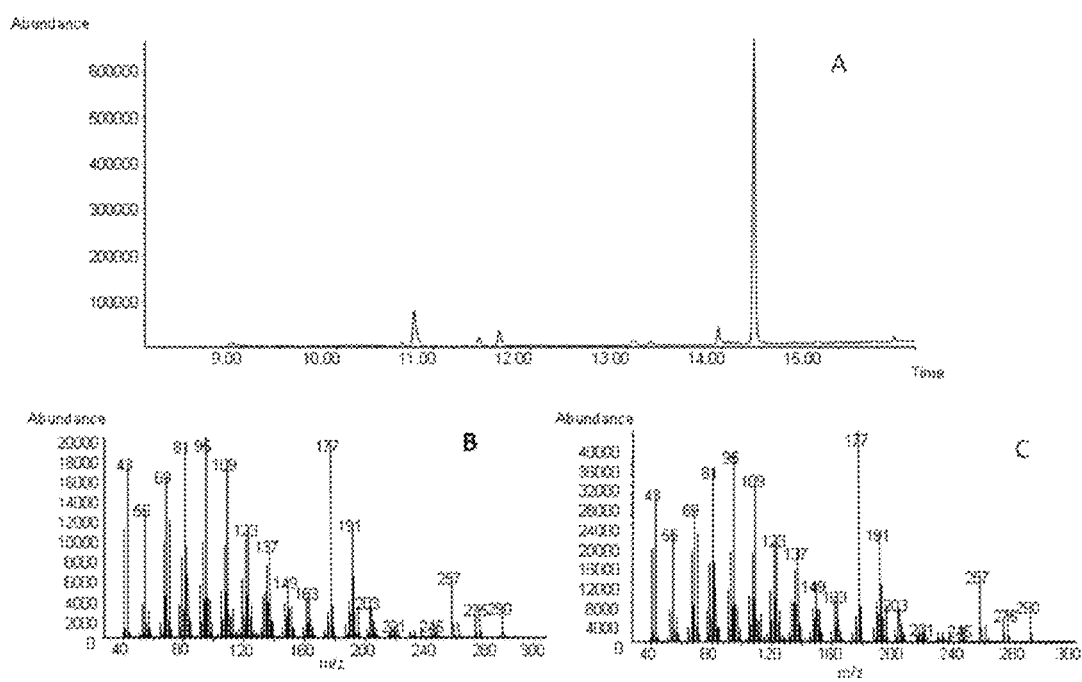
FIG. 7: GC-MS analysis of the products generated from LPP by the recombinant 1132-2-5 protein. (A) Total ion chromatogram of the products obtained from the incubation of LPP with a crude protein extract from *E. coli* transformed with pET101-1132-2-5 (SEQ ID NO:93). (B) Mass spectrum of the peak at retention time of 14.3. (C) Mass spectrum of an authentic sclareol standard.

The enzymatic activities were first evaluated using as substrate either GGPP or LPP, the product of SsLPPs (SEQ ID NO:22) and the presumed intermediate in the biosynthesis of sclareol (Examples 1 to 3). GGPP was synthesized as described by Keller and Thompson (*J. Chromatogr* 645(1), 1993, 161-167) and LPP was prepared enzymatically as described in Example 3. The assays were performed in the presence of 10 to 100 µM of substrate, 15 mM $MgCl_2$ and 0.1 to 0.5 mg of crude protein in a total volume of 1 mL. The tubes were incubated 4 to 12 hours at 30° C. and extracted twice with one volume of pentane. After concentration under a nitrogen flux, the extracts were analysed by GC and GC-MS (using the conditions described in Example 3) and compared to extracts from assay with control proteins (obtained from cells transformed with the empty plasmid). With GGPP as substrate, no activity was observed with any of recombinant proteins (data not shown). With LPP as substrate, no activity was observed with the proteins extracts containing SsTps1137 recombinant proteins but with SsTps1132, activity was observed with both SsTps1132 and 1132-2-5 (SEQ ID NO:1 and 96) (FIG. 6). The enzymes were also active in the absence of MgCl$_2$ and the same product profiles were observed with an overall activity roughly the same. The identity of product was confirmed by concordance of the retention times (FIG. 6) and matching of the mass spectrum with the spectrum of an authentic standard (FIG. 7). In all assays, a single peak of sclareol was observed with no trace of additional product.

Figure 8:
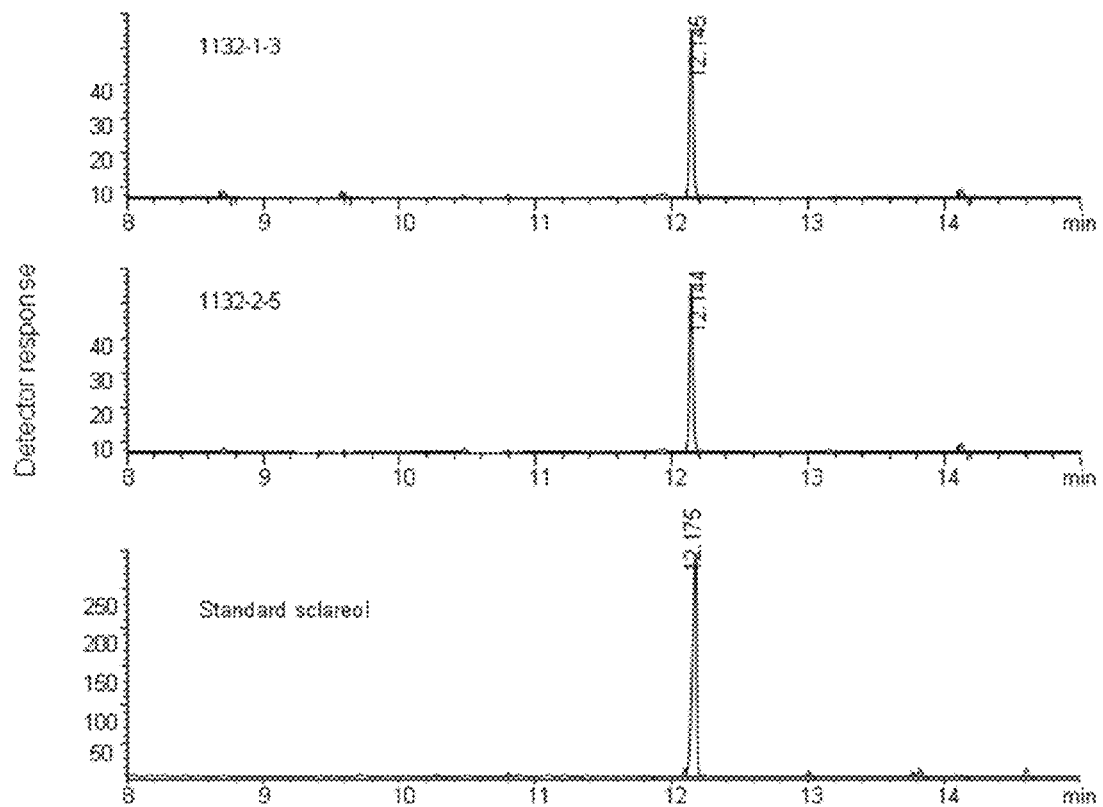
FIG. 8: GC analysis of the products obtained after co-incubation of SsTps1132 and 1132-2-5 recombinant proteins (SEQ ID NO:1 and 96) with the SsLPPs3 (SEQ ID NO:24) recombinant protein in the presence of GGPP.

Assays were then performed with co-incubation of the class II diterpene synthases (SsLPPs3, SEQ ID NO:24; Examples 1-3) and the class I diterpene synthases (1132 series, SEQ ID NO:1 and 96). Assays were performed in 50 mM MOPSO pH 7, 10% glycerol, 1 mM DTT, 50 µM GGPP, with 1 mM MgCl$_2$ and in the presence of 50 µL of the crude protein extracts from *E coli* expressing the different constructs. Thus assays in the presence of 50 µL of crude protein extracts containing the SsLPPs3 (SEQ ID NO:24) recombinant enzyme and 50 µL of extracts containing SsTps1132 (SEQ ID NO:1) or 1132-2-5 (SEQ ID NO:96) were evaluated for the production of diterpene products. FIG. 8 shows the GC profiles of extracts from such incubations in the presence of MgCl$_2$. Sclareol was produced with both 1132 constructs (SEQ ID NO: 1 and 96) (FIG. 8), a result consistent with the assay described above with LPP as substrate. No significant difference was observed when omitting MgCl$_2$ from the incubations (data not shown).

In conclusion the SsTps1132 (SEQ ID NO:2) encodes for the sclareol synthase (SEQ ID NO:1) and catalyses the conversion of LPP to sclareol.

The invention claimed is:

1. A method for producing sclareol comprising
a) contacting labdenediol diphosphate (LPP) with an isolated polypeptide having a sclareol synthase activity and comprising an amino acid sequence at least 90% identical to SEQ ID NO: 1; and
b) optionally, isolating the sclareol produced in step a).

2. The method of claim 1, wherein said polypeptide comprises an amino acid sequence at least 98% identical to SEQ ID NO:1.

3. The method of claim 1 wherein step a) is carried out by cultivating a non-human organism or cell capable of producing LPP and transformed to express said polypeptide under conditions conducive to the production of sclareol.

4. The method of claim 2 wherein step a) is carried out by cultivating a non-human organism or cell capable of producing LPP and transformed to express said polypeptide under conditions conducive to the production of sclareol.

5. The method of claim 3, further comprising, prior to step a), transforming the non human organism or cell capable of producing LPP with a nucleic acid encoding said polypeptide, so that said organism expresses said polypeptide.

6. The method of claim 4, further comprising, prior to step a), transforming the non human organism or cell capable of producing LPP with a nucleic acid encoding said polypeptide, so that said organism expresses said polypeptide.

7. The method of claim 3 wherein said non-human organism is a plant, a prokaryote or a fungus.

8. The method of claim 4 wherein said non-human organism is a plant, a prokaryote or a fungus.

9. The method of claim 3 wherein said non-human organism is a microorganism.

10. The method of claim 4 wherein said non-human organism is a microorganism.

11. The method of claim 9, wherein said microorganism is a bacteria or yeast.

12. The method of claim 10, wherein said microorganism is a bacteria or yeast.

13. The method of claim 11, wherein said bacteria is E. coli and said yeast is Saccharomyces cerevisiae.

14. The method of claim 12 wherein said bacteria is E. coil and said yeast is Saccharomyces cerevisiae.

15. The method of claim 3, wherein said non-human cell is a higher eukaryotic cell selected from plant cells or fungal cells.

16. The method of claim 4, wherein said non-human cell is a higher eukaryotic cell selected from plant cells or fungal cells.

* * * * *

SEQUENCE LISTING

```
<160> NUMBER OF SEQ ID NOS: 111

<210> SEQ ID NO 1
<211> LENGTH: 575
<212> TYPE: PRT
<213> ORGANISM: Salvia sclarea

<400> SEQUENCE: 1

Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile
        35                  40                  45

Asp Phe Met Ala Lys Met Lys Glu Asn Phe Lys Arg Glu Asp Asp Lys
    50                  55                  60

Phe Pro Thr Thr Thr Leu Arg Ser Glu Asp Ile Pro Ser Asn Leu
65                  70                  75                  80

Cys Ile Ile Asp Thr Leu Gln Arg Leu Gly Val Asp Gln Phe Phe Gln
                85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
    130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
```

```
                260             265             270
Leu Gln Gln Leu Gln Arg Trp Tyr Ala Asp Cys Arg Leu Asp Thr Leu
            275                 280                 285

Asn Phe Gly Arg Asp Val Val Ile Ile Ala Asn Tyr Leu Ala Ser Leu
        290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335

Ser Ser Gln Glu Cys Asp Lys Ile Ile Glu Leu Val Lys Glu Trp Lys
            340                 345                 350

Glu Asn Pro Asp Ala Glu Tyr Gly Ser Glu Glu Leu Glu Ile Leu Phe
        355                 360                 365

Met Ala Leu Tyr Asn Thr Val Asn Glu Leu Ala Glu Arg Ala Arg Val
        370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Trp Leu Ser Asn Gly
            420                 425                 430

Ser Arg Leu Thr Gly Leu Leu Thr Met Gln Phe Val Gly Val Lys Leu
        435                 440                 445

Ser Asp Glu Met Leu Met Ser Glu Glu Cys Thr Asp Leu Ala Arg His
450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
                500                 505                 510

Ile Asn Glu Met Val Glu Tyr His Trp Arg Lys Val Leu Gln Ile Val
        515                 520                 525

Tyr Lys Lys Glu Ser Ile Leu Pro Arg Arg Cys Lys Asp Val Phe Leu
        530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
                565                 570                 575

<210> SEQ ID NO 2
<211> LENGTH: 1728
<212> TYPE: DNA
<213> ORGANISM: Salvia sclarea

<400> SEQUENCE: 2
atgtcgctcg ccttcaacgt cggagttacg cctttctccg gccaaagagt tgggagcagg       60
aaagaaaaat ttccagtcca aggatttcct gtgaccaccc ccaataggtc acgtctcatc      120
gttaactgca gccttactac aatagatttc atggcgaaaa tgaaagagaa tttcaagagg      180
gaagacgata aatttccaac gacaacgact cttcgatccg aagatatacc ctctaatttg      240
tgtataatcg acacccttca aggttggggg tcgatcaat  tcttccaata tgaaatcaac      300
actattctag ataacacatt caggttgtgg caagaaaaac acaaagttat atatggcaat      360
```

```
gttactactc atgcaatggc atttaggctt tgcgagtga aaggatacga agtttcatca    420
gaggagttgg ctccatatgg taaccaagag gctgttagcc agcaaacaaa tgacctgccg    480
atgattattg agctttatag agcagcaaat gagagaatat atgaagaaga gaggagtctt    540
gaaaaaattc ttgcttggac taccatcttt ctcaataagc aagtgcaaga taactcaatt    600
cccgacaaaa aactgcacaa actggtggaa ttctacttga ggaattacaa aggcataacc    660
ataagattgg gagctagacg aaacctcgag ctatatgaca tgacctacta tcaagctctg    720
aaatctacaa acaggttctc taatttatgc aacgaagatt ttctagtttt cgcaaagcaa    780
gatttcgata tacatgaagc ccagaaccag aaaggacttc aacaactgca aaggtggtat    840
gcagattgta ggttggacac cttaaacttt ggaagagatg tagttattat tgctaattat    900
ttggcttcat taattattgg tgatcatgcg tttgactatg ttcgtctcgc atttgccaaa    960
acatctgtgc ttgtaacaat tatggatgat ttttcgact gtcatggctc tagtcaagag    1020
tgtgacaaga tcattgaatt agtaaaagaa tggaaggaga atccggatgc agagtacgga    1080
tctgaggagc ttgagatcct ttttatggcg ttgtacaata cagtaaatga gttggcggag    1140
agggctcgtg ttgaacaggg gcgtagtgtc aaagagtttc tagtcaaact gtgggttgaa    1200
atactctcag ctttcaagat agaattagat acatggagca atggcacgca gcaaagcttc    1260
gatgaataca tttcttcgtc gtggttgtcg aacggttccc ggctgacagg tctcctgacg    1320
atgcaattcg tcggagtaaa attgtccgat gaaatgctta tgagtgaaga gtgcactgat    1380
ttggctaggc atgtctgtat ggtcggccgg ctgctcaacg acgtgtgcag ttctgagagg    1440
gagcgcgagg aaaatattgc aggaaaaagt tatagcattc tactagcaac tgagaaagat    1500
ggaagaaaag ttagtgaaga tgaagccatt gcagagatca atgaaatggt tgaatatcac    1560
tggagaaaag tgttgcagat tgtgtataaa aagaaagca ttttgccaag aagatgcaaa    1620
gatgtatttt tggagatggc taagggtacg ttttatgctt atgggatcaa cgatgaattg    1680
acttctcctc agcaatccaa ggaagatatg aaatcctttg tcttttga               1728
```

<210> SEQ ID NO 3
<211> LENGTH: 22
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
gayrtngayg ayacngcnat gg                                             22

<210> SEQ ID NO 4
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature

```
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 4
gtyttnccna kccanacrtc ryyt                                              24

<210> SEQ ID NO 5
<211> LENGTH: 354
<212> TYPE: DNA
<213> ORGANISM: Salvia sclarea

<400> SEQUENCE: 5
gcgttaggct tctcaaaatg cacggatacg acgtcgatcc aaatgtacta aaacatttca       60
agcaacaaga tggtaaattt tcctgctaca ttggtcaatc ggtcgagtct gcatctccaa      120
tgtacaatct ttatagggct gctcaactaa gatttccagg agaagaagtt cttgaagaag      180
ccactaaatt tgcctttaac ttcttgcaag aaatgctagt caaagatcga cttcaagaaa      240
gatgggtgat atccgaccac ttatttgatg agataaagct ggggttgaag atgccatggt      300
acgccactct accccgagtc gaggctgcat attatctaga ccattatgct ggtt            354

<210> SEQ ID NO 6
<211> LENGTH: 29
<212> TYPE: DNA
<213> ORGANISM: Artificial sequence
<220> FEATURE:
<223> OTHER INFORMATION: Primer designed specifically for FN23

<400> SEQUENCE: 6
gcacggatac gacgtcgatc caaatgtac                                         29

<210> SEQ ID NO 7
<211> LENGTH: 27
<212> TYPE: DNA
<213> ORGANISM: Artificial sequence
<220> FEATURE:
<223> OTHER INFORMATION: Primer designed specifically for FN23

<400> SEQUENCE: 7
gggctgctca actaagattt ccaggag                                           27

<210> SEQ ID NO 8
<211> LENGTH: 29
<212> TYPE: DNA
<213> ORGANISM: Artificial sequence
<220> FEATURE:
<223> OTHER INFORMATION: Primer designed specifically for FN23

<400> SEQUENCE: 8
gggtgatatc cgaccactta tttgatgag                                         29

<210> SEQ ID NO 9
<211> LENGTH: 36
<212> TYPE: DNA
<213> ORGANISM: Artificial sequence
<220> FEATURE:
<223> OTHER INFORMATION: Adaptor sequence to extend oligodT primers
```

<400> SEQUENCE: 9

```
aattcggtac ccgggatcct tttttttttt tttttt                                    36
```

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10

```
aattcggtac ccgggatcc                                                       19
```

<210> SEQ ID NO 11
<211> LENGTH: 1271
<212> TYPE: DNA
<213> ORGANISM: Salvia sclarea

<400> SEQUENCE: 11

```
aagaagttct tgaagaagcc actaaatttg cctttaactt cttgcaagaa atgctagtca          60
aagatcgact tcaagaaaga tgggtgatat ccgaccactt atttgatgag ataaagctgg         120
ggttgaagat gccatggtac gccactctac cccgagtcga ggctgcatat tatctagacc         180
attatgctgg ttctggtgat gtatggattg gcaagagttt ctacaggatg ccagaaatca         240
gcaatgatac atacaaggag cttgcgtatt ggatttcaa cagatgccaa acacaacatc          300
agttggagtg gatccatatg caggaatggt acgacagatg cagccttagc gaattcggga         360
taagcaaaag agagttgctt cgctcttact ttctggccgc agcaaccata ttcgaaccgg         420
agagaactca agagaggctt ctgtgggcca aaccagaat tctttctaag atgatcactt          480
catttgtcaa cattagtgga acaacactat ctttggacta caatttcaat ggcctcgatg         540
aaataattag tagtgccaat gaagatcaag gactggctgg gactctgctg caaccttcc          600
atcaacttct agacggattc gatatataca ctctccatca actcaaacat gtttggagcc         660
aatggttcat gaaagtgcag caaggagagg gaagcggcgg ggaagacgcg gtgctcctag         720
cgaacacgct caacatctgc gccggcctca cgaagacgt gttgtccaac aatgaataca          780
cggctctgtc cacccctcaca aataaaatct gcaatcgcct cgcccaaatt caagacaata         840
agattctcca agttgtggat gggagcataa aggataagga gctagaacag atatgcagg          900
cgttggtgaa gttagtgctt caagaaaatg gcggcgccgt agacagaaac atcagacaca         960
cgtttttgtc ggtttccaag actttctact acgatgccta ccacgacgat gagacgaccg        1020
atcttcatat cttcaaagta ctcttcgac cggttgtatg aaaaatattt taagctcgtc         1080
tgcagtccac gtagataatt attttaaaat aaaggataaa ttaacgagaa acgacgccat        1140
tttaaaataa tatgttaaga atggacccta ataagagcg tcgaaacatg cattgggata         1200
taatttatta attgttacac catttcggaa taaaatgatg ttatttcttt tcatatgta         1260
aaaaaaaaaa a                                                             1271
```

<210> SEQ ID NO 12
<211> LENGTH: 32
<212> TYPE: DNA
<213> ORGANISM: Artificial sequence
<220> FEATURE:
<223> OTHER INFORMATION: Primer designed specifically for FN23

<400> SEQUENCE: 12

```
catggcatct tcaaccccag ctttatctca tc                                        32
```

<210> SEQ ID NO 13
<211> LENGTH: 33
<212> TYPE: DNA
<213> ORGANISM: Artificial sequence
<220> FEATURE:
<223> OTHER INFORMATION: Primer designed specifically for FN23

<400> SEQUENCE: 13
gtggtcggat atcacccatc tttcttgaag tcg                          33

<210> SEQ ID NO 14
<211> LENGTH: 30
<212> TYPE: DNA
<213> ORGANISM: Artificial sequence
<220> FEATURE:
<223> OTHER INFORMATION: Primer designed specifically for FN23

<400> SEQUENCE: 14
cattggagat gcagactcga ccgattgacc                              30

<210> SEQ ID NO 15
<211> LENGTH: 1449
<212> TYPE: DNA
<213> ORGANISM: Salvia sclarea

<400> SEQUENCE: 15
caaaattctc ttccattttt aagataatag taatattcta attttccctc caaaaactcg      60
tgggaaattg aaaaatagaa aataaagatg acttctgtaa atttgagcag agcaccagca     120
gcgattatcc ggcgcaggct gcagctacag ccggaatttc atgccgagtg ttcatggctg     180
aaaagcagca gcaaacacgc gcccttgacc ttgagttgcc aaatccgtcc taagcaactc     240
tcccaaatag ctgaattgag agtaacaagc ctggatgcgt cgcaagcgag tgaaaaagac     300
atttcccttg ttcaaactcc gcataaggtt gaggttaatg aaaagatcga ggagtcaatc     360
gagtacgtcc aaaatctgtt gatgacgtcg ggcgacgggc gaataagcgt gtcaccctat     420
gacacggcag tgatcgccct gatcaaggac ttgaaagggc gcgacgcccc gcagtttccg     480
tcatgtctcg agtggatcgc gcaccaccaa ctggctgatg ctcatgggg cgacgaattc     540 ttctgtattt atgatcggat tctaaataca ttggcatgtg tcgtagcctt gaaatcatgg     600
aaccttcact ctgatattat tgaaaagga gtgacgtaca tcaaggagaa tgtgcataaa     660
cttaaaggtg caaatgttga gcacaggaca gcggggttcg aacttgtggt tcctactttt     720
atgcaaatgg ccacagattt gggcatccaa gatctgccct atgatcatcc cctcatcaag     780
gagattgctg acacaaaaca acaaagattg aaagagatac ccaaggattt ggtttaccaa     840
atgccaacga atttactgta cagtttagaa gggttaggag atttggagtg ggaaaggcta     900
ctgaaactgc agtcgggcaa tggctccttc ctcacttcgc cgtcgtccac cgccgccgtc     960
ttgatgcata ccaagatgaa aaatgtttg aaatacatcg aaaacgccct caagaattgc    1020
gacggaggag caccacatac ttatccagtc gatatcttct caagactttg ggcaatcgat    1080
aggctacaac gcctaggaat ttctcgtttc ttccagcacg agatcaagta tttcttagat    1140
cacatcgaaa gcgtttggga ggagaccgga gttttcagtg gaagatatac gaaatttagc    1200
gatattgatg acacgtccat gggcgttagg cttctcaaaa tgcacggata cgacgtcgat    1260
ccaaatgtac taaacatttt caagcaacaa gatggtaaat tttcctgcta cattggtcaa    1320
tcggtcgagt ctgcatctcc aatgtacaat ctttataggg ctgctcaact aagatttcca    1380

| | |
|---|---|
| ggagaagaag ttcttgaaga agccactaaa tttgccttta acttcttgca agaaatgcta | 1440 |
| gtcaaagat | 1449 |

<210> SEQ ID NO 16
<211> LENGTH: 2655
<212> TYPE: DNA
<213> ORGANISM: Salvia sclarea

<400> SEQUENCE: 16

| | |
|---|---|
| caaaattctc ttccattttt aagataatag taatattcta attttccctc caaaaactcg | 60 |
| tgggaaattg aaaaatagaa ataaagatg acttctgtaa atttgagcag agcaccagca | 120 |
| gcgattatcc ggcgcaggct gcagctacag ccggaatttc atgccgagtg ttcatggctg | 180 |
| aaaagcagca gcaaacacgc gcccttgacc ttgagttgcc aaatccgtcc taagcaactc | 240 |
| tcccaaatag ctgaattgag agtaacaagc ctggatgcgt cgcaagcgag tgaaaaagac | 300 |
| atttcccttg ttcaaactcc gcataaggtt gaggttaatg aaaagatcga ggagtcaatc | 360 |
| gagtacgtcc aaaatctgtt gatgacgtcg ggcgacgggc gaataagcgt gtcaccctat | 420 |
| gacacggcag tgatcgccct gatcaaggac ttgaaagggc gcgacgcccc gcagtttccg | 480 |
| tcatgtctcg agtggatcgc gcaccaccaa ctggctgatg gctcatgggg cgacgaattc | 540 |
| ttctgtattt atgatcggat tctaaataca ttggcatgtg tcgtagcctt gaaatcatgg | 600 |
| aaccttcact ctgatattat tgaaaaagga gtgacgtaca tcaaggagaa tgtgcataaa | 660 |
| cttaaggtg caaatgttga gcacaggaca gcggggttcg aacttgtggt tcctactttt | 720 |
| atgcaaatgg ccacagattt gggcatccaa gatctgccct atgatcatcc cctcatcaag | 780 |
| gagattgctg acacaaaaca acaaagattg aaagagatac ccaaggattt ggtttaccaa | 840 |
| atgccaacga atttactgta cagtttagaa gggttaggag atttggagtg ggaaaggcta | 900 |
| ctgaaactgc agtcgggcaa tggctccttc ctcacttcgc cgtcgtccac cgccgccgtc | 960 |
| ttgatgcata ccaaagatga aaatgtgttt aaatacatcg aaaacgccct caagaattgc | 1020 |
| gacggaggag caccacatac ttatccagtc gatatcttct caagactttg ggcaatcgat | 1080 |
| aggctacaac gcctaggaat ttctcgtttc ttccagcacg agatcaagta tttcttagat | 1140 |
| cacatcgaaa gcgtttggga ggagaccgga gttttcagtg aagatatac gaaatttagc | 1200 |
| gatattgatg acacgtccat gggcgttagg cttctcaaaa tgcacggata cgacgtcgat | 1260 |
| ccaaatgtac taaaacattt caagcaacaa gatggtaaat tttcctgcta cattggtcaa | 1320 |
| tcggtcgagt ctgcatctcc aatgtacaat ctttataggg ctgctcaact aagatttcca | 1380 |
| ggagaagaag ttcttgaaga agccactaaa tttgccttta acttcttgca agaaatgcta | 1440 |
| gtcaaagatc gacttcaaga agatgggtg atatccgacc acttatttga tgagataaag | 1500 |
| ctgggggttga agatgccatg gtacgccact ctaccccgag tcgaggctgc atattatcta | 1560 |
| gaccattatg ctggttctgg tgatgtatgg attggcaaga gtttctacag gatgccagaa | 1620 |
| atcagcaatg atacatacaa ggagcttgcg atattggatt caacagatg ccaaacacaa | 1680 |
| catcagttgg agtggatcca tatgcaggaa tggtacgaca gatgcagcct tagcgaattc | 1740 |
| gggataagca aaagagagtt gcttcgctct tactttctgg ccgcagcaac catattcgaa | 1800 |
| ccggagagaa ctcaagagag gcttctgtgg gccaaaacca gaattcttc taagatgatc | 1860 |
| acttcatttg tcaacattag tggaacaaca ctatctttgg actacaattt caatggcctc | 1920 |
| gatgaaaata ttagtagtgc caatgaagat caaggactgg ctgggactct gctgcaacc | 1980 |
| ttccatcaac ttctagacgg attcgatata tacactctcc atcaactcaa acatgtttgg | 2040 |

-continued

```
agccaatggt tcatgaaagt gcagcaagga gagggaagcg gcggggaaga cgcggtgctc    2100
ctagcgaaca cgctcaacat ctgcgccggc ctcaacgaag acgtgttgtc caacaatgaa    2160
tacacggctc tgtccaccct cacaaataaa atctgcaatc gcctcgccca aattcaagac    2220
aataagattc tccaagttgt ggatgggagc ataaaggata aggagctaga acaggatatg    2280
caggcgttgg tgaagttagt gcttcaagaa atggcggcg ccgtagacag aaacatcaga    2340
cacacgtttt tgtcggtttc caagactttc tactacgatg cctaccacga cgatgagacg    2400
accgatcttc atatcttcaa agtactcttt cgaccggttg tatgaaaaat attttaagct    2460
cgtctgcagt ccacgtagat aattatttta aataaaggga taaattaacg agaaacgacg    2520
ccattttaaa ataatatgtt aagaatggac cctaaataag agcgtcgaaa catgcattgg    2580
gatataattt attaattgtt acaccatttc ggaataaaat gatgttattt cttttcata    2640 tgtaaaaaaa aaaaa                                                     2655
```

<210> SEQ ID NO 17
<211> LENGTH: 785
<212> TYPE: PRT
<213> ORGANISM: Salvia sclarea

<400> SEQUENCE: 17

```
Met Thr Ser Val Asn Leu Ser Arg Ala Pro Ala Ile Ile Arg Arg
 1               5                  10                  15

Arg Leu Gln Leu Gln Pro Glu Phe His Ala Glu Cys Ser Trp Leu Lys
                20                  25                  30

Ser Ser Ser Lys His Ala Pro Leu Thr Leu Ser Cys Gln Ile Arg Pro
            35                  40                  45

Lys Gln Leu Ser Gln Ile Ala Glu Leu Arg Val Thr Ser Leu Asp Ala
        50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
                100                 105                 110

Thr Ala Val Ile Ala Leu Ile Lys Asp Leu Lys Gly Arg Asp Ala Pro
            115                 120                 125

Gln Phe Pro Ser Cys Leu Glu Trp Ile Ala His Gln Leu Ala Asp
        130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
                180                 185                 190

Lys Gly Ala Asn Val Glu His Arg Thr Ala Gly Phe Glu Leu Val Val
            195                 200                 205

Pro Thr Phe Met Gln Met Ala Thr Asp Leu Gly Ile Gln Asp Leu Pro
        210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255
```

```
Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
    370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
        435                 440                 445

Glu Met Leu Val Lys Asp Arg Leu Gln Glu Arg Trp Val Ile Ser Asp
    450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile His Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
        595                 600                 605

Asn Gly Leu Asp Glu Ile Ile Ser Ser Ala Asn Glu Asp Gln Gly Leu
    610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
```

```
          675                 680                 685
Asn Asn Glu Tyr Thr Ala Leu Ser Thr Leu Thr Asn Lys Ile Cys Asn
    690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
            740                 745                 750

Thr Phe Leu Ser Val Ser Lys Thr Phe Tyr Tyr Asp Ala Tyr His Asp
        755                 760                 765

Asp Glu Thr Thr Asp Leu His Ile Phe Lys Val Leu Phe Arg Pro Val
770                 775                 780

Val
785

<210> SEQ ID NO 18
<211> LENGTH: 38
<212> TYPE: DNA
<213> ORGANISM: Artificial sequence
<220> FEATURE:
<223> OTHER INFORMATION: Primer

<400> SEQUENCE: 18
tactgacata tgacttctgt aaatttgagc agagcacc                              38

<210> SEQ ID NO 19
<211> LENGTH: 36
<212> TYPE: DNA
<213> ORGANISM: Artificial sequence
<220> FEATURE:
<223> OTHER INFORMATION: Primer

<400> SEQUENCE: 19
ttggtacctc atacaaccgg tcgaaagagt actttg                                36

<210> SEQ ID NO 20
<211> LENGTH: 31
<212> TYPE: DNA
<213> ORGANISM: Artificial sequence
<220> FEATURE:
<223> OTHER INFORMATION: Primer

<400> SEQUENCE: 20
gttggagtgg atccacatgc aggaatggta c                                     31

<210> SEQ ID NO 21
<211> LENGTH: 31
<212> TYPE: DNA
<213> ORGANISM: Artificial sequence
<220> FEATURE:
<223> OTHER INFORMATION: Primer

<400> SEQUENCE: 21
gtaccattcc tgcatctgga tccactccaa c                                     31

<210> SEQ ID NO 22
<211> LENGTH: 2358
<212> TYPE: DNA
<213> ORGANISM: Salvia sclarea

<400> SEQUENCE: 22
```

```
atgacttctg taaatttgag cagagcacca gcagcgatta cccggcgcag gctgcagcta    60
cagccggaat tcatgccga gtgttcatgg ctgaaaagca gcagcaaaca cgcgcccttg    120
accttgagtt gccaaatccg tcctaagcaa ctctcccaaa tagctgaatt gagagtaaca   180
agcctggatg cgtcgcaagc gagtgaaaaa gacatttccc ttgttcaaac tccgcataag   240
gttgaggtta atgaaaagat cgaggagtca atcgagtacg tccaaaatct gttgatgacg   300
tcgggcgacg ggcgaataag cgtgtcaccc tatgacacgg cagtgatcgc cctgatcaag   360
gacttgaaag ggcgcgacgc cccgcagttt ccgtcatgtc tcgagtggat cgcgcaccac   420
caactggctg atggctcatg gggcgacgaa ttcttctgta tttatgatcg gattctaaat   480
acattggcat gtgtcgtagc cttgaaatca tggaaccttc actctgatat tattgaaaaa   540
ggagtgacgt acatcaagga gaatgtgcat aaacttaaag gtgcaaatgt tgagcacagg   600
acagcgggt tcgaacttgt ggttcctact tttatgcaaa tggccacaga tttgggcatc    660
caagatctgc cctatgatca tcccctcatc aaggagattg ctgacacaaa acaacaaaga   720
ttgaaagaga tacccaagga tttggtttac caaatgccaa cgaatttact gtacagttta   780
gaagggttag gagatttgga gtgggaaagg ctactgaaac tgcagtcggg caatggctcc   840
ttcctcactt cgccgtcgtc caccgccgcc gtcttgatgc ataccaaaga tgaaaaatgt   900
ttgaaataca tcgaaaacgc cctcaagaat tgcgacggag gagcaccaca tacttatcca   960
gtcgatatct tctcaagact ttgggcaatc gataggctac aacgcctagg aatttctcgt  1020
ttcttccagc acgagatcaa gtatttctta gatcacatcg aaagcgtttg ggaggagacc  1080
ggagttttca gtggaagata tacgaaattt agcgatattg atgacacgtc catgggcgtt  1140
aggcttctca aaatgcacgg atacgacgtc gatccaaatg tactaaaaca tttcaagcaa  1200
caagatggta aattttcctg ctacattggt caatcggtcg agtctgcatc tccaatgtac  1260
aatctttata gggctgctca actaagattt ccaggagaag aagttcttga agaagccact  1320
aaatttgcct ttaacttctt gcaagaaatg ctagtcaaag atcgacttca agaaagatgg  1380
gtgatatccg accacttatt tgatgagata aagctggggt tgaagatgcc atggtacgcc  1440
actctacccc gagtcgaggc tgcatattat ctagaccatt atgctggttc tggtgatgta  1500
tggattggca agagtttcta caggatgcca gaaatcagca atgatacata caaggagctt  1560
gcgatattgg atttcaacag atgccaaaca caacatcagt tggagtggat ccacatgcag  1620
gaatggtacg acagatgcag ccttagcgaa ttcgggataa gcaaaagaga gttgcttcgc  1680
tcttactttc tggccgcagc aaccatattc gaaccggaga gaactcaaga gaggcttctg  1740
tgggccaaaa ccagaattct ttctaagatg atcacttcat ttgtcaacat tagtggaaca  1800
acactatctt tggactacaa tttcaatggc ctcgatgaaa taattagtag tgccaatgaa  1860
gatcaaggac tggctgggac tctgctggca accttccatc aacttctaga cggattcgat  1920
atatacactc tccatcaact caaacatgtt tggagccaat ggttcatgaa agtgcagcaa  1980
ggagagggaa gcggcgggga agacgcggtg ctcctagcga acacgctcaa catctgcgcc  2040
ggcctcaacg aagacgtgtt gtccaacaat gaatacacgg ctctgtccac cctcacaaat  2100
aaaatctgca atcgcctcgc ccaaattcaa gacaataaga ttctccaagt tgtggatggg  2160
agcataaagg ataaggagct agaacaggat atgcaggcgt tggtgaagtt agtgcttcaa  2220
gaaaatggcg gcgccgtaga cagaaacatc agacacacgt ttttgtcggt ttccaagact  2280
ttctactacg atgcctacca cgacgatgag acgaccgatc ttcatatctt caaagtactc  2340
tttcgaccgg ttgtatga                                                2358
```

<210> SEQ ID NO 23
<211> LENGTH: 2355
<212> TYPE: DNA
<213> ORGANISM: Salvia sclarea

<400> SEQUENCE: 23

```
atgacttctg taaatttgag cagagcacca gcagcgatta tccggcgcag gctgcagcta      60
cagccggaat tcatgccga gtgttcatgg ctgaaaagca gcagcaaaca cgcgcccttc     120
accttgagtt gccaaatccg tcctaagcaa ctctcccaaa tagctgaatt gagagtaaca     180
agcctggatg cgtcgcaagc gagtgaaaaa gacatttccc ttgttcaaac tccgcataag     240
gttgaggtta atgaaaagat cgaggagtca atcgagtacg tccaaaatct gttgatgacg     300
tcgggcgacg ggcgaataag cgtgtcaccc tatgacacgg cagtgatcgc cctgatcaag     360
gacttgaaag ggcgcgacgc cccgcagttt ccgtcatgtc tcgagtggat cgcgcaccac     420
caactggctg atggctcatg gggcgacgaa ttcttctgta tttatgatcg gattctaaat     480
acattggcat gtgtcgtagc cttgaaatca tggaaccttc aatctgatat tattgaaaaa     540
ggtgtgacgt acatcaagga gaatgtgcat aaacttaaag gtgcaaatgt tgagcacagg     600
acagcgggt cgaacttgt ggttcctact tttatgcaaa tggccacaga tttgggcatc     660
caaggtctgc cctatgatca tccccctcatc aaggagattg ctgacacaaa acaacaaaga    720
ttgaaagaga tacccaagga tttggtttac caaatgccaa cgaatttact gtacagttta     780
gaagggttag agatttgga gtgggaaagg ttactgaaac tgcagtcggg caatggctcc     840
ttcctcactt cgccgtcgtc caccgccgcc gtcttgatgc ataccaaaga tgaaaaatgt     900
ttgaaataca tcgaaaacgc cctcaagaat tgcgacggag gagcaccaca tacttatcca     960
gtcgatatct tctcaagact ttgggcaatc gataggctac aacgcctagg aatttctcgt    1020
ttcttccagc acgagatcaa gtatttctta gatcacatcg aaagcgtttg ggaggagacc    1080
ggagttttca gtggaagata tacgaaattt agcgatattg atgacacgtc catgggcgtt    1140
aggcttctca aaatgcacgg atacgacgtc gatccaaatg tactaaaaca tttcaagcaa    1200
caagatggta attttcctg ctacattggt caatcggtcg agtctgcatc tccaatgtac    1260
aatctttata gggctgctca actaagattt ccaggagaag aagttcttga agaagccact    1320
aaatttgcct taacttctt gcaagaaatg ctagtcaaag atcgacttca agaaagatgg    1380
gtgatatccg accacttatt tgatgagata aagctgggggt tgaagatgcc atggtacgcc    1440
actctacccc gagtcgaggc tgcatattat ctagaccatt atgctggttc tggtgatgta    1500
tggattggca agagtttcta caggatgcca gaaatcagca atgatacata caggagctt    1560
gcgatattgg atttcaacag atgccaaaca caacatcagt ggagtggat ccagatgcag    1620
gaatggtacg acagatgcag ccttagcgaa ttcgggataa gcaaaagaga gttgcttcgc    1680
tcttactttc tggccgcagc aaccatattc gaaccggaga gaactcaaga gaggcttctg    1740
tgggccaaaa ccagaattct ttctaagatg atcacttcat ttgtcaacat tagtggaaca    1800
acactatctt tggactacaa tttcaatggc ctcgatgaaa taattagtgc caatgaagat    1860
caaggactgg ctgggactct gctggcaacc ttccatcaac ttctagacgg attcgatata    1920
tacactctcc atcaactcaa acatgttttgg agccaatggt tcatgaaagt gcagcaagga    1980
gagggaagcg gcggggaaga cgcggtgctc ctagcgaaca cgctcaacat ctgcgccggc    2040
ctcaacgaag acgtgttgtc caacaatgaa tacacggctc tgtccaccct cacaaataaa    2100
```

-continued

```
atctgcaatc gcctcgccca aattcaagac aataagattc tccaagttgt ggatgggagc    2160
ataaaggata aggagctaga acaggatatg caggcgttgg tgaagttagt gcttcaagaa    2220
aatggcggcg ccgtagacag aaacatcaga cacacgtttt tgtcggtttc caagactttc    2280
tactacgatg cctaccacga cgatgagacg accgatcttc atatcttcaa agtactcttt    2340
cgaccggttg tatga                                                      2355
```

<210> SEQ ID NO 24
<211> LENGTH: 785
<212> TYPE: PRT
<213> ORGANISM: Salvia sclarea

<400> SEQUENCE: 24

```
Met Thr Ser Val Asn Leu Ser Arg Ala Pro Ala Ala Ile Thr Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Leu Thr Leu Ser Cys Gln Ile Arg Pro
        35                  40                  45

Lys Gln Leu Ser Gln Ile Ala Glu Leu Arg Val Thr Ser Leu Asp Ala
    50                  55                  60

Ser Gln Ala Ser Glu Lys Asp Ile Ser Leu Val Gln Thr Pro His Lys
65                  70                  75                  80

Val Glu Val Asn Glu Lys Ile Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His Gln Leu Ala Asp
    130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Asp Leu Pro
    210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
```

-continued

```
            325                 330                 335
Gly Ile Ser Arg Phe Phe Gln His Glu Ile Lys Tyr Phe Leu Asp His
            340                 345                 350
Ile Glu Ser Val Trp Glu Glu Thr Gly Val Phe Ser Gly Arg Tyr Thr
            355                 360                 365
Lys Phe Ser Asp Ile Asp Asp Thr Ser Met Gly Val Arg Leu Leu Lys
            370                 375                 380
Met His Gly Tyr Asp Val Asp Pro Asn Val Leu Lys His Phe Lys Gln
385                 390                 395                 400
Gln Asp Gly Lys Phe Ser Cys Tyr Ile Gly Gln Ser Val Glu Ser Ala
                    405                 410                 415
Ser Pro Met Tyr Asn Leu Tyr Arg Ala Ala Gln Leu Arg Phe Pro Gly
                    420                 425                 430
Glu Glu Val Leu Glu Ala Thr Lys Phe Ala Phe Asn Phe Leu Gln
                    435                 440                 445
Glu Met Leu Val Lys Asp Arg Leu Gln Glu Arg Trp Val Ile Ser Asp
                    450                 455                 460
His Leu Phe Asp Glu Ile Lys Leu Gly Leu Lys Met Pro Trp Tyr Ala
465                 470                 475                 480
Thr Leu Pro Arg Val Glu Ala Ala Tyr Tyr Leu Asp His Tyr Ala Gly
                    485                 490                 495
Ser Gly Asp Val Trp Ile Gly Lys Ser Phe Tyr Arg Met Pro Glu Ile
                    500                 505                 510
Ser Asn Asp Thr Tyr Lys Glu Leu Ala Ile Leu Asp Phe Asn Arg Cys
                    515                 520                 525
Gln Thr Gln His Gln Leu Glu Trp Ile His Met Gln Glu Trp Tyr Asp
                    530                 535                 540
Arg Cys Ser Leu Ser Glu Phe Gly Ile Ser Lys Arg Glu Leu Leu Arg
545                 550                 555                 560
Ser Tyr Phe Leu Ala Ala Ala Thr Ile Phe Glu Pro Glu Arg Thr Gln
                    565                 570                 575
Glu Arg Leu Leu Trp Ala Lys Thr Arg Ile Leu Ser Lys Met Ile Thr
                    580                 585                 590
Ser Phe Val Asn Ile Ser Gly Thr Thr Leu Ser Leu Asp Tyr Asn Phe
                    595                 600                 605
Asn Gly Leu Asp Glu Ile Ile Ser Ser Ala Asn Glu Asp Gln Gly Leu
                    610                 615                 620
Ala Gly Thr Leu Leu Ala Thr Phe His Gln Leu Leu Asp Gly Phe Asp
625                 630                 635                 640
Ile Tyr Thr Leu His Gln Leu Lys His Val Trp Ser Gln Trp Phe Met
                    645                 650                 655
Lys Val Gln Gln Gly Glu Gly Ser Gly Gly Glu Asp Ala Val Leu Leu
                    660                 665                 670
Ala Asn Thr Leu Asn Ile Cys Ala Gly Leu Asn Glu Asp Val Leu Ser
                    675                 680                 685
Asn Asn Glu Tyr Thr Ala Leu Ser Thr Leu Thr Asn Lys Ile Cys Asn
                    690                 695                 700
Arg Leu Ala Gln Ile Gln Asp Asn Lys Ile Leu Gln Val Val Asp Gly
705                 710                 715                 720
Ser Ile Lys Asp Lys Glu Leu Glu Gln Asp Met Gln Ala Leu Val Lys
                    725                 730                 735
Leu Val Leu Gln Glu Asn Gly Gly Ala Val Asp Arg Asn Ile Arg His
                    740                 745                 750
```

-continued

```
Thr Phe Leu Ser Val Ser Lys Thr Phe Tyr Tyr Asp Ala Tyr His Asp
        755                 760                 765

Asp Glu Thr Thr Asp Leu His Ile Phe Lys Val Leu Phe Arg Pro Val
    770                 775                 780

Val
785

<210> SEQ ID NO 25
<211> LENGTH: 784
<212> TYPE: PRT
<213> ORGANISM: Salvia sclarea

<400> SEQUENCE: 25

Met Thr Ser Val Asn Leu Ser Arg Ala Pro Ala Ile Ile Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Phe Thr Leu Ser Cys Gln Ile Arg Pro
        35                  40                  45

Lys Gln Leu Ser Gln Ile Ala Glu Leu Arg Val Thr Ser Leu Asp Ala
    50                  55                  60

Ser Gln Ala Ser Glu Lys Asp Ile Ser Leu Val Gln Thr Pro His Lys
65                  70                  75                  80

Val Glu Val Asn Glu Lys Ile Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His Gln Leu Ala Asp
    130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu Gln Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Gly Leu Pro
    210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
```

```
            325                 330                 335
Gly Ile Ser Arg Phe Phe Gln His Glu Ile Lys Tyr Phe Leu Asp His
            340                 345                 350
Ile Glu Ser Val Trp Glu Glu Thr Gly Val Phe Ser Gly Arg Tyr Thr
            355                 360                 365
Lys Phe Ser Asp Ile Asp Asp Thr Ser Met Gly Val Arg Leu Leu Lys
    370                 375                 380
Met His Gly Tyr Asp Val Asp Pro Asn Val Leu Lys His Phe Lys Gln
385                 390                 395                 400
Gln Asp Gly Lys Phe Ser Cys Tyr Ile Gly Gln Ser Val Glu Ser Ala
                405                 410                 415
Ser Pro Met Tyr Asn Leu Tyr Arg Ala Ala Gln Leu Arg Phe Pro Gly
            420                 425                 430
Glu Glu Val Leu Glu Glu Ala Thr Lys Phe Ala Phe Asn Phe Leu Gln
            435                 440                 445
Glu Met Leu Val Lys Asp Arg Leu Gln Glu Arg Trp Val Ile Ser Asp
        450                 455                 460
His Leu Phe Asp Glu Ile Lys Leu Gly Leu Lys Met Pro Trp Tyr Ala
465                 470                 475                 480
Thr Leu Pro Arg Val Glu Ala Ala Tyr Tyr Leu Asp His Tyr Ala Gly
                485                 490                 495
Ser Gly Asp Val Trp Ile Gly Lys Ser Phe Tyr Arg Met Pro Glu Ile
            500                 505                 510
Ser Asn Asp Thr Tyr Lys Glu Leu Ala Ile Leu Asp Phe Asn Arg Cys
            515                 520                 525
Gln Thr Gln His Gln Leu Glu Trp Ile Gln Met Gln Glu Trp Tyr Asp
        530                 535                 540
Arg Cys Ser Leu Ser Glu Phe Gly Ile Ser Lys Arg Glu Leu Leu Arg
545                 550                 555                 560
Ser Tyr Phe Leu Ala Ala Ala Thr Ile Phe Glu Pro Glu Arg Thr Gln
                565                 570                 575
Glu Arg Leu Leu Trp Ala Lys Thr Arg Ile Leu Ser Lys Met Ile Thr
            580                 585                 590
Ser Phe Val Asn Ile Ser Gly Thr Thr Leu Ser Leu Asp Tyr Asn Phe
        595                 600                 605
Asn Gly Leu Asp Glu Ile Ile Ser Ala Asn Glu Asp Gln Gly Leu Ala
    610                 615                 620
Gly Thr Leu Leu Ala Thr Phe His Gln Leu Leu Asp Gly Phe Asp Ile
625                 630                 635                 640
Tyr Thr Leu His Gln Leu Lys His Val Trp Ser Gln Trp Phe Met Lys
                645                 650                 655
Val Gln Gln Gly Glu Gly Ser Gly Gly Glu Asp Ala Val Leu Leu Ala
            660                 665                 670
Asn Thr Leu Asn Ile Cys Ala Gly Leu Asn Glu Asp Val Leu Ser Asn
        675                 680                 685
Asn Glu Tyr Thr Ala Leu Ser Thr Leu Thr Asn Lys Ile Cys Asn Arg
    690                 695                 700
Leu Ala Gln Ile Gln Asp Asn Lys Ile Leu Gln Val Val Asp Gly Ser
705                 710                 715                 720
Ile Lys Asp Lys Glu Leu Glu Gln Asp Met Gln Ala Leu Val Lys Leu
                725                 730                 735
Val Leu Gln Glu Asn Gly Gly Ala Val Asp Arg Asn Ile Arg His Thr
            740                 745                 750
```

```
Phe Leu Ser Val Ser Lys Thr Phe Tyr Tyr Asp Ala Tyr His Asp Asp
        755                 760                 765

Glu Thr Thr Asp Leu His Ile Phe Lys Val Leu Phe Arg Pro Val Val
    770                 775                 780
```

<210> SEQ ID NO 26
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 26
tatgatacng cngtnatdgc                                              20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tatgacacgg cagtgatcgc                                              20

<210> SEQ ID NO 28
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is a, c, g, or t

<400> SEQUENCE: 28
tatgacacgg cakkgrtngc                                              20

<210> SEQ ID NO 29
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 29
caactggctg atggntcntg ggg                                          23

<210> SEQ ID NO 30
<211> LENGTH: 23
<212> TYPE: DNA
<213> ORGANISM: Artificial sequence
<220> FEATURE:
<223> OTHER INFORMATION: Primer

<400> SEQUENCE: 30
caactggctg atggctcatg ggg       23

<210> SEQ ID NO 31
<211> LENGTH: 26
<212> TYPE: DNA
<213> ORGANISM: Artificial sequence
<220> FEATURE:
<223> OTHER INFORMATION: Primer

<400> SEQUENCE: 31
gatcctccaa crtcrwarar rtcrtc       26

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
gatcctccac gtcgwagaag tcgtc       25

<210> SEQ ID NO 33
<211> LENGTH: 81
<212> TYPE: DNA
<213> ORGANISM: Salvia sclarea

<400> SEQUENCE: 33
ctgatgtttc tgtctacggc gccgccattt tcttgaagca ctaacttcac caacgcctgc       60
atatcctgtt ctagctcctt a       81

<210> SEQ ID NO 34
<211> LENGTH: 73
<212> TYPE: DNA
<213> ORGANISM: Salvia sclarea

<400> SEQUENCE: 34
attcctgcat atggatccac tccaactgat gttgtgtttg gcatctgttg aaatccaata       60
tcgcaagctc ctt       73

<210> SEQ ID NO 35
<211> LENGTH: 52
<212> TYPE: DNA
<213> ORGANISM: Salvia sclarea

<400> SEQUENCE: 35
tattattgaa aaaggagtga cgtacatcaa ggagaatgtg cataaactta aa       52

<210> SEQ ID NO 36
<211> LENGTH: 857
<212> TYPE: DNA
<213> ORGANISM: Salvia sclarea

<400> SEQUENCE: 36
atgtcaccac aaacagagac taaagcaagt gttggattca agcgggtgt taaagagtac       60

```
aaattgactt attatactcc tgaatacgaa accaaagata ctgatatctt ggcagcattc      120
cgagtaactc ctcaacccgg agttccgcct gaagaagcag gggccgcggt agctgccgaa      180
tcttctactg gtacatggac aactgtgtgg accgatggac ttaccagcct tgatcgttac      240
aaagggcgat gctaccacat tgagcccgtt cctggagaaa aagatcaata tatctgttat      300
gtagcttacc ctttagacct ttttgaagaa ggttctgtta ctaacatgtt tacttccatt      360
gtaggaaatg tatttggatt caaagcccta cgtgctctac gtctggaaga tctgcgaatt      420
cctgttgctt atgttaaaac tttccaaggc ccgcctcatg ggatccaagt tgagagagat      480
aaattgaaca gtacggtcg tcctctgctg ggatgtacta ttaaacctaa attgggggtta      540 tctgctaaaa actatggtag agcggtttat gaatgtcttc gcggtggact tgattttacc      600
aaagatgatg agaacgtgaa ctcccagcca tttatgcgtt ggagagaccg cttcttattt      660
tgtgccgaag caatttataa agcacaggct gaaacaggtg aaatcaaagg gcattacttg      720
aatgctactg cgggtacatg cgaagagatg atgaaaagag ctatatttgc tagagaattg      780
ggagttccta tcgtaatgca cgactactta acaggaggat tcaccgcaaa taccagtttg      840
gctcattatt gccgaga                                                    857

<210> SEQ ID NO 37
<211> LENGTH: 540
<212> TYPE: DNA
<213> ORGANISM: Salvia sclarea

<400> SEQUENCE: 37
aaagtatcca ctgctttaaa ttcaaacttg atttctttcc atacctcaca agcggcagct       60
agttcaggac tccatttgca agcttcacgg ataattgcat taccttcagc agcaagatca      120
cgtccttcat tacgagcttt tacacacgct tctacagcta ctcggttagc tacagcacct      180
ggtgcattac cccaagggtg tcctaaagtt cctccaccga actgtagtac ggaatcgtct      240
ccaaagatct cggtcagagc aggcatatgc caaacgtgaa taccccctga agccacagga      300
ataacacccg gcagggagac ccaatcttga gtgaaataaa taccgcgact tcggtctttt      360
tcaataaaat catcacgcag taaatcaaca aaacctaaag taatgtctct ctctccttca      420
agtttaccta ctacggtacc agagtgaata tgatctccac cggacagacg taacgcttta      480
gctagtacac ggaagtgcat accgtgattc ttctgtctat caataactgc atgcattgca      540

<210> SEQ ID NO 38
<211> LENGTH: 60
<212> TYPE: DNA
<213> ORGANISM: Salvia sclarea

<400> SEQUENCE: 38
atgttcgtct cgcatttgcc aaaacatctg tgcttgtaac aattatggat gattttttcg       60

<210> SEQ ID NO 39
<211> LENGTH: 35
<212> TYPE: DNA
<213> ORGANISM: Salvia sclarea

<400> SEQUENCE: 39
cttctacctt ggcctgcatt cttgctctta aaaaa                                  35

<210> SEQ ID NO 40
<211> LENGTH: 35
<212> TYPE: DNA
```

```
<213> ORGANISM: Salvia sclarea

<400> SEQUENCE: 40
aaaaaaaata tgatctaaaa aatggatcag tttaa                                35

<210> SEQ ID NO 41
<211> LENGTH: 72
<212> TYPE: DNA
<213> ORGANISM: Salvia sclarea

<400> SEQUENCE: 41
actactcatg caatggcatt taggcttttg cgagtgaaag gatacgaagt ttcatcagag    60
gagttggcct ca                                                        72

<210> SEQ ID NO 42
<211> LENGTH: 35
<212> TYPE: DNA
<213> ORGANISM: Salvia sclarea

<400> SEQUENCE: 42
gcaactgatg attttgtgga tgttgggggc agctc                               35

<210> SEQ ID NO 43
<211> LENGTH: 35
<212> TYPE: DNA
<213> ORGANISM: Salvia sclarea

<400> SEQUENCE: 43
gccaaaataa ttccttgcat ggctttggaa ggaga                               35

<210> SEQ ID NO 44
<211> LENGTH: 11
<212> TYPE: PRT
<213> ORGANISM: Salvia sclarea

<400> SEQUENCE: 44

Ser Thr Leu Ala Cys Ile Leu Ala Leu Lys Lys
1               5                   10

<210> SEQ ID NO 45
<211> LENGTH: 10
<212> TYPE: PRT
<213> ORGANISM: Salvia sclarea

<400> SEQUENCE: 45

Lys Lys Tyr Asp Leu Lys Asn Gly Ser Val
1               5                   10

<210> SEQ ID NO 46
<211> LENGTH: 24
<212> TYPE: PRT
<213> ORGANISM: Salvia sclarea

<400> SEQUENCE: 46

Thr Thr His Ala Met Ala Phe Arg Leu Leu Arg Val Lys Gly Tyr Glu
1               5                   10                  15

Val Ser Ser Glu Glu Leu Ala Ser
            20

<210> SEQ ID NO 47
<211> LENGTH: 11
<212> TYPE: PRT
<213> ORGANISM: Salvia sclarea
```

<400> SEQUENCE: 47

Ala Thr Asp Asp Phe Val Asp Val Gly Gly Ser
1               5                   10

<210> SEQ ID NO 48
<211> LENGTH: 11
<212> TYPE: PRT
<213> ORGANISM: Salvia sclarea

<400> SEQUENCE: 48

Leu Leu Pro Lys Pro Cys Lys Glu Leu Phe Trp
1               5                   10

<210> SEQ ID NO 49
<211> LENGTH: 27
<212> TYPE: DNA
<213> ORGANISM: Artificial sequence
<220> FEATURE:
<223> OTHER INFORMATION: Primer

<400> SEQUENCE: 49
cttctacctt ggcctgcatt cttgctc                                27

<210> SEQ ID NO 50
<211> LENGTH: 27
<212> TYPE: DNA
<213> ORGANISM: Artificial sequence
<220> FEATURE:
<223> OTHER INFORMATION: Primer

<400> SEQUENCE: 50
gagcaagaat gcaggccaag gtagaag                                27

<210> SEQ ID NO 51
<211> LENGTH: 31
<212> TYPE: DNA
<213> ORGANISM: Artificial sequence
<220> FEATURE:
<223> OTHER INFORMATION: Primer

<400> SEQUENCE: 51
ctactcatgc aatggcattt aggcttttgc g                           31

<210> SEQ ID NO 52
<211> LENGTH: 33
<212> TYPE: DNA
<213> ORGANISM: Salvia sclarea

<400> SEQUENCE: 52
gtgaaaggat acgaagtttc atcagaggag ttg                         33

<210> SEQ ID NO 53
<211> LENGTH: 32
<212> TYPE: DNA
<213> ORGANISM: Artificial sequence
<220> FEATURE:
<223> OTHER INFORMATION: Primer

<400> SEQUENCE: 53
gaggccaact cctctgatga aacttcgtat cc                          32

<210> SEQ ID NO 54
<211> LENGTH: 30
<212> TYPE: DNA

<210> SEQ ID NO 54
<211> LENGTH: 30
<212> TYPE: DNA
<213> ORGANISM: Artificial sequence
<220> FEATURE:
<223> OTHER INFORMATION: Primer

<400> SEQUENCE: 54
cactcgcaaa agcctaaatg ccattgcatg                                    30

<210> SEQ ID NO 55
<211> LENGTH: 29
<212> TYPE: DNA
<213> ORGANISM: Artificial sequence
<220> FEATURE:
<223> OTHER INFORMATION: Primer

<400> SEQUENCE: 55
ctgatgattt tgtggatgtt gggggcagc                                     29

<210> SEQ ID NO 56
<211> LENGTH: 29
<212> TYPE: DNA
<213> ORGANISM: Artificial sequence
<220> FEATURE:
<223> OTHER INFORMATION: Primer

<400> SEQUENCE: 56
gctgccccca acatccacaa aatcatcag                                     29

<210> SEQ ID NO 57
<211> LENGTH: 33
<212> TYPE: DNA
<213> ORGANISM: Artificial sequence
<220> FEATURE:
<223> OTHER INFORMATION: Primer

<400> SEQUENCE: 57
ctccttccaa agccatgcaa ggaattattt tgg                                33

<210> SEQ ID NO 58
<211> LENGTH: 33
<212> TYPE: DNA
<213> ORGANISM: Artificial sequence
<220> FEATURE:
<223> OTHER INFORMATION: Primer

<400> SEQUENCE: 58
ccaaaataat tccttgcatg gctttggaag gag                                33

<210> SEQ ID NO 59
<211> LENGTH: 24
<212> TYPE: DNA
<213> ORGANISM: Artificial sequence
<220> FEATURE:
<223> OTHER INFORMATION: Primer

<400> SEQUENCE: 59
gcgtatctga ttcctgccct ttgc                                          24

<210> SEQ ID NO 60
<211> LENGTH: 28
<212> TYPE: DNA
<213> ORGANISM: Artificial sequence
<220> FEATURE:
<223> OTHER INFORMATION: Primer

<400> SEQUENCE: 60
gtttaattcc atagggggatt tcttcaag                                     28

<210> SEQ ID NO 61
<211> LENGTH: 24
<212> TYPE: DNA
<213> ORGANISM: Artificial sequence
<220> FEATURE:
<223> OTHER INFORMATION: Primer

<400> SEQUENCE: 61
atgtcgcttc ctctctccac ttgc                                          24

<210> SEQ ID NO 62
<211> LENGTH: 32
<212> TYPE: DNA
<213> ORGANISM: Artificial sequence
<220> FEATURE:
<223> OTHER INFORMATION: Primer

<400> SEQUENCE: 62
cgaatgggtt tctcttttat atatagatac ag                                 32

<210> SEQ ID NO 63
<211> LENGTH: 28
<212> TYPE: DNA
<213> ORGANISM: Artificial sequence
<220> FEATURE:
<223> OTHER INFORMATION: Primer

<400> SEQUENCE: 63
ttatatcctt gctcctgttt gttccttg                                      28

<210> SEQ ID NO 64
<211> LENGTH: 32
<212> TYPE: DNA
<213> ORGANISM: Artificial sequence
<220> FEATURE:
<223> OTHER INFORMATION: Primer

<400> SEQUENCE: 64
tcaaaagaca aggatttca tatcttcctt gg                                  32

<210> SEQ ID NO 65
<211> LENGTH: 26
<212> TYPE: DNA
<213> ORGANISM: Artificial sequence
<220> FEATURE:
<223> OTHER INFORMATION: Primer

<400> SEQUENCE: 65
caccctaata tcacccgtac caaacg                                        26

<210> SEQ ID NO 66
<211> LENGTH: 36
<212> TYPE: DNA
<213> ORGANISM: Artificial sequence
<220> FEATURE:
<223> OTHER INFORMATION: Primer

<400> SEQUENCE: 66
cctatagtgt caaaagacaa aggatttcat atcttc                             36

<210> SEQ ID NO 67
<211> LENGTH: 31
<212> TYPE: DNA
<213> ORGANISM: Artificial sequence
<220> FEATURE:

```
<223> OTHER INFORMATION: Primer

<400> SEQUENCE: 67
gcttattgag aaagatggta gtccaagcaa g                              31

<210> SEQ ID NO 68
<211> LENGTH: 32
<212> TYPE: DNA
<213> ORGANISM: Artificial sequence
<220> FEATURE:
<223> OTHER INFORMATION: Primer

<400> SEQUENCE: 68
gctctataaa gctcaataat catcggcagg tc                             32

<210> SEQ ID NO 69
<211> LENGTH: 39
<212> TYPE: DNA
<213> ORGANISM: Artificial sequence
<220> FEATURE:
<223> OTHER INFORMATION: Primer

<400> SEQUENCE: 69
ccacaacctg aatgtgttat ctagaatagt gttgatttc                      39

<210> SEQ ID NO 70
<211> LENGTH: 32
<212> TYPE: DNA
<213> ORGANISM: Artificial sequence
<220> FEATURE:
<223> OTHER INFORMATION: Primer

<400> SEQUENCE: 70
ggaagaattg atcgaccccc aacctttgaa gg                             32

<210> SEQ ID NO 71
<211> LENGTH: 34
<212> TYPE: DNA
<213> ORGANISM: Artificial sequence
<220> FEATURE:
<223> OTHER INFORMATION: Primer

<400> SEQUENCE: 71
ggcaatgtta ctactcatgc aatggcattt aggc                           34

<210> SEQ ID NO 72
<211> LENGTH: 34
<212> TYPE: DNA
<213> ORGANISM: Artificial sequence
<220> FEATURE:
<223> OTHER INFORMATION: Primer

<400> SEQUENCE: 72
gcctaaatgc cattgcatga gtagtaacat tgcc                           34

<210> SEQ ID NO 73
<211> LENGTH: 28
<212> TYPE: DNA
<213> ORGANISM: Artificial sequence
<220> FEATURE:
<223> OTHER INFORMATION: Primer

<400> SEQUENCE: 73
ggtggtcaca ggaaatcctt ggactgga                                  28
```

```
<210> SEQ ID NO 74
<211> LENGTH: 25
<212> TYPE: DNA
<213> ORGANISM: Artificial sequence
<220> FEATURE:
<223> OTHER INFORMATION: Primer

<400> SEQUENCE: 74
cctgctccca actctttggc cggag                                    25

<210> SEQ ID NO 75
<211> LENGTH: 28
<212> TYPE: DNA
<213> ORGANISM: Artificial sequence
<220> FEATURE:
<223> OTHER INFORMATION: Primer

<400> SEQUENCE: 75
cgtaactccg acgttgaagg cgagcgac                                 28

<210> SEQ ID NO 76
<211> LENGTH: 23
<212> TYPE: DNA
<213> ORGANISM: Artificial sequence
<220> FEATURE:
<223> OTHER INFORMATION: Primer

<400> SEQUENCE: 76
caccatgtcg ctcgccttca acg                                      23

<210> SEQ ID NO 77
<211> LENGTH: 33
<212> TYPE: DNA
<213> ORGANISM: Artificial sequence
<220> FEATURE:
<223> OTHER INFORMATION: Primer

<400> SEQUENCE: 77
caccatggcg aaaatgaaag agaatttcaa gag                           33

<210> SEQ ID NO 78
<211> LENGTH: 24
<212> TYPE: DNA
<213> ORGANISM: Artificial sequence
<220> FEATURE:
<223> OTHER INFORMATION: Primer

<400> SEQUENCE: 78
caccatgtcg cttcctctct ccac                                     24

<210> SEQ ID NO 79
<211> LENGTH: 27
<212> TYPE: DNA
<213> ORGANISM: Artificial sequence
<220> FEATURE:
<223> OTHER INFORMATION: Primer

<400> SEQUENCE: 79
caccatggaa actgggcttc aaactgc                                  27

<210> SEQ ID NO 80
<211> LENGTH: 30
<212> TYPE: DNA
<213> ORGANISM: Artificial sequence
<220> FEATURE:
<223> OTHER INFORMATION: Primer
```

<400> SEQUENCE: 80

```
ttatatcctt gctcctgttt gttccttgag                                    30
```

<210> SEQ ID NO 81
<211> LENGTH: 547
<212> TYPE: DNA
<213> ORGANISM: Salvia sclarea

<400> SEQUENCE: 81

```
agcggccgct gaattctaga atttggatgt ggaatagaat tgacgaatgg cgtgcaagcg    60
cgcctctctc ctctctcctc tctctagaaa atatgattgt gcagttgagt tggcaaaagc   120
gtatctgatt cctgcccttt gctaactttc ccaaattttg tcccgtttaa ttccataggg   180
gatttcttca aggccgccat gtcgcttcct ctctccactt gcaatggatc acattttcgg   240
agataccgct tgtctcctgc ttcagcagct tctatggaaa ctgggcttca aactgctact   300
tcagcaaaaa tcgcctctat gccagcgtgc tttgaggaga cgagagggag atagcaaag    360
ttgtttcata aggatgaact ttctgtgtcg acatatgata cagcatgggt tgccatggtc   420
ccttctccaa cttcgttaga ggaaccttgc ttccccgatt gtctaaactg gttgctcgag   480
aaccagtgcc atgatggttc gtgggcccgt ccccaccatc actctttgct aatgaaagat   540
gtccttt                                                            547
```

<210> SEQ ID NO 82
<211> LENGTH: 1473
<212> TYPE: DNA
<213> ORGANISM: Salvia sclarea

<400> SEQUENCE: 82

```
ctccatatgg taaccaagag gctgttagcc agcaaacaaa tgacctgccg atgattattg    60
agctttatag agcagcaaat gagagaatat atgaagaaga gaggagtctt gaaaaaattc   120
ttgcttggac taccatcttt ctcaataagc aagtgcaaga taactcaatt cccgacaaaa   180
aactgcacaa actggtggaa ttctacttga ggaattacaa aggcataacc ataagattgg   240
gagctagacg aaacctcgag ctatatgaca tgacctacta tcaagctctg aaatctacaa   300
acaggttctc taatttatgc aacgaagatt ttctagtttt cgcaaagcaa gatttcgata   360
tacatgaagc ccagaaccag aaaggacttc aacaactgca aggtggtat gcagattgta   420
ggttggacac cttaaacttt ggaagagatg tagttattat tgctaattat ttggcttcat   480
taattattgg tgatcatgcg tttgactatg ttcgtctcgc atttgccaaa acatctgtgc   540
ttgtaacaat tatggatgat tttttcgact gtcatggctc tagtcaagag tgtgacaaga   600
tcattgaatt agtaaaagaa tggaaggaga atccggatgc agagtacgga tctgaggagc   660
ttgagatcct ttttatggcg ttgtacaata cagtaaatga gttggcggag agggctcgtg   720
ttgaacaggg gcgtagtgtc aaagagtttc tagtcaaact gtgggttgaa atactctcag   780
cttttcaagat agaattagat acatggagca atggcacgca gcaaagcttc gatgaataca   840
tttcttcgtc gtggttgtcg aacggttccc ggctgacagg tctcctgacg atgcaattcg   900
tcggagtaaa attgtccgat gaaatgctta tgagtgaaga gtgcactgat ttggctaggc   960
atgtctgtat ggtcggccgg ctgctcaacg acgtgtgcag ttctgagagg gagcgcgagg  1020
aaaatattgc aggaaaaagt tatagcattc tactagcaac tgagaaagat ggaagaaaag  1080
ttagtgaaga tgaagccatt gcagagatca atgaaatggt tgaatatcac tggagaaaag  1140
tgttgcagat tgtgtataaa aagaaaagca ttttgccaag aagatgcaaa gatgtatttt  1200
```

| | |
|---|---|
| tggagatggc taagggtacg ttttatgctt atgggatcaa cgatgaattg acttctcctc | 1260 |
| agcaatccaa ggaagatatg aaatcctttg tcttttgaca ctataggctc gtttggtacg | 1320 |
| ggtgatatta gggtgtgtaa tacaattatg acactgtaat attttattt gtacaaaaca | 1380 |
| cgtggttctt tgcatatcaa aaatttgaaa atgttataag gatttgtatc cactataaga | 1440 |
| aattgttgga taaaaaaaaa aaaaaaaaa aaa | 1473 |

<210> SEQ ID NO 83
<211> LENGTH: 207
<212> TYPE: DNA
<213> ORGANISM: Salvia sclarea

<400> SEQUENCE: 83

| | |
|---|---|
| cacatgtgct ccgtggtcca tctattctac agtaaagacg acggattcac ctcgcaggat | 60 |
| ttgattcaag ttgtaaatgc aattattcac aaacctattg tcctcaagga acaaacagga | 120 |
| gcaaggatat aattttttta atctgtatct atatataaaa gagaaaccca ttcgttaaaa | 180 |
| taaaaaaaaa aaaaaaaaa aaaaaaa | 207 |

<210> SEQ ID NO 84
<211> LENGTH: 464
<212> TYPE: DNA
<213> ORGANISM: Salvia sclarea

<400> SEQUENCE: 84

| | |
|---|---|
| aaattaatta ggaataaaaa aaattggact ttatatttat tagaaacggc cgccgccgca | 60 |
| aaaaaatgtc gctcgccttc aacgtcggag ttacgccttt ctccggccaa agagttggga | 120 |
| gcaggaaaga aaaatttcca gtccaaggat ttcctgtgac cacccccaat aggtcacgtc | 180 |
| tcatcgttaa ctgcagcctt actacaatag atttcatggc gaaaatgaaa gagaatttca | 240 |
| agagggaaga cgataaattt ccaacgacaa cgactcttcg atccgaagat atacctcta | 300 |
| atttgtgtat aatcgacacc cttcaaaggt tgggggtcga tcaattcttc caatatgaaa | 360 |
| tcaacactat tctagataac acattcaggt tgtggcaaga aaacacaaa gttatatatg | 420 |
| gcaatgttac tactcatgca atggcattta ggcttttgcg agtg | 464 |

<210> SEQ ID NO 85
<211> LENGTH: 2388
<212> TYPE: DNA
<213> ORGANISM: Salvia sclarea

<400> SEQUENCE: 85

| | |
|---|---|
| atgtcgcttc ctctctccac ttgcaatgga tcacattttc ggagataccg cttgtctcct | 60 |
| gcttcagctt ctatggaaac tgggcttcaa actgctactt cagcaaaaat cgcctctatg | 120 |
| ccagcgtgct ttgaggagac gagagggagg atagcaaagt tgtttcataa ggatgaactt | 180 |
| tctgtgtcga catatgatac agcatggggt gccatggtcc cttctccaac ttcgttagag | 240 |
| gaaccttgct tccccgattg tctaaactgg ttgctcgaga accagtgcca tgatggttcg | 300 |
| tgggcccgtc cccaccatca ctctttgcta atgaaagatg tcctttcttc taccttggcc | 360 |
| tgcattcttg ctcttaaaaa atggggagtt ggtgaaaaac agattaacag ggcttgcat | 420 |
| tttatggagt tgaattttgc ttcagctact gagaagtgtc agattactcc catgggattt | 480 |
| gatattgtat ttcctgccat gcttgattat gccagagact tctctttgga catgcattta | 540 |
| gagccaacta cgttgaatga tttgatacat aagagggatt tggagcttaa aagcaagcca | 600 |

-continued

```
gatttttcat cggatgggga agcctattgg gcatatatag ctgaaggaat ggggaattta    660
cggaactggg aatcagttat gaaatatcaa agaaggaatg gatctctttt caactgtcct    720
tccacgacag cagctgcttt tgttgcactg gcaattctg actgcctcaa ctacctgcat     780
tcagccttaa agaagtttgg gaatgcagtt cctgcagttt atcctctaga tatatattct    840
cacctgtgca tagttgacaa tcttgaaagg ttggggatca gccgttattt tttgactgag    900
attcaaagcg tgttagatga aacacacaga tgttggatgc agggcaatga agagatcttc    960
atggatgcct caacttgtgc tttagctttc cggatattgc gattgaacgg atacgatgta    1020
acttcagatc cggttacaaa aattcaacac gagtgctttt cgagttcctt catggaaat    1080 gtgatggaca ttaacacgac tcttgaatta tagggcat ctgaactcat actatatcca      1140
gatgaaagag atctagtgag acaaaattta aggcttaaac aaatactaga gcaagagcta    1200
tccaatggtt ttattcaatc atgtcaactt ggaagaagtg ttaatgcaga ggtgaaccag    1260
gctatcgagt atccatttta tgcaattatg acagggttg caaaacggaa aaatatagag     1320
aactacaact ttgataatac aagaattctg aaaacttcat attgttcacc aaattttggc    1380
aacaaggatt ttcttttttct gtccgtagag gacttcaatc tgtgtcaagc cacacatcgc    1440
gaagaactca gggaacttga agatgggtc gtagagaata gattggacga gctgcagttt     1500
gcaaggagta agtctgcata ttgttatttt tctgcagcag caacccttttc tgctccagaa   1560 ctacgtgatg cacgcatgtc gtgggccaaa ggtggtgttc tgactacagt gattgatgac    1620 tttttttgacg tcggaggttc tatggaagaa ttgaagaact taattcattt ggttgaaaaa    1680
tgggatgtgg atgttagcac agaatgctct cccataatg tccagataat attttcagca     1740
cttaagagca caatccgtga aattggatac aaagggttga agctacaagg gcgttgtatt    1800
actaaccata taattggcat ttggttagat ttgctgaatt ctatgatgaa agaaactgaa    1860
tgggctagag acaactatgt cccaacaatt gatgaatata tgagcaatgc atatgtgtca    1920
tttgctctgg ggccaattgt tctgccaact ctatatcttg ttgggccgaa gctctcagaa    1980
gagatggcaa accaccccga gtactataaa ctattcaaat tgatgagcac atgcggacgc    2040
cttttaaatg acatccgtgg ttatgagaga gaactcaaag atggtaaact gaacgcgcta    2100
tctttgtaca tggctaatca tggtggtgaa gtaagtaaag aagcagccat tcagagatc     2160 aaaagttgga ttgagagcag taggagagaa ttactgagat tagttttgga ggggaagaag    2220
agtgtccttc caaagccatg caaggaatta ttttggcaca tgtgctctgt ggtccatcta    2280
ttctacagta aagacgacgg attcacctcg caggatttga ttcaagttgt aaatgcaatt    2340
attcacaaac ctattgtcct caaggaacaa acaggagcaa ggatataa                 2388
```

<210> SEQ ID NO 86
<211> LENGTH: 795
<212> TYPE: PRT
<213> ORGANISM: Salvia sclarea

<400> SEQUENCE: 86

```
Met Ser Leu Pro Leu Ser Thr Cys Asn Gly Ser His Phe Arg Arg Tyr
1               5                   10                  15

Arg Leu Ser Pro Ala Ser Ala Ser Met Glu Thr Gly Leu Gln Thr Ala
            20                  25                  30

Thr Ser Ala Lys Ile Ala Ser Met Pro Ala Cys Phe Glu Glu Thr Arg
        35                  40                  45

Gly Arg Ile Ala Lys Leu Phe His Lys Asp Glu Leu Ser Val Ser Thr
    50                  55                  60
```

```
Tyr Asp Thr Ala Trp Val Ala Met Val Pro Ser Pro Thr Ser Leu Glu
 65                  70                  75                  80

Glu Pro Cys Phe Pro Asp Cys Leu Asn Trp Leu Leu Glu Asn Gln Cys
                 85                  90                  95

His Asp Gly Ser Trp Ala Arg Pro His His Ser Leu Leu Met Lys
            100                 105                 110

Asp Val Leu Ser Ser Thr Leu Ala Cys Ile Leu Ala Leu Lys Lys Trp
            115                 120                 125

Gly Val Gly Glu Lys Gln Ile Asn Arg Gly Leu His Phe Met Glu Leu
            130                 135                 140

Asn Phe Ala Ser Ala Thr Glu Lys Cys Gln Ile Thr Pro Met Gly Phe
145                 150                 155                 160

Asp Ile Val Phe Pro Ala Met Leu Asp Tyr Ala Arg Asp Phe Ser Leu
                165                 170                 175

Asp Met His Leu Glu Pro Thr Thr Leu Asn Asp Leu Ile His Lys Arg
            180                 185                 190

Asp Leu Glu Leu Lys Ser Lys Pro Asp Phe Ser Ser Asp Gly Glu Ala
            195                 200                 205

Tyr Trp Ala Tyr Ile Ala Glu Gly Met Gly Asn Leu Arg Asn Trp Glu
210                 215                 220

Ser Val Met Lys Tyr Gln Arg Arg Asn Gly Ser Leu Phe Asn Cys Pro
225                 230                 235                 240

Ser Thr Thr Ala Ala Ala Phe Val Ala Leu Gly Asn Ser Asp Cys Leu
                245                 250                 255

Asn Tyr Leu His Ser Ala Leu Lys Lys Phe Gly Asn Ala Val Pro Ala
            260                 265                 270

Val Tyr Pro Leu Asp Ile Tyr Ser His Leu Cys Ile Val Asp Asn Leu
            275                 280                 285

Glu Arg Leu Gly Ile Ser Arg Tyr Phe Leu Thr Glu Ile Gln Ser Val
            290                 295                 300

Leu Asp Glu Thr His Arg Cys Trp Met Gln Gly Asn Glu Glu Ile Phe
305                 310                 315                 320

Met Asp Ala Ser Thr Cys Ala Leu Ala Phe Arg Ile Leu Arg Leu Asn
                325                 330                 335

Gly Tyr Asp Val Thr Ser Asp Pro Val Thr Lys Ile Gln His Glu Cys
            340                 345                 350

Phe Ser Ser Ser Phe His Gly Asn Val Met Asp Ile Asn Thr Thr Leu
            355                 360                 365

Glu Leu Tyr Arg Ala Ser Glu Leu Ile Leu Tyr Pro Asp Glu Arg Asp
            370                 375                 380

Leu Val Arg Gln Asn Leu Arg Leu Lys Gln Ile Leu Glu Gln Glu Leu
385                 390                 395                 400

Ser Asn Gly Phe Ile Gln Ser Cys Gln Leu Gly Arg Ser Val Asn Ala
                405                 410                 415

Glu Val Asn Gln Ala Ile Glu Tyr Pro Phe Tyr Ala Ile Met Asp Arg
            420                 425                 430

Val Ala Lys Arg Lys Asn Ile Glu Asn Tyr Asn Phe Asp Asn Thr Arg
            435                 440                 445

Ile Leu Lys Thr Ser Tyr Cys Ser Pro Asn Phe Gly Asn Lys Asp Phe
            450                 455                 460

Leu Phe Leu Ser Val Glu Asp Phe Asn Leu Cys Gln Ala Thr His Arg
465                 470                 475                 480
```

Glu Glu Leu Arg Glu Leu Glu Arg Trp Val Val Glu Asn Arg Leu Asp
                485                 490                 495

Glu Leu Gln Phe Ala Arg Ser Lys Ser Ala Tyr Cys Tyr Phe Ser Ala
            500                 505                 510

Ala Ala Thr Phe Ser Ala Pro Glu Leu Arg Asp Ala Arg Met Ser Trp
            515                 520                 525

Ala Lys Gly Gly Val Leu Thr Thr Val Ile Asp Asp Phe Phe Asp Val
            530                 535                 540

Gly Gly Ser Met Glu Glu Leu Lys Asn Leu Ile His Leu Val Glu Lys
545                 550                 555                 560

Trp Asp Val Asp Val Ser Thr Glu Cys Ser Ser His Asn Val Gln Ile
                565                 570                 575

Ile Phe Ser Ala Leu Lys Ser Thr Ile Arg Glu Ile Gly Tyr Lys Gly
            580                 585                 590

Leu Lys Leu Gln Gly Arg Cys Ile Thr Asn His Ile Gly Ile Trp
            595                 600                 605

Leu Asp Leu Leu Asn Ser Met Met Lys Glu Thr Glu Trp Ala Arg Asp
610                 615                 620

Asn Tyr Val Pro Thr Ile Asp Glu Tyr Met Ser Asn Ala Tyr Val Ser
625                 630                 635                 640

Phe Ala Leu Gly Pro Ile Val Leu Pro Thr Leu Tyr Leu Val Gly Pro
            645                 650                 655

Lys Leu Ser Glu Glu Met Ala Asn His Pro Glu Tyr Tyr Lys Leu Phe
            660                 665                 670

Lys Leu Met Ser Thr Cys Gly Arg Leu Leu Asn Asp Ile Arg Gly Tyr
            675                 680                 685

Glu Arg Glu Leu Lys Asp Gly Lys Leu Asn Ala Leu Ser Leu Tyr Met
            690                 695                 700

Ala Asn His Gly Gly Glu Val Ser Lys Glu Ala Ala Ile Ser Glu Ile
705                 710                 715                 720

Lys Ser Trp Ile Glu Ser Ser Arg Arg Glu Leu Leu Arg Leu Val Leu
                725                 730                 735

Glu Gly Lys Lys Ser Val Leu Pro Lys Pro Cys Lys Glu Leu Phe Trp
            740                 745                 750

His Met Cys Ser Val Val His Leu Phe Tyr Ser Lys Asp Asp Gly Phe
            755                 760                 765

Thr Ser Gln Asp Leu Ile Gln Val Val Asn Ala Ile Ile His Lys Pro
            770                 775                 780

Ile Val Leu Lys Glu Gln Thr Gly Ala Arg Ile
785                 790                 795

<210> SEQ ID NO 87
<211> LENGTH: 536
<212> TYPE: DNA
<213> ORGANISM: Salvia sclarea

<400> SEQUENCE: 87
aaattaatta ggaataaaaa aaattggact ttatatttat tagaaacggc cgccgccgca      60
aaaaaatgtc gctcgccttc aacgtcggag ttacgccttt ctccggccaa agagttggga     120
gcaggaaaga aaaatttcca gtccaaggat ttcctgtgac cacccccaat aggtcacgtc     180
tcatcgttaa ctgcagcctt actacaatag atttcatggc gaaaatgaaa gagaatttca     240
agagggaaga cgataaattt ccaacgacaa cgactcttcg atccgaagat ataccctcta     300
atttgtgtat aatcgacacc cttcaaaggt tgggggtcga tcaattcttc caatatgaaa     360

```
tcaacactat tctagataac acattcaggt tgtggcaaga aaaacacaaa gttatatatg    420
gcaatgttac tactcatgca atggcattta ggcttttgcg agtgaaagga tacgaagttt    480
catcagagga gttggctcca tatggtaacc aagaggctgt tagccagcaa acaaat       536

<210> SEQ ID NO 88
<211> LENGTH: 95
<212> TYPE: DNA
<213> ORGANISM: Salvia sclarea

<400> SEQUENCE: 88
ttgcatcttc ttggcaaaat gctttctttt ttatacacaa tctgcaacac ttttctccag    60
tgatattcaa ccatttcatt gatctctgca atggc                               95

<210> SEQ ID NO 89
<211> LENGTH: 55
<212> TYPE: DNA
<213> ORGANISM: Salvia sclarea

<400> SEQUENCE: 89
tgaagcccag aaccagaaag gacttcaaca actgcaaagg tggtatgcag attgt         55

<210> SEQ ID NO 90
<211> LENGTH: 53
<212> TYPE: DNA
<213> ORGANISM: Salvia sclarea

<400> SEQUENCE: 90
tactctgcat ccggattctc cttccattct tttactaatt caatgatctt gtc           53

<210> SEQ ID NO 91
<211> LENGTH: 2391
<212> TYPE: DNA
<213> ORGANISM: Salvia sclarea

<400> SEQUENCE: 91
atgtcgcttc ctctctccac ttgcaatgga tcacattttc ggagataccg cttgtctcct    60
gcttcagctt ctatggaaac tgggcttcaa actgctactt cagcaaaaat cgcctctatg   120
ccagcgtgct ttgaggagac gagagggagg atagcaaagt tgtttcataa ggatgaactt   180
tctgtgtcga catatgatac agcatgggtt gccatggtcc cttctccaac ttcgttagag   240
gaaccttgct tccccgattg tctaaactgg ttgctcgaga accagtgcca tgatggttcg   300
tgggcccgtc cccaccatca ctctttgcta atgaaagatg tccttttcttc taccttggcc   360 tgcattcttg ctcttaaaaa atggggagtt ggtgaaaaac agattaacag gggcttgcat   420
tttatggagt tgaattttgc ttcagctact gagaagtgtc agattactcc catgggattt   480
gatattgtat ttcctgccat gcttgattat gccagagact tctctttgga catgcattta   540
gagccaacta cgttgaatga tttgatacat aagagggatt tggagcttaa aagcaagcca   600 gattttttcat cggatgggga agcctattgg gcatatatag ctgaaggaat ggggaattta   660
cggaactggg aatcagttat gaaatatcaa agaaggaatg gatctctttt caactgtcct   720
tccacgacag cagctgcttt tgttgcactg ggcaattctg actgcctcaa ctacctgcat   780
tcagccttaa agaagtttgg gaatgcagtt cctgcagttt atcctctaga tatatattct   840
cacctgtgca tagttgacaa tcttgaaagg tggggatca gccgttattt tttgactgag   900
attcaaagcg tgttagatga aacacacaga tgttggatgc agggcaatga agagatcttc   960
```

```
atggatgcct caacttgtgc tttagctttc cggatattgc gattgaacgg atacgatgta   1020
acttcagatc cggttacaaa aattcaacac gagtgctttt cgagttcctt tcatggaaat   1080
gtgatggaca ttaacacgac tcttgaatta tagggcat ctgaactcat actatatcca    1140
gatgaaagag atctagtgag acaaaattta aggcttaaac aaatactaga gcaagagcta   1200
tccaatggtt ttattcaatc atgtcaactt ggaagaagtg ttaatgcaga ggtgaaccag   1260
gctatcgagt atccatttta tgcaattatg gacaggttg caaaacggaa aaatatagag    1320
aactacaact ttgataatac aagaattctg aaaacttcat attgttcacc aaattttggc   1380
aacaaggatt ttcttttcct gtccgtagag gacttcaatc tgtgtcaagc cacacatcgc   1440
gaagaactca gggaacttga agatgggtc gtagagaata gattggacga gctgcagttt    1500
gcaaggagta agtctgcata ttgttatttt tctgcagcag caaccttttc tgctccagaa   1560
ctacgtgatg cacgcatgtc gtgggccaaa ggtggtgttc tgactacagt gattgatgac   1620 tttttgacg tcggaggttc tatgaagaa ttgaagaact taattcattt ggttgaaaaa     1680
tgggatgtgg atgttagcac agaatgctct tcccataatg tccagataat attttcagca   1740
cttaagagca caatccgtga aattggatac aaagggttga agctacaagg gcgttgtatt   1800
actaaccata taattggcat ttggttagat ttgctgaatt ctatgatgaa agaaactgaa   1860
tgggctagag acaactatgt cccaacaatt gatgaatata tgagcaatgc atatgtgtca   1920
tttgctctgg ggccaattgt tctgccaact ctatatcttg ttgggccgaa gctctcagaa   1980
gagatggcaa ccaccccga gtactataaa ctattcaaat tgatgagcac atgcggacgc    2040
cttttaaatg acatccgtgg ttatgagaga gaactcaaag atggtaaact gaacgcgcta   2100
tctttgtaca tggctaatca tggtggtgaa gtaagtaaag aagcagccat ttcagagatc   2160
aaaagttgga ttgagagcag taggagagaa ttactgagat tagttttgga ggggaagaag   2220
agtgtccttc caaagccatg caaggaatta ttttggcaca tgtgctctgt ggtccatcta   2280
ttctacagta aagacgacgg attcacctcg caggatttga ttcaagttgt aaatgcaatt   2340
attcacaaac ctattgtcct caaggaacaa acaggagcaa ggatataaaa g            2391
```

<210> SEQ ID NO 92
<211> LENGTH: 2316
<212> TYPE: DNA
<213> ORGANISM: Salvia sclarea

<400> SEQUENCE: 92

```
atggaaactg gcttcaaaac tgctacttca gcaaaaatcg cctctatgcc agcgtgctttt    60 gaggagacga gagggaggat agcaaagttg tttcataagg atgaactttc tgtgtcgaca   120
tatgatacag catgggttgc catggtccct tctccaactt cgttagagga accttgcttc   180
cccgattgtc taaactggtt gctcgagaac cagtgccatg atggttcgtg ggcccgtccc   240
caccatcact ctttgctaat gaaagatgtc ctttcttcta ccttggcctg cattcttgct   300
cttaaaaaat ggggagttgg tgaaaaacag attaacaggg gcttgcattt tatggagttg   360
aattttgctt cagctactga gaagtgtcag attactccca tgggatttga tattgtatttt   420 cctgccatgc ttgattatgc cagagacttc tcttttggaca tgcatttaga gccaactacg   480
ttgaatgatt tgatacataa gagggatttg gagcttaaaa gcaagccaga ttttttcatcg   540 gatggggaag cctattgggc atatatagct gaaggaatgg ggaatttacg gaactgggaa   600
tcagttatga aatatcaaag aaggaatgga tctcttttca actgtccttc cacgacagca   660 gctgctttttg ttgcactggg caattctgac tgcctcaact acctgcattc agccttaaag   720
```

```
aagtttggga atgcagttcc tgcagtttat cctctagata tatattctca cctgtgcata    780
gttgacaatc ttgaaaggtt ggggatcagc cgttattttt tgactgagat tcaaagcgtg    840
ttagatgaaa cacacagatg ttggatgcag ggcaatgaag agatcttcat ggatgcctca    900
acttgtgctt tagcttttcg gatattgcga ttgaacggaa cgatgtaac ttcagatccg     960 gttacaaaaa ttcaacacga gtgcttttcg agttcctttc atggaaatgt gatggacatt   1020
aacacgactc ttgaattata tagggcatct gaactcatac tatatccaga tgaaagagat   1080
ctagtgagac aaaatttaag gcttaaacaa atactagagc aagagctatc caatggtttt   1140
attcaatcat gtcaacttgg aagaagtgtt aatgcagagg tgaaccaggc tatcgagtat   1200
ccattttatg caattatgga cagggttgca aaacggaaaa atatagagaa ctacaacttt   1260
gataatacaa gaattctgaa aacttcatat tgttcaccaa attttggcaa caaggatttt   1320 cttttttctgt ccgtagagga cttcaatctg tgtcaagcca cacatcgcga agaactcagg   1380
gaacttgaaa gatgggtcgt agagaataga ttggacgagc tgcagtttgc aaggagtaag   1440
tctgcatatt gttattttc tgcagcagca acctttctg ctccagaact acgtgatgca     1500
cgcatgtcgt gggccaaagg tggtgttctg actacagtga ttgatgactt ttttgacgtc   1560
ggaggttcta tggaagaatt gaagaactta attcatttgg ttgaaaaatg ggatgtggat   1620
gttagcacag aatgctcttc ccataatgtc cagataatat tttcagcact aagagcaca    1680 atccgtgaaa ttggatacaa agggttgaag ctacaagggc gttgtattac taaccatata   1740
attggcattt ggttagattt gctgaattct atgatgaaag aaactgaatg ggctagagac   1800
aactatgtcc caacaattga tgaatatatg agcaatgcat atgtgtcatt tgctctgggg   1860
ccaattgttc tgccaactct atatcttgtt gggccgaagc tctcagaaga gatggcaaac   1920 cacccgagt actataaact attcaaattg atgagcacat gcggacgcct tttaaatgac    1980
atccgtggtt atgagagaga actcaaagat ggtaaactga acgcgctatc tttgtacatg   2040
gctaatcatg gtggtgaagt aagtaaagaa gcagccattt cagagatcaa aagttggatt   2100
gagagcagta ggagagaatt actgagatta gttttggagg ggaagaagag tgtccttcca   2160
aagccatgca aggaattatt ttggcacatg tgctctgtgg tccatctatt ctacagtaaa   2220
gacgacggat tcacctcgca ggatttgatt caagttgtaa atgcaattat tcacaaacct   2280
attgtcctca aggaacaaac aggagcaagg atataa                             2316

<210> SEQ ID NO 93
<211> LENGTH: 1578
<212> TYPE: DNA
<213> ORGANISM: Salvia sclarea

<400> SEQUENCE: 93
atggcgaaaa tgaaagagaa tttcaagagg gaagacgata aatttccaac gacaacgact     60
cttcgatccg aagatatacc ctctaatttg tgtataatcg acacccttca aaggttgggg    120
gtcgatcaat tcttccaata tgaaatcaac actattctag ataacacatt caggttgtgg    180
caagaaaaac acaaagttat atatggcaat gttactactc atgcaatggc atttaggctt    240
ttgcgagtga aaggatacga agtttcatca gaggagttgg ctccatatgg taaccaagag    300
gctgttagcc agcaaacaaa tgacctgccg atgattattg agctttatag agcagcaaat    360 gagagaaatat atgaagaaga gaggagtctt gaaaaaattc ttgcttggac taccatcttt    420
ctcaataagc aagtgcaaga taactcaatt cccgacaaaa aactgcacaa actggtggaa    480
```

```
ttctacttga ggaattacaa aggcataacc ataagattgg gagctagacg aaacctcgag      540
ctatatgaca tgacctacta tcaagctctg aaatctacaa acaggttctc taatttatgc      600
aacgaagatt ttctagtttt cgcaaagcaa gatttcgata tacatgaagc ccagaaccag      660
aaaggacttc aacaactgca aaggtggtat gcagattgta ggttggacac cttaaacttt      720
ggaagagatg tagttattat tgctaattat ttggcttcat taattattgg tgatcatgcg      780
tttgactatg ttcgtctcgc atttgccaaa acatctgtgc ttgtaacaat tatggatgat      840
tttttcgact gtcatggctc tagtcaagag tgtgacaaga tcattgaatt agtaaaagaa      900
tggaaggaga atccggatgc agagtacgga tctgaggagc ttgagatcct ttttatggcg      960
ttgtacaata cagtaaatga gttggcggag agggctcgtg ttgaacaggg gcgtagtgtc     1020
aaagagtttc tagtcaaact gtgggttgaa atactctcag ctttcaagat agaattagat     1080
acatggagca atggcacgca gcaaagcttc gatgaataca tttcttcgtc gtggttgtcg     1140
aacggttccc ggctgacagg tctcctgacg atgcaattcg tcggagtaaa attgtccgat     1200
gaaatgctta tgagtgaaga gtgcactgat ttggctaggc atgtctgtat ggtcggccgg     1260
ctgctcaacg acgtgtgcag ttctgagagg gagcgcgagg aaaatattgc aggaaaaagt     1320
tatagcattc tactagcaac tgagaaagat ggaagaaaag ttagtgaaga tgaagccatt     1380
gcagagatca tgaaatggt tgaatatcac tggagaaaag tgttgcagat tgtgtataaa     1440
aaagaaagca ttttgccaag aagatgcaaa gatgtatttt tggagatggc taagggtacg     1500
ttttatgctt atgggatcaa cgatgaattg acttctcctc agcaatccaa ggaagatatg     1560
aaatcctttg tcttttga                                                   1578
```

<210> SEQ ID NO 94
<211> LENGTH: 795
<212> TYPE: PRT
<213> ORGANISM: Salvia sclarea

<400> SEQUENCE: 94

```
Met Ser Leu Pro Leu Ser Thr Cys Asn Gly Ser His Phe Arg Arg Tyr
1               5                   10                  15

Arg Leu Ser Pro Ala Ser Ala Ser Met Glu Thr Gly Leu Gln Thr Ala
            20                  25                  30

Thr Ser Ala Lys Ile Ala Ser Met Pro Ala Cys Phe Glu Glu Thr Arg
        35                  40                  45

Gly Arg Ile Ala Lys Leu Phe His Lys Asp Glu Leu Ser Val Ser Thr
    50                  55                  60

Tyr Asp Thr Ala Trp Val Ala Met Val Pro Ser Pro Thr Ser Leu Glu
65                  70                  75                  80

Glu Pro Cys Phe Pro Asp Cys Leu Asn Trp Leu Leu Glu Asn Gln Cys
                85                  90                  95

His Asp Gly Ser Trp Ala Arg Pro His His Ser Leu Leu Met Lys
            100                 105                 110

Asp Val Leu Ser Ser Thr Leu Ala Cys Ile Leu Ala Leu Lys Lys Trp
        115                 120                 125

Gly Val Gly Glu Lys Gln Ile Asn Arg Gly Leu His Phe Met Glu Leu
    130                 135                 140

Asn Phe Ala Ser Ala Thr Glu Lys Cys Gln Ile Thr Pro Met Gly Phe
145                 150                 155                 160

Asp Ile Val Phe Pro Ala Met Leu Asp Tyr Ala Arg Asp Phe Ser Leu
                165                 170                 175
```

```
Asp Met His Leu Glu Pro Thr Thr Leu Asn Asp Leu Ile His Lys Arg
            180                 185                 190

Asp Leu Glu Leu Lys Ser Lys Pro Asp Phe Ser Ser Asp Gly Glu Ala
        195                 200                 205

Tyr Trp Ala Tyr Ile Ala Glu Gly Met Gly Asn Leu Arg Asn Trp Glu
    210                 215                 220

Ser Val Met Lys Tyr Gln Arg Arg Asn Gly Ser Leu Phe Asn Cys Pro
225                 230                 235                 240

Ser Thr Thr Ala Ala Ala Phe Val Ala Leu Gly Asn Ser Asp Cys Leu
            245                 250                 255

Asn Tyr Leu His Ser Ala Leu Lys Lys Phe Gly Asn Ala Val Pro Ala
        260                 265                 270

Val Tyr Pro Leu Asp Ile Tyr Ser His Leu Cys Ile Val Asp Asn Leu
    275                 280                 285

Glu Arg Leu Gly Ile Ser Arg Tyr Phe Leu Thr Glu Ile Gln Ser Val
    290                 295                 300

Leu Asp Glu Thr His Arg Cys Trp Met Gln Gly Asn Glu Glu Ile Phe
305                 310                 315                 320

Met Asp Ala Ser Thr Cys Ala Leu Ala Phe Arg Ile Leu Arg Leu Asn
            325                 330                 335

Gly Tyr Asp Val Thr Ser Asp Pro Val Thr Lys Ile Gln His Glu Cys
        340                 345                 350

Phe Ser Ser Ser Phe His Gly Asn Val Met Asp Ile Asn Thr Thr Leu
        355                 360                 365

Glu Leu Tyr Arg Ala Ser Glu Leu Ile Leu Tyr Pro Asp Glu Arg Asp
    370                 375                 380

Leu Val Arg Gln Asn Leu Arg Leu Lys Gln Ile Leu Glu Gln Glu Leu
385                 390                 395                 400

Ser Asn Gly Phe Ile Gln Ser Cys Gln Leu Gly Arg Ser Val Asn Ala
            405                 410                 415

Glu Val Asn Gln Ala Ile Glu Tyr Pro Phe Tyr Ala Ile Met Asp Arg
        420                 425                 430

Val Ala Lys Arg Lys Asn Ile Glu Asn Tyr Asn Phe Asp Asn Thr Arg
    435                 440                 445

Ile Leu Lys Thr Ser Tyr Cys Ser Pro Asn Phe Gly Asn Lys Asp Phe
    450                 455                 460

Leu Phe Leu Ser Val Glu Asp Phe Asn Leu Cys Gln Ala Thr His Arg
465                 470                 475                 480

Glu Glu Leu Arg Glu Leu Glu Arg Trp Val Val Glu Asn Arg Leu Asp
            485                 490                 495

Glu Leu Gln Phe Ala Arg Ser Lys Ser Ala Tyr Cys Tyr Phe Ser Ala
        500                 505                 510

Ala Ala Thr Phe Ser Ala Pro Glu Leu Arg Asp Ala Arg Met Ser Trp
    515                 520                 525

Ala Lys Gly Gly Val Leu Thr Thr Val Ile Asp Asp Phe Phe Asp Val
    530                 535                 540

Gly Gly Ser Met Glu Glu Leu Lys Asn Leu Ile His Leu Val Glu Lys
545                 550                 555                 560

Trp Asp Val Asp Val Ser Thr Glu Cys Ser Ser His Asn Val Gln Ile
            565                 570                 575

Ile Phe Ser Ala Leu Lys Ser Thr Ile Arg Glu Ile Gly Tyr Lys Gly
        580                 585                 590

Leu Lys Leu Gln Gly Arg Cys Ile Thr Asn His Ile Ile Gly Ile Trp
```

```
                595                 600                 605
Leu Asp Leu Leu Asn Ser Met Met Lys Glu Thr Glu Trp Ala Arg Asp
610                 615                 620

Asn Tyr Val Pro Thr Ile Asp Glu Tyr Met Ser Asn Ala Tyr Val Ser
625                 630                 635                 640

Phe Ala Leu Gly Pro Ile Val Leu Pro Thr Leu Tyr Leu Val Gly Pro
                645                 650                 655

Lys Leu Ser Glu Glu Met Ala Asn His Pro Glu Tyr Tyr Lys Leu Phe
                660                 665                 670

Lys Leu Met Ser Thr Cys Gly Arg Leu Leu Asn Asp Ile Arg Gly Tyr
                675                 680                 685

Glu Arg Glu Leu Lys Asp Gly Lys Leu Asn Ala Leu Ser Leu Tyr Met
690                 695                 700

Ala Asn His Gly Gly Glu Val Ser Lys Glu Ala Ala Ile Ser Glu Ile
705                 710                 715                 720

Lys Ser Trp Ile Glu Ser Ser Arg Arg Glu Leu Leu Arg Leu Val Leu
                725                 730                 735

Glu Gly Lys Lys Ser Val Leu Pro Lys Pro Cys Lys Glu Leu Phe Trp
                740                 745                 750

His Met Cys Ser Val Val His Leu Phe Tyr Ser Lys Asp Asp Gly Phe
                755                 760                 765

Thr Ser Gln Asp Leu Ile Gln Val Val Asn Ala Ile Ile His Lys Pro
770                 775                 780

Ile Val Leu Lys Glu Gln Thr Gly Ala Arg Ile
785                 790                 795

<210> SEQ ID NO 95
<211> LENGTH: 771
<212> TYPE: PRT
<213> ORGANISM: Salvia sclarea

<400> SEQUENCE: 95

Met Glu Thr Gly Leu Gln Thr Ala Thr Ser Ala Lys Ile Ala Ser Met
1               5                   10                  15

Pro Ala Cys Phe Glu Gly Thr Arg Gly Arg Ile Ala Lys Leu Phe His
                20                  25                  30

Lys Asp Glu Leu Ser Val Ser Thr Tyr Asp Thr Ala Trp Val Ala Met
                35                  40                  45

Val Pro Ser Pro Thr Ser Leu Glu Glu Pro Cys Phe Pro Asp Cys Leu
50                  55                  60

Asn Trp Leu Leu Glu Asn Gln Cys His Asp Gly Ser Trp Ala Arg Pro
65                  70                  75                  80

His His His Ser Leu Leu Met Lys Asp Val Leu Ser Ser Thr Leu Ala
                85                  90                  95

Cys Ile Leu Ala Leu Lys Lys Trp Gly Val Gly Glu Lys Gln Ile Asn
                100                 105                 110

Arg Gly Leu His Phe Met Glu Leu Asn Phe Ala Ser Ala Thr Glu Lys
                115                 120                 125

Cys Gln Ile Thr Pro Met Gly Phe Asp Ile Val Phe Pro Ala Met Leu
                130                 135                 140

Asp Tyr Ala Arg Asp Phe Ser Leu Asp Met His Leu Glu Pro Thr Thr
145                 150                 155                 160

Leu Asn Asp Leu Ile His Lys Arg Asp Leu Glu Leu Lys Ser Lys Pro
                165                 170                 175
```

```
Asp Phe Ser Ser Asp Gly Glu Ala Tyr Trp Ala Tyr Ile Ala Glu Gly
            180                 185                 190

Met Gly Asn Leu Arg Asn Trp Glu Ser Val Met Lys Tyr Gln Arg Arg
        195                 200                 205

Asn Gly Ser Leu Phe Asn Cys Pro Ser Thr Ala Ala Ala Phe Val
    210                 215                 220

Ala Leu Gly Asn Ser Asp Cys Leu Asn Tyr Leu His Ser Ala Leu Lys
225                 230                 235                 240

Lys Phe Gly Asn Ala Val Pro Ala Val Tyr Pro Leu Asp Ile Tyr Ser
                245                 250                 255

His Leu Cys Ile Val Asp Asn Leu Glu Arg Leu Gly Ile Ser Arg Tyr
            260                 265                 270

Phe Leu Thr Glu Ile Gln Ser Val Leu Asp Glu Thr His Arg Cys Trp
        275                 280                 285

Met Gln Gly Asn Glu Glu Ile Phe Met Asp Ala Ser Thr Cys Ala Leu
    290                 295                 300

Ala Phe Arg Ile Leu Arg Leu Asn Gly Tyr Asp Val Thr Ser Asp Pro
305                 310                 315                 320

Val Thr Lys Ile Gln His Glu Cys Phe Ser Ser Phe His Gly Asn
                325                 330                 335

Val Met Asp Ile Asn Thr Thr Leu Glu Leu Tyr Arg Ala Ser Glu Leu
            340                 345                 350

Ile Leu Tyr Pro Asp Glu Arg Asp Leu Val Arg Gln Asn Leu Arg Leu
        355                 360                 365

Lys Gln Ile Leu Glu Gln Glu Leu Ser Asn Gly Phe Ile Gln Ser Cys
    370                 375                 380

Gln Leu Gly Arg Ser Val Asn Ala Glu Val Asn Gln Ala Ile Glu Tyr
385                 390                 395                 400

Pro Phe Tyr Ala Ile Met Asp Arg Val Ala Lys Arg Lys Asn Ile Glu
                405                 410                 415

Asn Tyr Asn Phe Asp Asn Thr Arg Ile Leu Lys Thr Ser Tyr Cys Ser
            420                 425                 430

Pro Asn Phe Gly Asn Lys Asp Phe Leu Phe Leu Ser Val Glu Asp Phe
        435                 440                 445

Asn Leu Cys Gln Ala Thr His Arg Glu Glu Leu Arg Glu Leu Glu Arg
    450                 455                 460

Trp Val Val Glu Asn Arg Leu Asp Glu Leu Gln Phe Ala Arg Ser Lys
465                 470                 475                 480

Ser Ala Tyr Cys Tyr Phe Ser Ala Ala Ala Thr Phe Ser Ala Pro Glu
                485                 490                 495

Leu Arg Asp Ala Arg Met Ser Trp Ala Lys Gly Gly Val Leu Thr Thr
            500                 505                 510

Val Ile Asp Asp Phe Phe Asp Val Gly Gly Ser Met Glu Glu Leu Lys
        515                 520                 525

Asn Leu Ile His Leu Val Glu Lys Trp Asp Val Asp Val Ser Thr Glu
    530                 535                 540

Cys Ser Ser His Asn Val Gln Ile Ile Phe Ser Ala Leu Lys Ser Thr
545                 550                 555                 560

Ile Arg Glu Ile Gly Tyr Lys Gly Leu Lys Leu Gln Gly Arg Cys Ile
                565                 570                 575

Thr Asn His Ile Ile Gly Ile Trp Leu Asp Leu Leu Asn Ser Met Met
            580                 585                 590

Lys Glu Thr Glu Trp Ala Arg Asp Asn Tyr Val Pro Thr Ile Asp Glu
```

```
            595                 600                 605
Tyr Met Ser Asn Ala Tyr Val Ser Phe Ala Leu Gly Pro Ile Val Leu
    610                 615                 620

Pro Thr Leu Tyr Leu Val Gly Pro Lys Leu Ser Glu Glu Met Ala Asn
625                 630                 635                 640

His Pro Glu Tyr Tyr Lys Leu Phe Lys Leu Met Ser Thr Cys Gly Arg
                645                 650                 655

Leu Leu Asn Asp Ile Arg Gly Tyr Glu Arg Glu Leu Lys Asp Gly Lys
            660                 665                 670

Leu Asn Ala Leu Ser Leu Tyr Met Ala Asn His Gly Gly Glu Val Ser
        675                 680                 685

Lys Glu Ala Ala Ile Ser Glu Ile Lys Ser Trp Ile Glu Ser Ser Arg
    690                 695                 700

Arg Glu Leu Leu Arg Leu Val Leu Glu Gly Lys Lys Ser Val Leu Pro
705                 710                 715                 720

Lys Pro Cys Lys Glu Leu Phe Trp His Met Cys Ser Val Val His Leu
                725                 730                 735

Phe Tyr Ser Lys Asp Asp Gly Phe Thr Ser Gln Asp Leu Ile Gln Val
            740                 745                 750

Val Asn Ala Ile Ile His Lys Pro Ile Val Leu Lys Glu Gln Thr Gly
        755                 760                 765

Ala Arg Ile
    770

<210> SEQ ID NO 96
<211> LENGTH: 525
<212> TYPE: PRT
<213> ORGANISM: Salvia sclarea

<400> SEQUENCE: 96

Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
            20                  25                  30

Ile Asp Thr Leu Gln Arg Leu Gly Val Asp Gln Phe Phe Gln Tyr Glu
        35                  40                  45

Ile Asn Thr Ile Leu Asp Asn Thr Phe Arg Leu Trp Gln Glu Lys His
    50                  55                  60

Lys Val Ile Tyr Gly Asn Val Thr Thr His Ala Met Ala Phe Arg Leu
65                  70                  75                  80

Leu Arg Val Lys Gly Tyr Glu Val Ser Ser Glu Glu Leu Ala Pro Tyr
                85                  90                  95

Gly Asn Gln Glu Ala Val Ser Gln Gln Thr Asn Asp Leu Pro Met Ile
            100                 105                 110

Ile Glu Leu Tyr Arg Ala Ala Asn Glu Arg Ile Tyr Glu Glu Glu Arg
        115                 120                 125

Ser Leu Glu Lys Ile Leu Ala Trp Thr Thr Ile Phe Leu Asn Lys Gln
    130                 135                 140

Val Gln Asp Asn Ser Ile Pro Asp Lys Lys Leu His Lys Leu Val Glu
145                 150                 155                 160

Phe Tyr Leu Arg Asn Tyr Lys Gly Ile Thr Ile Arg Leu Gly Ala Arg
                165                 170                 175

Arg Asn Leu Glu Leu Tyr Asp Met Thr Tyr Tyr Gln Ala Leu Lys Ser
            180                 185                 190
```

-continued

```
Thr Asn Arg Phe Ser Asn Leu Cys Asn Glu Asp Phe Leu Val Phe Ala
            195                 200                 205

Lys Gln Asp Phe Asp Ile His Glu Ala Gln Asn Gln Lys Gly Leu Gln
210                 215                 220

Gln Leu Gln Arg Trp Tyr Ala Asp Cys Arg Leu Asp Thr Leu Asn Phe
225                 230                 235                 240

Gly Arg Asp Val Val Ile Ala Asn Tyr Leu Ala Ser Leu Ile Ile
                245                 250                 255

Gly Asp His Ala Phe Asp Tyr Val Arg Leu Ala Phe Ala Lys Thr Ser
            260                 265                 270

Val Leu Val Thr Ile Met Asp Asp Phe Phe Asp Cys His Gly Ser Ser
            275                 280                 285

Gln Glu Cys Asp Lys Ile Ile Glu Leu Val Lys Glu Trp Lys Glu Asn
            290                 295                 300

Pro Asp Ala Glu Tyr Gly Ser Glu Glu Leu Glu Ile Leu Phe Met Ala
305                 310                 315                 320

Leu Tyr Asn Thr Val Asn Glu Leu Ala Glu Arg Ala Arg Val Glu Gln
                325                 330                 335

Gly Arg Ser Val Lys Glu Phe Leu Val Lys Leu Trp Val Glu Ile Leu
            340                 345                 350

Ser Ala Phe Lys Ile Glu Leu Asp Thr Trp Ser Asn Gly Thr Gln Gln
            355                 360                 365

Ser Phe Asp Glu Tyr Ile Ser Ser Trp Leu Ser Asn Gly Ser Arg
            370                 375                 380

Leu Thr Gly Leu Leu Thr Met Gln Phe Val Gly Val Lys Leu Ser Asp
385                 390                 395                 400

Glu Met Leu Met Ser Glu Glu Cys Thr Asp Leu Ala Arg His Val Cys
                405                 410                 415

Met Val Gly Arg Leu Leu Asn Asp Val Cys Ser Ser Glu Arg Glu Arg
            420                 425                 430

Glu Glu Asn Ile Ala Gly Lys Ser Tyr Ser Ile Leu Leu Ala Thr Glu
            435                 440                 445

Lys Asp Gly Arg Lys Val Ser Glu Asp Glu Ala Ile Ala Glu Ile Asn
450                 455                 460

Glu Met Val Glu Tyr His Trp Arg Lys Val Leu Gln Ile Val Tyr Lys
465                 470                 475                 480

Lys Glu Ser Ile Leu Pro Arg Arg Cys Lys Asp Val Phe Leu Glu Met
                485                 490                 495

Ala Lys Gly Thr Phe Tyr Ala Tyr Gly Ile Asn Asp Gly Leu Thr Ser
            500                 505                 510

Pro Gln Gln Ser Lys Glu Asp Met Lys Ser Phe Val Phe
            515                 520                 525

<210> SEQ ID NO 97
<211> LENGTH: 805
<212> TYPE: PRT
<213> ORGANISM: Salvia sclarea

<400> SEQUENCE: 97

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
                20                  25                  30

Ile Thr Arg Arg Arg Leu Gln Leu Gln Pro Glu Phe His Ala Glu Cys
            35                  40                  45
```

```
Ser Trp Leu Lys Ser Ser Lys His Ala Pro Leu Thr Leu Ser Cys
 50                  55                  60

Gln Ile Arg Pro Lys Gln Leu Ser Gln Ile Ala Glu Leu Arg Val Thr
 65                  70                  75                  80

Ser Leu Asp Ala Ser Gln Ala Ser Glu Lys Asp Ile Ser Leu Val Gln
                 85                  90                  95

Thr Pro His Lys Val Glu Val Asn Glu Lys Ile Glu Glu Ser Ile Glu
                100                 105                 110

Tyr Val Gln Asn Leu Leu Met Thr Ser Gly Asp Gly Arg Ile Ser Val
                115                 120                 125

Ser Pro Tyr Asp Thr Ala Val Ile Ala Leu Ile Lys Asp Leu Lys Gly
130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
                180                 185                 190

Leu His Ser Asp Ile Ile Glu Lys Gly Val Thr Tyr Ile Lys Glu Asn
    195                 200                 205

Val His Lys Leu Lys Gly Ala Asn Val Glu His Arg Thr Ala Gly Phe
210                 215                 220

Glu Leu Val Val Pro Thr Phe Met Gln Met Ala Thr Asp Leu Gly Ile
225                 230                 235                 240

Gln Asp Leu Pro Tyr Asp His Pro Leu Ile Lys Glu Ile Ala Asp Thr
                245                 250                 255

Lys Gln Gln Arg Leu Lys Glu Ile Pro Lys Asp Leu Val Tyr Gln Met
                260                 265                 270

Pro Thr Asn Leu Leu Tyr Ser Leu Glu Gly Leu Gly Asp Leu Glu Trp
                275                 280                 285

Glu Arg Leu Leu Lys Leu Gln Ser Gly Asn Gly Ser Phe Leu Thr Ser
290                 295                 300

Pro Ser Ser Thr Ala Ala Val Leu Met His Thr Lys Asp Glu Lys Cys
305                 310                 315                 320

Leu Lys Tyr Ile Glu Asn Ala Leu Lys Asn Cys Asp Gly Gly Ala Pro
                325                 330                 335

His Thr Tyr Pro Val Asp Ile Phe Ser Arg Leu Trp Ala Ile Asp Arg
                340                 345                 350

Leu Gln Arg Leu Gly Ile Ser Arg Phe Phe Gln His Glu Ile Lys Tyr
                355                 360                 365

Phe Leu Asp His Ile Glu Ser Val Trp Glu Glu Thr Gly Val Phe Ser
370                 375                 380

Gly Arg Tyr Thr Lys Phe Ser Asp Ile Asp Asp Thr Ser Met Gly Val
385                 390                 395                 400

Arg Leu Leu Lys Met His Gly Tyr Asp Val Asp Pro Asn Val Leu Lys
                405                 410                 415

His Phe Lys Gln Gln Asp Gly Lys Phe Ser Cys Tyr Ile Gly Gln Ser
                420                 425                 430

Val Glu Ser Ala Ser Pro Met Tyr Asn Leu Tyr Arg Ala Ala Gln Leu
                435                 440                 445

Arg Phe Pro Gly Glu Glu Val Leu Glu Glu Ala Thr Lys Phe Ala Phe
450                 455                 460
```

Asn Phe Leu Gln Glu Met Leu Val Lys Asp Arg Leu Gln Glu Arg Trp
465                 470                 475                 480

Val Ile Ser Asp His Leu Phe Asp Glu Ile Lys Leu Gly Leu Lys Met
            485                 490                 495

Pro Trp Tyr Ala Thr Leu Pro Arg Val Glu Ala Ala Tyr Tyr Leu Asp
        500                 505                 510

His Tyr Ala Gly Ser Gly Asp Val Trp Ile Gly Lys Ser Phe Tyr Arg
    515                 520                 525

Met Pro Glu Ile Ser Asn Asp Thr Tyr Lys Glu Leu Ala Ile Leu Asp
530                 535                 540

Phe Asn Arg Cys Gln Thr Gln His Gln Leu Glu Trp Ile His Met Gln
545                 550                 555                 560

Glu Trp Tyr Asp Arg Cys Ser Leu Ser Glu Phe Gly Ile Ser Lys Arg
            565                 570                 575

Glu Leu Leu Arg Ser Tyr Phe Leu Ala Ala Thr Ile Phe Glu Pro
        580                 585                 590

Glu Arg Thr Gln Glu Arg Leu Leu Trp Ala Lys Thr Arg Ile Leu Ser
    595                 600                 605

Lys Met Ile Thr Ser Phe Val Asn Ile Ser Gly Thr Thr Leu Ser Leu
610                 615                 620

Asp Tyr Asn Phe Asn Gly Leu Asp Glu Ile Ile Ser Ser Ala Asn Glu
625                 630                 635                 640

Asp Gln Gly Leu Ala Gly Thr Leu Leu Ala Thr Phe His Gln Leu Leu
            645                 650                 655

Asp Gly Phe Asp Ile Tyr Thr Leu His Gln Leu Lys His Val Trp Ser
        660                 665                 670

Gln Trp Phe Met Lys Val Gln Gln Gly Glu Gly Ser Gly Gly Glu Asp
    675                 680                 685

Ala Val Leu Leu Ala Asn Thr Leu Asn Ile Cys Ala Gly Leu Asn Glu
690                 695                 700

Asp Val Leu Ser Asn Asn Glu Tyr Thr Ala Leu Ser Thr Leu Thr Asn
705                 710                 715                 720

Lys Ile Cys Asn Arg Leu Ala Gln Ile Gln Asp Asn Lys Ile Leu Gln
            725                 730                 735

Val Val Asp Gly Ser Ile Lys Asp Lys Glu Leu Glu Gln Asp Met Gln
        740                 745                 750

Ala Leu Val Lys Leu Val Leu Gln Glu Asn Gly Gly Ala Val Asp Arg
    755                 760                 765

Asn Ile Arg His Thr Phe Leu Ser Val Ser Lys Thr Phe Tyr Tyr Asp
770                 775                 780

Ala Tyr His Asp Asp Glu Thr Thr Asp Leu His Ile Phe Lys Val Leu
785                 790                 795                 800

Phe Arg Pro Val Val
            805

<210> SEQ ID NO 98
<211> LENGTH: 804
<212> TYPE: PRT
<213> ORGANISM: Salvia sclarea

<400> SEQUENCE: 98

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
            20                  25                  30

```
Ile Ile Arg Arg Arg Leu Gln Leu Gln Pro Glu Phe His Ala Glu Cys
         35                  40                  45

Ser Trp Leu Lys Ser Ser Lys His Ala Pro Phe Thr Leu Ser Cys
     50                  55                  60

Gln Ile Arg Pro Lys Gln Leu Ser Gln Ile Ala Glu Leu Arg Val Thr
 65                  70                  75                  80

Ser Leu Asp Ala Ser Gln Ala Ser Glu Lys Asp Ile Ser Leu Val Gln
                 85                  90                  95

Thr Pro His Lys Val Glu Val Asn Glu Lys Ile Glu Glu Ser Ile Glu
                100                 105                 110

Tyr Val Gln Asn Leu Leu Met Thr Ser Gly Asp Gly Arg Ile Ser Val
             115                 120                 125

Ser Pro Tyr Asp Thr Ala Val Ile Ala Leu Ile Lys Asp Leu Lys Gly
         130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
                180                 185                 190

Leu Gln Ser Asp Ile Ile Glu Lys Gly Val Thr Tyr Ile Lys Glu Asn
             195                 200                 205

Val His Lys Leu Lys Gly Ala Asn Val Glu His Arg Thr Ala Gly Phe
         210                 215                 220

Glu Leu Val Val Pro Thr Phe Met Gln Met Ala Thr Asp Leu Gly Ile
225                 230                 235                 240

Gln Gly Leu Pro Tyr Asp His Pro Leu Ile Lys Glu Ile Ala Asp Thr
                245                 250                 255

Lys Gln Gln Arg Leu Lys Glu Ile Pro Lys Asp Leu Val Tyr Gln Met
                260                 265                 270

Pro Thr Asn Leu Leu Tyr Ser Leu Glu Gly Leu Gly Asp Leu Glu Trp
             275                 280                 285

Glu Arg Leu Leu Lys Leu Gln Ser Gly Asn Gly Ser Phe Leu Thr Ser
         290                 295                 300

Pro Ser Ser Thr Ala Ala Val Leu Met His Thr Lys Asp Glu Lys Cys
305                 310                 315                 320

Leu Lys Tyr Ile Glu Asn Ala Leu Lys Asn Cys Asp Gly Gly Ala Pro
                325                 330                 335

His Thr Tyr Pro Val Asp Ile Phe Ser Arg Leu Trp Ala Ile Asp Arg
                340                 345                 350

Leu Gln Arg Leu Gly Ile Ser Arg Phe Phe Gln His Glu Ile Lys Tyr
             355                 360                 365

Phe Leu Asp His Ile Glu Ser Val Trp Glu Glu Thr Gly Val Phe Ser
         370                 375                 380

Gly Arg Tyr Thr Lys Phe Ser Asp Ile Asp Asp Thr Ser Met Gly Val
385                 390                 395                 400

Arg Leu Leu Lys Met His Gly Tyr Asp Val Asp Pro Asn Val Leu Lys
                405                 410                 415

His Phe Lys Gln Gln Asp Gly Lys Phe Ser Cys Tyr Ile Gly Gln Ser
                420                 425                 430

Val Glu Ser Ala Ser Pro Met Tyr Asn Leu Tyr Arg Ala Ala Gln Leu
             435                 440                 445
```

```
Arg Phe Pro Gly Glu Glu Val Leu Glu Glu Ala Thr Lys Phe Ala Phe
    450                 455                 460

Asn Phe Leu Gln Glu Met Leu Val Lys Asp Arg Leu Gln Glu Arg Trp
465                 470                 475                 480

Val Ile Ser Asp His Leu Phe Asp Glu Ile Lys Leu Gly Leu Lys Met
                485                 490                 495

Pro Trp Tyr Ala Thr Leu Pro Arg Val Glu Ala Ala Tyr Tyr Leu Asp
            500                 505                 510

His Tyr Ala Gly Ser Gly Asp Val Trp Ile Gly Lys Ser Phe Tyr Arg
        515                 520                 525

Met Pro Glu Ile Ser Asn Asp Thr Tyr Lys Glu Leu Ala Ile Leu Asp
    530                 535                 540

Phe Asn Arg Cys Gln Thr Gln His Gln Leu Glu Trp Ile Gln Met Gln
545                 550                 555                 560

Glu Trp Tyr Asp Arg Cys Ser Leu Ser Glu Phe Gly Ile Ser Lys Arg
                565                 570                 575

Glu Leu Leu Arg Ser Tyr Phe Leu Ala Ala Ala Thr Ile Phe Glu Pro
            580                 585                 590

Glu Arg Thr Gln Glu Arg Leu Leu Trp Ala Lys Thr Arg Ile Leu Ser
        595                 600                 605

Lys Met Ile Thr Ser Phe Val Asn Ile Ser Gly Thr Thr Leu Ser Leu
    610                 615                 620

Asp Tyr Asn Phe Asn Gly Leu Asp Glu Ile Ile Ser Ala Asn Glu Asp
625                 630                 635                 640

Gln Gly Leu Ala Gly Thr Leu Ala Thr Phe His Gln Leu Leu Asp
                645                 650                 655

Gly Phe Asp Ile Tyr Thr Leu His Gln Leu Lys His Val Trp Ser Gln
            660                 665                 670

Trp Phe Met Lys Val Gln Gln Gly Glu Gly Ser Gly Gly Glu Asp Ala
        675                 680                 685

Val Leu Leu Ala Asn Thr Leu Asn Ile Cys Ala Gly Leu Asn Glu Asp
    690                 695                 700

Val Leu Ser Asn Asn Glu Tyr Thr Ala Leu Ser Thr Leu Thr Asn Lys
705                 710                 715                 720

Ile Cys Asn Arg Leu Ala Gln Ile Gln Asp Asn Lys Ile Leu Gln Val
                725                 730                 735

Val Asp Gly Ser Ile Lys Asp Lys Glu Leu Glu Gln Asp Met Gln Ala
            740                 745                 750

Leu Val Lys Leu Val Leu Gln Glu Asn Gly Gly Ala Val Asp Arg Asn
        755                 760                 765

Ile Arg His Thr Phe Leu Ser Val Ser Lys Thr Phe Tyr Tyr Asp Ala
    770                 775                 780

Tyr His Asp Asp Glu Thr Thr Asp Leu His Ile Phe Lys Val Leu Phe
785                 790                 795                 800

Arg Pro Val Val

<210> SEQ ID NO 99
<211> LENGTH: 816
<212> TYPE: PRT
<213> ORGANISM: Oryza sativa

<400> SEQUENCE: 99

Met Met Leu Leu Ser Ser Ser Tyr Ser Gly Gly Gln Phe Pro Gly Val
1               5                   10                  15
```

```
Ser Pro Leu Gly Thr Arg Pro Lys Arg Ser Thr Val Val Pro Leu
         20                  25                  30

Pro Val Val Thr Arg Ala Thr Ala Gly Gly Val Arg Asn Asn Leu Glu
             35                  40                  45

Val Val Gly Asn Ala Gly Thr Leu Gln Gly Met Asp Ile Asp Glu Leu
         50                  55                  60

Arg Val Ile Val Arg Lys Gln Leu Gln Gly Val Glu Leu Ser Pro Ser
65                  70                  75                  80

Ser Tyr Asp Thr Ala Trp Val Ala Met Val Pro Val Gln Gly Ser Pro
                 85                  90                  95

Gln Ser Pro Cys Phe Pro Gln Cys Val Glu Trp Ile Leu Gln Asn Gln
             100                 105                 110

Gln Glu Asp Gly Ser Trp Gly His Ser Ala Gly Pro Ser Gly Glu Val
         115                 120                 125

Asn Lys Asp Ile Leu Leu Ser Thr Leu Ala Cys Val Leu Ala Leu Asn
     130                 135                 140

Thr Trp Asn Val Gly Gln Asp His Ile Arg Arg Gly Leu Ser Phe Ile
145                 150                 155                 160

Gly Arg Asn Phe Ser Val Ala Ile Asp Gly Gln Cys Ala Ala Pro Val
                 165                 170                 175

Gly Phe Asn Ile Thr Phe Ser Gly Met Leu His Leu Ala Ile Gly Met
             180                 185                 190

Gly Leu Lys Phe Pro Val Met Glu Thr Asp Ile Asp Ser Ile Phe Arg
         195                 200                 205

Leu Arg Glu Val Glu Phe Glu Arg Asp Ala Gly Gly Thr Ala Ser Ala
210                 215                 220

Arg Lys Ala Phe Met Ala Tyr Val Ser Glu Gly Leu Gly Arg Glu Gln
225                 230                 235                 240

Asp Trp Asp His Val Met Ala Tyr Gln Arg Lys Asn Gly Ser Leu Phe
                 245                 250                 255

Asn Ser Pro Ser Thr Thr Ala Ala Ser Ala Ile His Ser Cys Asn Asp
             260                 265                 270

Arg Ala Leu Asp Tyr Leu Val Ser Leu Thr Ser Lys Leu Gly Gly Pro
         275                 280                 285

Val Pro Ala Ile His Pro Asp Lys Val Tyr Ser Gln Leu Cys Met Val
     290                 295                 300

Asp Thr Leu Glu Lys Met Gly Ile Ser Ser Asp Phe Ala Cys Asp Ile
305                 310                 315                 320

Arg Asp Ile Leu Asp Met Thr Tyr Ser Cys Trp Met Gln Asp Glu Glu
                 325                 330                 335

Glu Ile Met Leu Asp Met Ala Thr Cys Ala Lys Ala Phe Arg Leu Leu
             340                 345                 350

Arg Met His Gly Tyr Asp Val Ser Ser Glu Gly Met Ala Arg Phe Ala
         355                 360                 365

Glu Arg Ser Ser Phe Asp Asp Ser Ile His Ala Tyr Leu Asn Asp Thr
     370                 375                 380

Lys Pro Leu Leu Glu Leu Tyr Lys Ser Ser Gln Leu His Phe Leu Glu
385                 390                 395                 400

Glu Asp Leu Ile Leu Glu Asn Ile Ser Ser Trp Ser Ala Lys Leu Leu
                 405                 410                 415

Lys Gln Gln Leu Ser Ser Asn Lys Ile Met Lys Ser Leu Met Pro Glu
             420                 425                 430

Val Glu Tyr Ala Leu Lys Tyr Pro Leu Tyr Ser Thr Val Asp Ala Leu
```

```
                435                 440                 445
Glu His Arg Gly Asn Ile Glu Arg Phe Asn Val Asn Gly Phe Gln Arg
450                 455                 460
Pro Lys Ser Gly Tyr Cys Gly Ser Gly Ala Asp Lys Glu Ile Leu Ala
465                 470                 475                 480
Leu Ala Val Asp Lys Phe His Tyr Asn Gln Ser Val Tyr Gln Gln Glu
                485                 490                 495
Leu Arg Tyr Leu Glu Ser Trp Val Ala Glu Phe Gly Leu Asp Glu Leu
            500                 505                 510
Lys Phe Ala Arg Val Ile Pro Leu Gln Ser Leu Leu Ser Ala Leu Val
        515                 520                 525
Pro Leu Phe Pro Ala Glu Leu Ser Asp Ala Arg Ile Ala Phe Ser Gln
530                 535                 540
Asn Cys Met Leu Thr Thr Met Val Asp Asp Phe Phe Asp Gly Gly Gly
545                 550                 555                 560
Ser Met Glu Glu Met Val Asn Phe Val Ala Leu Ile Asp Glu Trp Asp
                565                 570                 575
Asn His Gly Glu Ile Gly Phe Cys Ser Asn Asn Val Glu Ile Met Phe
            580                 585                 590
Asn Ala Ile Tyr Asn Thr Thr Lys Arg Asn Cys Ala Lys Ala Ala Leu
        595                 600                 605
Val Gln Asn Arg Cys Val Met Asp His Ile Ala Lys Gln Trp Gln Val
610                 615                 620
Met Val Arg Ala Met Lys Thr Glu Ala Glu Trp Ala Ala Ser Arg His
625                 630                 635                 640
Ile Pro Ala Thr Met Glu Glu Tyr Met Ser Val Gly Glu Pro Ser Phe
                645                 650                 655
Ala Leu Gly Pro Ile Val Pro Leu Ser Ala Tyr Leu Leu Gly Glu Glu
            660                 665                 670
Leu Pro Glu Glu Ala Val Arg Ser Pro Glu Tyr Gly Gln Leu Leu Arg
        675                 680                 685
His Ala Ser Ala Val Gly Arg Leu Leu Asn Asp Val Met Thr Tyr Glu
690                 695                 700
Lys Glu Val Leu Thr Trp Thr Pro Asn Ser Val Leu Leu Gln Ala Leu
705                 710                 715                 720
Ala Ala Ala Arg Gly Gly Gly Glu Ser Pro Thr Pro Ser Pro Ala
                725                 730                 735
Cys Ala Glu Ala Ala Arg Gly Glu Val Arg Arg Ala Ile Gln Ala Ser
            740                 745                 750
Trp Arg Asp Leu His Arg Leu Val Phe Arg Asp Asp Gly Ser Ser
        755                 760                 765
Ile Val Pro Arg Ala Cys Arg Glu Leu Phe Trp Gly Thr Ala Lys Val
770                 775                 780
Ala Asn Val Phe Tyr Gln Glu Val Asp Gly Tyr Thr Pro Lys Ala Met
785                 790                 795                 800
Arg Gly Met Ala Asn Ala Val Ile Leu Asp Pro Leu His Leu Gln Gln
                805                 810                 815

<210> SEQ ID NO 100

<400> SEQUENCE: 100

000
```

```
<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104
<211> LENGTH: 18
<212> TYPE: PRT
<213> ORGANISM: Salvia sclarea

<400> SEQUENCE: 104

Arg Leu Ala Phe Ala Lys Thr Ser Val Leu Val Thr Ile Met Asp Asp
1               5                  10                  15

Phe Phe

<210> SEQ ID NO 105

<400> SEQUENCE: 105

000

<210> SEQ ID NO 106
<211> LENGTH: 745
<212> TYPE: PRT
<213> ORGANISM: Cucumis sativus

<400> SEQUENCE: 106

Met Asn Leu Ser Arg Pro Thr Asn Leu Gly Cys Phe Thr Ala Ser Ser
1               5                  10                  15

Ser Ala Ser Leu Phe Pro Gly Leu Asp Val Gly Thr Lys Thr Lys Thr
                20                  25                  30

Gly Ala Leu Arg Phe Glu Glu Thr Lys Glu Arg Ile Lys Lys Leu Phe
            35                  40                  45

Lys Asn Val Glu Leu Ser Val Ser Thr Tyr Asp Thr Ala Trp Val Ala
        50                  55                  60

Met Val Pro Ser Pro Thr Ser Leu Asn Lys Pro Leu Phe Pro Glu Cys
65                  70                  75                  80

Ile Asn Trp Val Leu Asp His Gln Asn Pro Asp Gly Ser Trp Gly Ile
                85                  90                  95

Leu His Asp His Gln Leu Val Met Lys Ala Thr Leu Leu Ser Thr Leu
                100                 105                 110

Ala Cys Val Leu Thr Leu Lys Arg Trp Asp Ile Gly Asp Asp His Met
            115                 120                 125

Ser Lys Ala Leu Ser Phe Ile Lys Ser Asn Ile Ala Ser Ala Thr Asp
        130                 135                 140

Glu Asn Gln Arg Ser Pro Val Gly Phe Asp Ile Ile Phe Pro Gly Met
145                 150                 155                 160

Ile Glu Tyr Ala Lys Asp Leu Asn Leu Asn Leu Pro Leu Ala Ser Met
```

-continued

```
                165                 170                 175
Asn Val Asp Ala Leu Val Gln Lys Lys Glu Leu Glu Leu Arg Ser Cys
                180                 185                 190

Cys Ser Asn Ser Glu Gly Gly Lys Ala Tyr Leu Ala Tyr Val Ser Glu
                195                 200                 205

Gly Ile Gly Lys Leu Gln Asp Trp Glu Met Val Met Arg Tyr Gln Arg
                210                 215                 220

Lys Asn Gly Ser Leu Phe Ser Ser Pro Ser Thr Thr Ala Val Ala Phe
225                 230                 235                 240

Met His Arg Asn Asp Asp Gly Cys Phe Asn Tyr Leu Arg Ser Val Leu
                245                 250                 255

Gln Lys Phe His Ser Ser Val Pro Ala Ile Tyr Pro Leu Asp Ile Tyr
                260                 265                 270

Ala Arg Leu His Met Val Asp Ser Leu Gln Lys Leu Gly Ile Asp Gly
                275                 280                 285

His Phe Lys Asp Glu Ile Arg Ser Val Leu Asp Glu Thr Tyr Ser Cys
                290                 295                 300

Trp Met Gln Gly Glu Glu Asn Ile Phe Leu Asp Ala Ser Thr Cys Ala
305                 310                 315                 320

Met Ala Phe Arg Met Leu Arg Val Glu Gly Tyr Asp Val Ser Ser Asp
                325                 330                 335

Gln Leu Thr Gln Phe Ser Glu Gly Leu Phe Ser Asn Cys Leu Gly Gly
                340                 345                 350

His Leu Lys Asp Phe Ser Ala Ser Leu Glu Leu Phe Lys Ala Ser Gln
                355                 360                 365

Ile Ile Ile Tyr Pro Asp Glu Phe Ile Leu Glu Asn Ile Asn Ser Trp
                370                 375                 380

Thr Ser Arg Phe Leu Asn His Gly Leu Ser Ser Gly Ser Val His Ser
385                 390                 395                 400

Asp Arg Thr Glu Arg Leu Val Lys Gln Glu Ala Val Asn Ala Phe Glu
                405                 410                 415

Phe Pro Tyr Asn Ser Thr Leu Glu Arg Leu Ser Asn Lys Arg Ala Leu
                420                 425                 430

Glu Ser Tyr Ser Gly Asp Ile Val Arg Ile Ser Lys Thr Ala Tyr Ala
                435                 440                 445

Cys Leu Asn Phe Gly His Gln Asp Phe Leu Glu Leu Ala Val Glu Asp
                450                 455                 460

Phe Asn Thr Leu Gln Gly Ile His Arg Lys Glu Leu Lys Glu Leu Glu
465                 470                 475                 480

Lys Trp Val Ile Glu Asn Lys Leu Asp Lys Leu Lys Phe Ala Arg Gln
                485                 490                 495

Lys Leu Ala Tyr Cys Tyr Phe Ser Ala Ala Ala Thr Leu Thr Ser Pro
                500                 505                 510

Glu Leu Cys Asp Ala Arg Leu Ser Trp Ala Lys Asn Gly Val Leu Thr
                515                 520                 525

Thr Val Val Asp Asp Phe Phe Asp Val Gly Gly Ser Glu Glu Glu Leu
530                 535                 540

Val Asn Leu Ile Gln Leu Val Glu Lys Trp Asp Ala Ser Gly Glu Thr
545                 550                 555                 560

Gly Tyr Cys Ser Lys Glu Val Glu Ile Ile Phe Leu Ala Leu His Ser
                565                 570                 575

Thr Ile Cys Glu Ile Gly Lys Lys Ala Leu Pro Trp Gln Gly Arg Ser
                580                 585                 590
```

```
Val Met Arg Asn Val Ile Asp Ile Trp Leu Ala Leu Leu Glu Ser Met
            595                 600                 605

Arg Lys Glu Ala Glu Trp Leu Lys Asn Lys Val Val Pro Ser Leu Asp
610                 615                 620

Glu Tyr Leu Met Ser Thr Ser Gly Arg Leu Leu Asn Asp Thr Arg Thr
625                 630                 635                 640

Phe Asp Arg Glu Ser Ser Glu Gly Lys Leu Asn Ala Leu Ser Leu Tyr
                645                 650                 655

Met Ile Ser Ala Gly Gly Lys Leu Thr Lys Glu Glu Ala Thr Glu Ala
                660                 665                 670

Met Lys Gly Asp Val Asp Arg Thr Arg Arg Glu Leu Leu Arg Leu Val
                675                 680                 685

Leu Gln Glu Asn Ser Thr Ile Pro Arg Ala Cys Lys Asp Leu Phe Trp
            690                 695                 700

Lys Met Ser Cys Val Val His Leu Phe Tyr Arg Lys Asp Asp Gly Phe
705                 710                 715                 720

Thr Ser His Glu Leu Met Asn Ser Ala Lys Ala Leu Phe Glu Gln Pro
                725                 730                 735

Met Val Leu Asp Glu Leu Leu Asn Lys
                740                 745

<210> SEQ ID NO 107
<211> LENGTH: 759
<212> TYPE: PRT
<213> ORGANISM: Nicotiana tabacum

<400> SEQUENCE: 107

Met Glu Glu Ala Lys Glu Arg Ile Arg Glu Thr Phe Gly Lys Ile Glu
1               5                   10                  15

Leu Ser Pro Ser Ser Tyr Asp Thr Ala Trp Val Ala Met Val Pro Ser
                20                  25                  30

Arg Tyr Ser Met Asn Gln Pro Cys Phe Pro Gln Cys Leu Asp Trp Ile
            35                  40                  45

Leu Glu Asn Gln Arg Glu Asp Gly Ser Trp Gly Leu Asn Pro Ser His
    50                  55                  60

Pro Leu Leu Val Lys Asp Ser Leu Ser Ser Thr Leu Ala Ser Leu Leu
65                  70                  75                  80

Ala Leu Arg Lys Trp Arg Ile Gly Asp Asn Gln Val Gln Arg Gly Leu
                85                  90                  95

Gly Phe Ile Glu Thr His Gly Trp Ala Val Asp Asn Lys Asp Gln Ile
            100                 105                 110

Ser Pro Leu Gly Phe Glu Ile Ile Phe Pro Cys Met Thr Asn Tyr Ala
        115                 120                 125

Glu Lys Leu Asn Leu Asp Leu Pro Leu Asp Pro Asn Leu Val Asn Met
    130                 135                 140

Met Leu Cys Glu Arg Glu Leu Thr Ile Glu Arg Ala Leu Lys Asn Glu
145                 150                 155                 160

Phe Glu Gly Asn Met Ala Asn Val Glu Tyr Phe Ala Glu Gly Leu Gly
                165                 170                 175

Glu Ser Cys His Trp Lys Glu Met Met Leu Arg Gln Arg His Asn Gly
            180                 185                 190

Ser Leu Phe Asp Ser Pro Ala Thr Thr Ala Ala Ala Leu Ile Tyr His
        195                 200                 205

Gln Tyr Asp Glu Lys Cys Phe Gly Tyr Leu Asn Ser Ile Leu Lys Leu
```

```
                210                 215                 220
His Asp Asn Trp Val His Thr Ile Cys Pro Thr Lys Ile His Ser Asn
225                 230                 235                 240

Leu Phe Leu Val Asp Ala Leu Gln Asn Leu Gly Val Asp Arg Tyr Phe
                245                 250                 255

Lys Thr Glu Val Lys Arg Val Leu Asp Glu Ile Tyr Arg Leu Trp Leu
                260                 265                 270

Glu Lys Asn Glu Glu Ile Phe Ser Asp Val Ala His Cys Ala Met Ala
            275                 280                 285

Phe Arg Leu Leu Arg Met Asn Asn Tyr Glu Val Ser Ser Glu Glu Leu
            290                 295                 300

Glu Gly Phe Val Asp Gln Glu His Phe Phe Thr Ser Ser Gly Lys
305                 310                 315                 320

Leu Met Asn His Val Ala Ile Leu Glu Leu His Arg Ala Ser Gln Val
                325                 330                 335

Ala Ile His Glu Arg Lys Asp His Ile Leu Asp Lys Ile Ser Thr Trp
                340                 345                 350

Thr Arg Asn Phe Met Glu Gln Lys Leu Leu Asp Lys His Ile Pro Asp
            355                 360                 365

Arg Ser Lys Lys Glu Met Glu Phe Ala Met Arg Lys Phe Tyr Gly Thr
            370                 375                 380

Phe Asp Arg Val Glu Thr Arg Arg Tyr Ile Glu Ser Tyr Lys Met Asp
385                 390                 395                 400

Ser Phe Lys Ile Leu Lys Ala Ala Tyr Arg Ser Ser Gly Ile Asn Asn
                405                 410                 415

Ile Asp Leu Leu Lys Phe Ser Glu His Asp Phe Asn Leu Cys Gln Thr
                420                 425                 430

Arg His Lys Glu Glu Leu Gln Gln Met Lys Arg Trp Phe Thr Asp Cys
            435                 440                 445

Lys Leu Glu Gln Val Gly Leu Ser Gln Gln Tyr Leu Tyr Thr Ser Tyr
            450                 455                 460

Phe Ile Ile Ala Ala Ile Leu Phe Glu Pro Glu Tyr Ala Asp Ala Arg
465                 470                 475                 480

Leu Ala Tyr Ala Lys Tyr Ala Ile Ile Ile Thr Ala Val Asp Asp Phe
                485                 490                 495

Phe Asp Cys Phe Ile Cys Lys Glu Glu Leu Gln Asn Ile Ile Glu Leu
                500                 505                 510

Val Glu Arg Trp Glu Gly Tyr Ser Thr Val Gly Phe Arg Ser Glu Arg
            515                 520                 525

Val Arg Ile Phe Phe Leu Ala Leu Tyr Lys Met Val Glu Glu Ile Ala
            530                 535                 540

Ala Lys Ala Glu Thr Lys Gln Gly Arg Cys Val Lys Asp His Leu Ile
545                 550                 555                 560

Asn Leu Trp Ile Asp Met Leu Lys Cys Met Leu Val Glu Leu Asp Leu
                565                 570                 575

Trp Lys Ile Lys Ser Thr Thr Pro Ser Ile Glu Glu Tyr Leu Ser Val
                580                 585                 590

Ala Cys Val Thr Ile Gly Val Pro Cys Phe Val Leu Thr Ser Leu Tyr
            595                 600                 605

Leu Leu Gly Pro Lys Leu Ser Lys Asp Val Ile Glu Ser Ser Glu Val
            610                 615                 620

Ser Ala Leu Cys Asn Cys Thr Ala Ala Val Ala Arg Leu Ile Asn Asp
625                 630                 635                 640
```

```
Ile His Ser Tyr Lys Arg Glu Gln Ala Glu Ser Ser Thr Asn Met Val
                645             650                 655

Ser Ile Leu Ile Thr Gln Ser Gln Gly Thr Ile Ser Glu Glu Glu Ala
            660                 665                 670

Ile Arg Gln Ile Lys Glu Met Met Glu Ser Lys Arg Arg Glu Leu Leu
        675                 680                 685

Gly Met Val Leu Gln Asn Lys Glu Ser Gln Leu Pro Gln Val Cys Lys
    690                 695                 700

Asp Leu Phe Trp Thr Thr Ile Asn Ala Ala Ala Tyr Ser Ile His Thr
705                 710                 715                 720

His Gly Arg Trp Val Ser Leu Pro Arg Gly Ile Gln Glu Pro Tyr Gln
                725                 730                 735

Arg Cys Asn Leu Gln Thr Thr Gln Ser Ile Phe Pro Ile Ile Cys Leu
            740                 745                 750

Lys Ser Phe Thr Ile Cys Tyr
            755

<210> SEQ ID NO 108
<211> LENGTH: 830
<212> TYPE: PRT
<213> ORGANISM: Oryza sativa

<400> SEQUENCE: 108

Met Met Leu Leu Gly Ser Pro Ser Ser Gly Tyr Gly Gly Lys Phe
1               5                   10                  15

Ala Gly Ala Ser Pro Ala Gly Gly Thr Thr Thr Met Ala Pro Ser Ala
            20                  25                  30

Lys Gln Pro Ser Ser Arg Ala Pro Pro Gly Ile Thr Gly Gly Arg
        35                  40                  45

Asn Asp Leu Arg Ile Leu Ser Pro Ala Ala Ala Ala Ala Val Gly
    50                  55                  60

Gly Leu Glu Met Lys Lys Pro Glu Ala Glu Gly Ile Ala Glu Ser Leu
65                  70                  75                  80

Gln Ala Thr His Arg Lys Glu Leu Glu Ala Ser Ile Arg Lys Gln Leu
                85                  90                  95

Gln Gly Val Glu Leu Ser Pro Ser Pro Tyr Asp Thr Ala Trp Val Ala
            100                 105                 110

Met Val Pro Leu Arg Gly Ser Ser His Asn Pro Ser Phe Pro Gln Cys
        115                 120                 125

Val Asp Trp Ile Leu Glu Asn Gln Trp Asp Asp Gly Ser Trp Ser Ile
    130                 135                 140

Asp Gly Ser Ile Ser Thr Ala Asn Lys Asp Val Leu Ser Ser Thr Leu
145                 150                 155                 160

Ala Cys Val Leu Ala Leu Asn Lys Trp Asn Val Gly Arg Glu His Ile
                165                 170                 175

Arg Arg Gly Leu Ser Phe Ile Gly Arg Asn Phe Ser Ile Ala Met Asp
            180                 185                 190

Asp Gln Ala Val Ala Pro Ile Gly Phe Gly Ile Thr Phe Pro Ala Met
        195                 200                 205

Leu Thr Leu Ala Asn Gly Ser Gly Leu Glu Val Pro Val Arg Gln Asn
    210                 215                 220

Asp Ile Asp Ser Leu Asn His Leu Arg Glu Met Lys Ile Gln Arg Glu
225                 230                 235                 240

Ala Gly Asn His Ser Arg Gly Arg Lys Ala Tyr Met Ala Tyr Leu Ala
```

-continued

```
                245                 250                 255
Glu Gly Phe Gly Asn Leu Leu Glu Trp Asp Glu Ile Met Met Phe Gln
            260                 265                 270

Arg Lys Asn Gly Ser Leu Phe Asn Cys Pro Ser Ser Thr Ala Gly Ala
        275                 280                 285

Leu Ala Asn Tyr His Asp Asp Lys Ala Leu Gln Tyr Leu Gln Ser Leu
    290                 295                 300

Val Asn Lys Phe Asp Gly Val Val Pro Thr Leu Tyr Pro Leu Asn Ile
305                 310                 315                 320

Tyr Cys Gln Leu Ser Met Val Asp Ala Leu Glu Asn Met Gly Ile Ser
                325                 330                 335

Gln Tyr Phe Ala Ser Glu Ile Lys Ser Ile Leu Asp Met Thr Tyr Ser
            340                 345                 350

Ser Trp Leu Gly Arg Asp Glu Glu Ile Met Leu Asp Val Thr Thr Cys
        355                 360                 365

Ala Met Ala Phe Arg Leu Leu Arg Met Asn Gly Tyr Asp Val Ser Ser
    370                 375                 380

Asp Glu Leu Ser His Val Ala Gly Ala Ser Gly Phe Arg Asp Ser Leu
385                 390                 395                 400

Gln Gly Tyr Leu Asn Asp Arg Lys Ser Val Leu Glu Val Tyr Lys Thr
                405                 410                 415

Ser Lys His Ser Ile Ser Glu Asn Asp Leu Ile Leu Asp Ser Ile Gly
            420                 425                 430

Ser Trp Ser Gly Ser Leu Leu Lys Glu Met Leu Cys Ser Asn Gly Ile
        435                 440                 445

Gln Gly Thr Pro Gly Arg Glu Glu Ile Glu Phe Ala Leu Lys Tyr Pro
    450                 455                 460

Phe Tyr Ser Thr Leu Glu Arg Leu Val His Arg Lys Asn Ile Val Leu
465                 470                 475                 480

Phe Asp Ala Lys Gly Ser Gln Met Leu Lys Thr Glu Cys Met Pro Val
                485                 490                 495

His Asp Ser Gln Asp Phe Leu Ala Leu Ala Val Asp Asp Phe Cys Ile
            500                 505                 510

Ser Gln Ser Asn Tyr Gln Asn Glu Leu Asn Tyr Leu Glu Ser Trp Val
        515                 520                 525

Lys Asp Asn Arg Leu Asp Gln Leu His Phe Ala Arg Gln Lys Ile Thr
    530                 535                 540

Tyr Cys Tyr Leu Ser Gly Ala Ala Thr Thr Phe Arg Pro Glu Met Gly
545                 550                 555                 560

Tyr Ala Arg Thr Ser Trp Ala Arg Thr Ala Trp Leu Thr Ala Val Ile
                565                 570                 575

Asp Asp Leu Phe Asp Val Gly Gly Leu Glu Gln Glu Gln Glu Asn Leu
            580                 585                 590

Leu Ala Leu Met Glu Lys Trp Glu Glu Pro Gly Glu Asp Glu Tyr Tyr
        595                 600                 605

Ser Glu Asp Val Lys Ile Val Phe Gln Ala Leu Tyr Asn Thr Val Asn
    610                 615                 620

Glu Ile Gly Ala Lys Ala Ser Ala Leu Gln Gly His Asp Val Thr Lys
625                 630                 635                 640

Tyr Leu Val Asp Val Trp Leu His Val Arg Cys Met Lys Val Glu
                645                 650                 655

Ala Glu Trp Gln Arg Ser Gln His Leu Pro Thr Phe Glu Glu Tyr Met
            660                 665                 670
```

```
Glu Ser Gly Met Val Ser Leu Gly Gln Gly Ala Thr Val Met Ser Ala
            675                 680                 685

Leu Phe Leu Ile Gly Glu Lys Leu Pro Glu Gly Val Val Glu Leu Glu
690                 695                 700

Glu Tyr Asp Glu Met Phe Arg Leu Met Gly Thr Cys Gly Arg Leu Leu
705                 710                 715                 720

Asn Asp Ile Arg Gly Ile Glu Arg Glu Ser Asp Gly Lys Met Thr
            725                 730                 735

Asn Gly Val Ser Leu Leu Val His Ala Ser Gly Gly Ser Met Ser Val
            740                 745                 750

Asp Glu Ala Lys Thr Glu Val Met Lys Arg Ile Asp Ala Ser Arg Arg
            755                 760                 765

Lys Leu Leu Ser Leu Val Val Gly Glu Gln Glu Gly Pro Ile Pro Arg
            770                 775                 780

Pro Cys Lys Gln Leu Phe Trp Lys Met Cys Lys Ile Leu His Leu Phe
785                 790                 795                 800

Tyr Tyr Gln Thr Asp Gly Phe Ser Ser Pro Lys Glu Met Val Ser Ala
            805                 810                 815

Val Asp Ala Val Ile Lys Glu Pro Leu Gln Leu Arg Leu Leu
            820                 825                 830

<210> SEQ ID NO 109
<211> LENGTH: 738
<212> TYPE: PRT
<213> ORGANISM: Vitis vinifera

<400> SEQUENCE: 109

Met Phe Asp Lys Val Glu Leu Ser Val Ser Ser Tyr Asp Thr Ala Trp
1               5                   10                  15

Val Ala Met Val Pro Ser Pro Tyr Ser Ser Gln Ala Pro Tyr Phe Pro
                20                  25                  30

Glu Cys Val Asn Trp Leu Leu Glu Asn Gln Ser His Asp Gly Ser Trp
            35                  40                  45

Gly Leu Pro His Pro His Pro Met Leu Val Lys Asp Ala Leu Ser Ser
        50                  55                  60

Thr Leu Ala Ser Val Leu Ala Leu Lys Arg Trp Gly Val Gly Glu Glu
65                  70                  75                  80

Gln Arg Asn Lys Gly Leu Trp Phe Ile Ala Ser Asn Phe Ala Ser Val
                85                  90                  95

Ser Asp Glu Lys Gln His Ser Pro Ile Gly Phe Asp Ile Ile Phe Pro
            100                 105                 110

Gly Met Ile Glu Tyr Ala Lys Glu Leu Asp Leu Asn Leu Pro Leu Gly
        115                 120                 125

Gln Arg Asp Val Asp Ala Met Leu Gln Lys Arg Asp Leu Glu Leu Lys
    130                 135                 140

Gly Ser Leu Gly Ser Asn Thr Lys Ser Arg Glu Ala Tyr Leu Ala Tyr
145                 150                 155                 160

Ile Ser Glu Gly Met Gly Arg Leu Gln Asp Trp Glu Met Val Met Lys
                165                 170                 175

Tyr Gln Met Lys Asn Gly Ser Leu Leu Asn Ser Pro Ser Ala Thr Ala
            180                 185                 190

Ala Ala Leu Ser His Leu Gln Asn Ala Gly Cys Leu Asn Tyr Leu Arg
        195                 200                 205

Ser Leu Leu Glu Lys Phe Gly Asn Ala Val Pro Thr Val Tyr Pro Leu
```

-continued

```
                210                 215                 220
Asp Leu Tyr Ala Arg Leu Cys Leu Val Asp Asn Leu Glu Arg Leu Gly
225                 230                 235                 240

Ile Asp Arg Tyr Phe Arg Met Glu Ile Arg Ser Val Leu Asp Glu Thr
                245                 250                 255

Tyr Arg Cys Trp Leu Gln Arg Glu Glu Ile Phe Ala Asp Arg Ala
                260                 265                 270

Thr Cys Ala Ile Ala Phe Arg Ile Leu Arg Leu Asn Gly Tyr Asp Ile
                275                 280                 285

Ser Ser Val Pro Leu Ala Gln Phe Ala Glu Asp Gln Tyr Phe Lys
                290                 295                 300

Phe Gly Gln Asp Phe Lys Asp Leu Gly Ala Ala Leu Glu Leu Phe Arg
305                 310                 315                 320

Ala Ser Glu Met Ile Ile His Pro Asp Glu Val Val Leu Glu Lys Gln
                325                 330                 335

Asn Ser Trp Ser Ser His Phe Leu Arg Gln Gly Leu Ser Asn Ser Ser
                340                 345                 350

Ile His Ala Asp Arg Leu Asn Lys Tyr Ile Ala Gln Glu Val Glu Asp
                355                 360                 365

Ala Leu Arg Phe Pro Tyr Tyr Ala Asn Leu Asp Arg Ile Ala Asn Arg
                370                 375                 380

Arg Ser Ile Glu His Tyr Asn Val Asp Asp Thr Arg Ile Leu Lys Thr
385                 390                 395                 400

Ala Tyr Arg Ser Ser His Val Cys Asn Lys Asp Phe Leu Lys Leu Ala
                405                 410                 415

Val Glu Asp Phe Asn Phe Cys Gln Ser Ile His Gln Asn Glu Leu Lys
                420                 425                 430

Gln Leu Glu Arg Trp Ile Ile Glu Asn Arg Leu Asp Lys Leu Lys Phe
                435                 440                 445

Ala Arg Gln Lys Leu Ala Tyr Cys Tyr Phe Ser Ala Ala Ala Thr Ile
                450                 455                 460

Phe Ser Pro Glu Gln Ser Asp Ala Arg Leu Ser Trp Ala Lys Asn Ser
465                 470                 475                 480

Val Leu Thr Thr Val Val Asp Asp Phe Phe Asp Ile Gly Gly Ser Glu
                485                 490                 495

Glu Glu Leu Leu Asn Leu Ile Gln Leu Val Glu Lys Trp Asp Ile Asp
                500                 505                 510

Val Ala Val Asp Cys Cys Ser Glu Gln Val Glu Ile Val Phe Ser Ala
                515                 520                 525

Leu His Ser Thr Ile Ser Glu Ile Gly Val Lys Ala Ser Ala Trp Gln
                530                 535                 540

Ala Arg Asn Val Thr Ser His Ile Ile Asp Ile Trp Leu Lys Leu Leu
545                 550                 555                 560

Arg Ser Met Leu Gln Glu Ala Gln Trp Val Ser Asn Lys Ser Ala Pro
                565                 570                 575

Thr Met Asp Glu Tyr Met Thr Asn Ala Tyr Val Ser Phe Ala Leu Gly
                580                 585                 590

Pro Ile Val Leu Pro Ala Leu Tyr Phe Val Gly Pro Lys Leu Ser Glu
                595                 600                 605

Glu Val Val Glu Gly Pro Glu Cys His Lys Leu Tyr Lys Leu Met Ser
                610                 615                 620

Thr Cys Gly Arg Leu Leu Asn Asp Ile His Ser Phe Lys Arg Glu Ser
625                 630                 635                 640
```

```
Lys Glu Gly Lys Ala Asn Ala Leu Ala Leu His Met Ile His Gly Asn
                645                 650                 655

Gly Val Thr Thr Glu Glu Gln Ala Ile Arg Glu Met Lys Gly Leu Val
            660                 665                 670

Lys Ser Gln Arg Arg Glu Leu Gln Arg Leu Val Leu Gln Glu Lys Gly
        675                 680                 685

Ser Thr Val Pro Arg Ile Cys Lys Asp Leu Phe Trp Lys Met Ser Lys
    690                 695                 700

Val Leu His Thr Phe Tyr Glu Lys Asp Asp Gly Phe Thr Ser His Asp
705                 710                 715                 720

Met Leu Arg Ala Val Lys Ser Val Ile Tyr Glu Pro Val Leu Leu Ala
                725                 730                 735

Glu Phe

<210> SEQ ID NO 110
<211> LENGTH: 788
<212> TYPE: PRT
<213> ORGANISM: Lactuca sativa

<400> SEQUENCE: 110

Met Asn Ile Ala Gln Ile Thr Ser Ser Ala Met Leu Val Pro Ser Ser
1               5                   10                  15

His Ile Pro His Arg Ser Trp Val Val Asn Cys Cys Met Val Gln Tyr
                20                  25                  30

Asn Pro Ser Gly Leu Arg Thr Ala Ser Gln Ala Gly Gln Val Asn
            35                  40                  45

Pro Thr Val Met Thr Leu Asp Val Thr Lys Glu Arg Ile Arg Lys Leu
    50                  55                  60

Phe Asn Asn Val Glu Val Ser Val Ser Ser Tyr Asp Thr Ala Trp Val
65                  70                  75                  80

Ala Met Val Pro Ser Pro Asn Ser Pro Lys Ser Pro Cys Phe Pro Asp
                85                  90                  95

Cys Leu Asn Trp Leu Leu Asp Asn Gln Leu Asp Asp Gly Ser Trp Gly
                100                 105                 110

Leu Leu Pro His Gln Ser Pro Leu Ile Lys Asp Thr Leu Ser Ser Thr
            115                 120                 125

Leu Ala Cys Val Leu Ala Leu Lys Arg Trp Asn Val Gly Lys Asp Gln
    130                 135                 140

Ile Asn Lys Gly Leu His Tyr Ile Glu Ser Asn Phe Ala Ser Val Thr
145                 150                 155                 160

Asp Lys Asn Gln Ala Ser Pro Phe Gly Phe Asp Ile Ile Phe Pro Gly
                165                 170                 175

Met Leu Glu Tyr Ala Lys Asp Leu Asp Ile Lys Leu Pro Leu Asn Gln
                180                 185                 190

Thr His Leu Ser Val Met Leu His Glu Arg Glu Leu Glu Leu Arg Arg
            195                 200                 205

Cys His Ser Asn Gly Arg Glu Ala Tyr Leu Ala Tyr Ile Ser Glu Gly
    210                 215                 220

Leu Gly Asn Leu Asn Asp Trp Asn Met Val Met Lys Tyr Gln Met Lys
225                 230                 235                 240

Asn Gly Ser Leu Phe Asn Ser Pro Ser Ala Thr Ala Ser Val Leu Ile
                245                 250                 255

His His Gln Asn Ala Gly Cys Leu His Tyr Leu Thr Ser Leu Leu Asp
                260                 265                 270
```

```
Lys Phe Gly Asn Ala Val Pro Thr Val Tyr Pro Ile Asp Leu Tyr Val
        275                 280                 285

Arg Leu Ser Met Val Asp Thr Leu Glu Arg Leu Gly Ile Lys Arg His
        290                 295                 300

Phe Met Val Glu Ile Gln Asn Val Leu Asp Glu Thr Tyr Arg Cys Trp
305                 310                 315                 320

Val Gln Gly Asp Val Gln Ile Phe Met Asp Val Val Thr Cys Ala Leu
                325                 330                 335

Ala Phe Arg Val Leu Arg Ser Asn Gly Tyr Glu Val Ser Ser Asp Pro
                340                 345                 350

Leu Ala Lys Ile Thr Lys Glu Gly Asp Tyr Met Asn Ser Pro Glu Lys
                355                 360                 365

Pro Phe Lys Asp Val Tyr Thr Ser Leu Glu Val Tyr Lys Ala Ser Gln
        370                 375                 380

Ile Ile Tyr Gln Glu Glu Leu Ala Phe Arg Glu Gln Asn Leu Thr Ser
385                 390                 395                 400

Tyr Leu Pro Ser Ser Asn Lys Leu Ser Asn Tyr Ile Leu Lys Glu Val
                405                 410                 415

Asp Asp Ala Leu Lys Phe Pro Phe Asn Gly Ser Leu Glu Arg Met Ser
                420                 425                 430

Thr Arg Arg Asn Ile Glu His Tyr Asn Leu Asn His Thr Arg Ile Leu
        435                 440                 445

Lys Thr Thr Tyr Ser Ser Ser Asn Ile Ser Asn Lys Asp Tyr Leu Lys
        450                 455                 460

Leu Ala Val Gln Asp Phe Asn Glu Cys Gln Ser Ile Tyr Cys Glu Glu
465                 470                 475                 480

Leu Lys Asp Leu Glu Arg Trp Val Val Glu Asn Arg Leu Asp Lys Leu
                485                 490                 495

Lys Phe Ala Arg Gln Lys Thr Ala Tyr Cys Tyr Phe Ser Ala Ala Ser
                500                 505                 510

Phe Leu Ser Ser Pro Asp Leu Ser Asp Ala Arg Ile Ser Trp Ala Lys
        515                 520                 525

Ser Ser Ile Leu Thr Thr Val Ile Asp Asp Phe Phe Asp Val Gly Gly
        530                 535                 540

Ser Met Asp Glu Leu Val Asn Phe Val His Ile Ile Glu Lys Trp Asn
545                 550                 555                 560

Val Asn Val Glu Asn Asp Cys Cys Ser Glu Glu Val Gly Val Leu Phe
                565                 570                 575

Leu Ala Leu Lys Asp Ala Val Cys Trp Ile Gly Asp Lys Ala Phe Lys
                580                 585                 590

Ile Gln Glu Arg Asn Ile Thr Ser His Val Ile Glu Ile Trp Leu Asp
        595                 600                 605

Leu Val Lys Ser Met Leu Arg Glu Ala Ile Trp Ala Lys Asp Gly Ser
        610                 615                 620

Ile Pro Thr Ile Asn Glu Tyr Met Glu Asn Gly Tyr Val Ser Phe Ala
625                 630                 635                 640

Leu Gly Pro Ile Val Leu Pro Thr Leu Tyr Phe Leu Gly Val Lys Leu
                645                 650                 655

Ser Glu Glu Val Val Gln Ser Ser Glu Tyr His Lys Leu Tyr Glu Val
                660                 665                 670

Met Ser Thr Gln Gly Arg Leu Met Asn Asp Ile His Ser Phe Lys Arg
        675                 680                 685
```

```
Glu Lys Lys Ala Gly Lys Leu Asn Ala Val Ala Leu Tyr Met Ser Asp
    690                 695                 700
Gly Lys Ser Gly Ser Val Glu Glu Val Val Glu Glu Met Lys Ile
705                 710                 715                 720
Leu Thr Lys Ser Gln Arg Lys Glu Met Met Lys Leu Val Leu Glu Thr
                    725                 730                 735
Lys Gly Ser Val Val Pro Arg Val Cys Lys Asp Val Phe Trp Asn Met
                740                 745                 750
Cys Asn Val Leu Asn Leu Phe Tyr Ala Thr Asp Asp Gly Phe Thr Gly
                755                 760                 765
Asn Ala Ile Leu Asp Val Val Lys Glu Ile Ile Tyr Glu Pro Val Ser
770                 775                 780
His Glu Leu Ile
785

<210> SEQ ID NO 111
<211> LENGTH: 789
<212> TYPE: PRT
<213> ORGANISM: Cucurbita maxima

<400> SEQUENCE: 111

Met Tyr Leu Ser Arg Pro Thr Gly Val Ala Arg Phe Ala Ala Ser Ser
1               5                   10                  15
Ser Ser Ser Ser Ala Ser Leu Phe Pro Gly Val Asp Val Asp Thr
                20                  25                  30
Thr Thr Lys Thr Gly Ala Leu His Phe Glu Glu Thr Lys Glu Arg Ile
                35                  40                  45
Lys Lys Leu Phe Asp Lys Val Glu Leu Ser Val Ser Ala Tyr Asp Thr
50                  55                  60
Ala Trp Val Ala Met Val Pro Ser Pro Asn Ser Leu Asn Gln Pro Leu
65                  70                  75                  80
Phe Pro Glu Cys Ile Asn Trp Val Leu Asp Ser Gln His Ala Asp Gly
                85                  90                  95
Ser Trp Gly Leu Leu His Asn Asp Gln Leu Leu Met Lys Ala Asn Leu
                100                 105                 110
Leu Ser Thr Leu Ala Cys Val Leu Thr Leu Lys Arg Trp Asn Ile Gly
                115                 120                 125
His Asp His Met Ser Lys Ala Leu Asp Phe Ile Lys Ser Asn Ile Ala
130                 135                 140
Ser Ala Thr Asp Glu Asn Gln Arg Ser Pro Val Gly Phe Asp Ile Ile
145                 150                 155                 160
Phe Pro Gly Met Ile Glu Tyr Ala Lys Asp Leu Asn Leu Asn Leu Pro
                165                 170                 175
Leu Ala Pro Thr Asn Val Asp Ala Leu Val Arg Lys Lys Glu Leu Glu
                180                 185                 190
Leu Arg Ser Cys Arg Ser Asn Ser Glu Gly Gly Lys Ala Tyr Leu Ala
                195                 200                 205
Tyr Val Ser Glu Gly Ile Gly Lys Leu Gln Asp Trp Asp Met Val Met
                210                 215                 220
Gln Tyr Gln Arg Lys Asn Gly Ser Leu Phe Asn Ser Pro Ser Thr Thr
225                 230                 235                 240
Ala Ala Ala Phe Met His Arg Asn Asp Asp Gly Cys Phe Asp Tyr Leu
                245                 250                 255
Arg Ser Leu Leu Gln Lys Phe Asp Gly Ser Val Pro Thr Ile Tyr Pro
                260                 265                 270
```

```
Leu Asp Ile Tyr Ala Arg Leu His Met Val Asp Ser Leu Gln Lys Phe
            275                 280                 285

Gly Ile Ala Arg His Phe Lys Glu Glu Ile Arg Ser Val Leu Asp Glu
        290                 295                 300

Thr Tyr Arg Cys Trp Met Gln Gly Glu Glu Asn Ile Phe Leu Asp Ala
305                 310                 315                 320

Ser Thr Cys Ala Met Ala Phe Arg Met Leu Arg Val Glu Gly Tyr Asp
                325                 330                 335

Val Ser Ser Asp Gln Leu Thr Gln Phe Ser Glu Asp Ile Phe Pro Asn
            340                 345                 350

Cys Leu Gly Gly Tyr Leu Lys Asp Phe Gly Ala Ser Leu Glu Leu Tyr
        355                 360                 365

Lys Ala Ser Gln Ile Ile Thr His Pro Asp Glu Ser Val Leu Glu Asn
370                 375                 380

Ile Asn Ser Trp Thr Ser Arg Phe Leu Lys His Gly Leu Ser Ser Asp
385                 390                 395                 400

Ser Val Trp Ser Asp Arg Thr Asp Ser Val Val Lys Gln Glu Ala Val
                405                 410                 415

Asn Ala Leu Glu Phe Pro Tyr Asn Ala Thr Leu Glu Arg Leu Ile Ser
            420                 425                 430

Lys Arg Ala Met Glu Ser Tyr Ser Gly Asp Ile Val Arg Ile Ser Lys
        435                 440                 445

Ser Pro Tyr Ala Cys Leu Asn Phe Gly His Gln Asp Phe Leu Glu Leu
450                 455                 460

Ala Val Glu Asp Phe Asn Thr Leu Gln Arg Ile His Leu Lys Glu Leu
465                 470                 475                 480

Glu Glu Leu Gln Arg Trp Val Glu Asn Lys Leu Asp Glu Leu Lys
                485                 490                 495

Phe Phe Arg Leu His Leu Gly Tyr Cys Tyr Phe Ala Ala Ala Thr
            500                 505                 510

Leu Thr Asp Pro Glu Leu His Asp Ala Arg Ile Ala Trp Ala Gln Asn
        515                 520                 525

Gly Val Leu Thr Thr Val Val Asp Asp Phe Tyr Asp Gly Gly Ser
            530                 535                 540

Glu Glu Glu Leu Asp Asn Leu Ile Glu Leu Val Glu Lys Trp Asp Pro
545                 550                 555                 560

Asp Gly Glu Val Gly Tyr Cys Ser Lys Asp Val Glu Ile Val Phe Leu
                565                 570                 575

Ala Leu His Ser Thr Val Cys Glu Ile Gly Arg Arg Ala Leu Val Trp
            580                 585                 590

Gln Gly Arg Ser Val Met Arg Asn Val Ile Asp Gly Trp Leu Ala Leu
        595                 600                 605

Leu Lys Val Met Arg Lys Glu Ala Glu Trp Ser Thr Asn Lys Val Val
610                 615                 620

Pro Ser Met Gly Glu Tyr Met Glu Gln Ala His Val Ser Phe Ala Leu
625                 630                 635                 640

Gly Pro Ile Ile Leu Pro Met Leu Phe Phe Val Gly Pro Lys Leu Ser
                645                 650                 655

Glu Glu Met Ile Gly Ser Cys Glu Tyr Gln Lys Leu Tyr Lys Leu Met
            660                 665                 670

Ser Thr Ala Gly Arg Leu Lys Asn Asp Ile Arg Ser Tyr Asp Arg Glu
        675                 680                 685
```

-continued

```
Cys Lys Glu Gly Lys Leu Asn Ile Leu Ser Leu Trp Met Ile Asp Gly
    690              695              700

Gly Gly Asn Val Thr Lys Glu Glu Ala Ile Glu Ala Ile Lys Gly Asp
705              710              715              720

Phe Glu Arg Ala Ile Arg Glu Leu Leu Gly Leu Val Leu Gln Glu Asn
            725              730              735

Thr Thr Ile Pro Arg Ala Cys Lys Asp Leu Phe Trp Lys Leu Met Ser
            740              745              750

Ile Val Asn Leu Phe Tyr Met Glu Asp Asp Gly Tyr Thr Ser Asn Arg
        755              760              765

Leu Met Asn Thr Val Lys Ala Met Phe Glu Gln Pro Met Asp Leu Asp
    770              775              780

Ala Leu Leu Asn Lys
785
```